US008222288B2

(12) United States Patent
Wang et al.

(10) Patent No.: US 8,222,288 B2
(45) Date of Patent: Jul. 17, 2012

(54) SMALL MOLECULE INHIBITORS OF MDM2 AND THE USES THEREOF

(75) Inventors: Shaomeng Wang, Saline, MI (US); Dongguang Qin, Auburn Hills, MI (US); Jianyong Chen, Ann Arbor, MI (US); Shanghai Yu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 88 days.

(21) Appl. No.: 12/815,113

(22) Filed: Jun. 14, 2010

(65) Prior Publication Data

US 2010/0317661 A1  Dec. 16, 2010

Related U.S. Application Data

(62) Division of application No. 11/848,089, filed on Aug. 30, 2007, now Pat. No. 7,737,174.

(60) Provisional application No. 60/841,150, filed on Aug. 30, 2006, provisional application No. 60/878,795, filed on Jan. 5, 2007.

(51) Int. Cl.
*A61K 31/407* (2006.01)
*C07D 487/10* (2006.01)

(52) U.S. Cl. ........ 514/409; 514/410; 514/444; 514/445; 514/462; 548/409; 549/59; 549/265

(58) Field of Classification Search .................. None
See application file for complete search history.

(56) References Cited

U.S. PATENT DOCUMENTS

| 3,219,661 A | 11/1965 | Shavel, Jr. et al. | |
| 2006/0211757 A1 * | 9/2006 | Wang et al. ................ | 514/409 |

FOREIGN PATENT DOCUMENTS

| CN | 1410401 | 4/2003 |
| GB | 1056537 | 1/1967 |
| JP | 40-23184 | 10/1965 |
| JP | 44 4986 | 2/1969 |
| RU | 2084449 | 7/1997 |
| RU | 2186776 | 10/2002 |
| WO | 03/051360 | 6/2003 |
| WO | 2005/110992 | 11/2005 |
| WO | 2006/091646 | 8/2006 |

OTHER PUBLICATIONS

CA Abstract compound CAS RN 701304-77-0 (2004).*
Wu and Farrelly, Toxicology 236:1-6, 2007.*
Harley-Mason J, et al., 728. Hydroxytryptamines, Part IV, Synthesis and Reactions of 2-3'-oxindolylethylamines. Journal Chemical Society, 1958, pp. 3639-3642, p. 3639, compound (V).
Kabankin, A.S., et al., Analysis of relationship between structure and hepatoprotective activity of indole derivatires. Chemical and pharmaceutical magazine, 2005, vol. 39, No. 4, M., Volium, p. 24-28, table 1, compounds 4, 10 (learning sample), compound 1 (check sample).
Geise, B., et al., Radical cyclization reactions, Organice reactions (Hoboken, NJ, United States), 48, 1996, online, found from database ASC on STN, CA: 149:5550940, compounds with RN 159979-08-5, 159979-09-6.
Chene, Patrick, "Inhibiting the p53-MDM2 Interaction: An Important Target for Cancer Therapy," Nature Reviews: Cancer, Feb. 2003, vol. 3, pp. 102-109.
Garcia-Echeverria, ,Carlos, et al., "Discovery of Potent Antagonists of the Interaction between Human Double Minute 2 and Tumor Suppressor p53," J. Med. Chem.. (2000), 43, pp. 3205-3208.
Kussie, Paul H., "Structure of the MDM2 Oncoprotein Bound to the p53 Tumor Suppressor Transactivation Domain," Science, vol. 274, Nov. 8, 1996, pp. 948-953.
Nikolovska-Coleska, Zaneta, et al., "Development and optimization of a binding assay for the XIAP BIR3 domain using fluorescence polarization," Analytical Biochemistry 332 (2004), pp. 261-273.
Sebahar, Paul R., et al., "The Asymmetric Total Synthesis of (+)- and (−)-Spirotryprostatin B," American Chemical Society (2000), vol. 122, No. 23, p. 5666.
Usui, Takeo, et al., "Tryprostatin A, a specific and novel inhibitor of microtubule assembly," Biochem J. (1998) 333, pp. 543-548.
Vassilev, Lyubomir T., et al., "In Vivo Activation of the p53 Pathway by Small-Molecule Antagonists of MDM2," Science, vol. 303, Feb. 6, 2004, pp. 844-848.
Vogelstein, Bert, et al., "Surfing the p53 network," Nature, vol. 408, Nov. 16, 2000, pp. 307-310.
Australian Patent Application No. 2006216780 First Examiner's Report dated Mar. 5, 2009.
Sebahar P.R. and William R.M., "the synthesis of Spirooxindole Pyrrolidines Via an Asymmetric Azomethine Ylide . . . " Heterocycles, 2002, vol. 58, pp. 563-575.
Onishi T., et al., "Concise, Asymmetric total Synthesis of Spirotryprostatin A," Tetrahedron, 60 (2004) 9503-9515.
Cochard F., et al., "Synthesis of Substituted 1,2,3,4-Tetrahydro-1-thiacarbazole and . . . " European Journal of Organic Chemistry, 2002, vol. 20, pp. 3481-3490.
Database CAPLUS on STN, Chem. Abstr., Accession No. 1996:127543.
Ding et al., "Structure-based design of spiro-oxindoles as potent, specific small-molecule inhibitors of the MDM2-p53 interaction," J. Med. Chem. 49:3432 (2006).
Pellegrini et al., "Total Synthesis of (+)-Elacomine and (−)-Isoelacomine, Two Hitherto Unnamed Oxindole Alkaloids from *Elaeagnus commutata*," Helvetica CHimica Acta 79:151-68 (1996.
Singapore Patent Application No. 200706163-3, Office Action dated Sep. 14, 2009.
Onishi, T.,. et al., "Concise, Asymmetric Total Synthesis of Spirotryprostatin A", Organic Letters, Jun. 26, 2003, vol. 5, No. 17, pp. 3135-3137.
Miyake, F.Y.., et al., "Preparation and Synthetic Application of 2-Halotryptophan Methyl Esters: Synthesis of Spirotryprostatin B", Angewandte Chemie/ International Edition, 2004, vol. 43, No. 40, pp. 5357-5360.

(Continued)

*Primary Examiner* — Yong Chu
(74) *Attorney, Agent, or Firm* — Casimir Jones SC

(57) ABSTRACT

The invention relates to small molecules which function as inhibitors of the interaction between p53 and MDM2. The invention also relates to the use of these compounds for inhibiting cell growth, inducing cell death, inducing cell cycle arrest and/or sensitizing cells to additional agent(s).

16 Claims, No Drawings

OTHER PUBLICATIONS

Sebahar, P.R., et al., "Asymmetric, Sterocontrolled total synthesis of (+) and (−)-spirotryprostatin B via a diastereoselective azomethine ylide . . . " Tetrahedron, Mar. 21, 2002, 6311-6322.

Lu, Y., et al., "Discovery of a Nanomolar Inhibitor of the Human Murine Double Minute 2(MDM2)-p53 Interaction through an Integrated Virtual Database Screening Strategy", Journal of Medicinal Chemistry, Jan. 9, 2006, vol. 49, No. 13, pp. 3759-3762.

Ding, et al., "Structure-Based Design of Potent Non-Peptide MdM2 Inhibitors" Journal of the American Chemical Society, Jul. 27, 2005.

BAN, Chemical & Pharmaceutical Bulletin (1963), 4, pp. 441-445.

Eurasian Search Report (translated), EA Patent Application No. 200701771, Dated May 22, 2008.

Chem. Abstr. 130:311714, compound with RN 223663-19-2. Incze Maria et al. Intramolecular Mannich reaction of 2-oxotryptamines with acetone yielding spiro [indole-3, 3'-pyrrolidin]-2-ones. Collection of Czchoslovak Chemical Communications, 64 (2), 408-416 (English) 1999.

Chem. Abstr. 122:56269, compound with RN 160080-01-3. Pellegrini Claudio et al. Synthesis of the oxindole alkaloid (−)-horsfiline. Tetrahedron: Asymmetry, 5(10), 1979-92 (English) 1994.

Chem. Abstr. 132:207995, compound with RN 6786-41-0, Somei Masanori et al. Chemistry of indoles. 95. Preparation and A novel rearrangement reaction of 1, 2, 3, 4-tetrahydro-9-hydroxy-beta carboline, and their applications for the total synthesis of (+/−)-coerulescine. Heterocycles, 53(1), 7-10 (English) 2000.

Chem. Abstr. J 28:257595, compound with RN 6786-41-0. Cossy Janine E.E. et al. A convenient route to spiropyrrolidinyl-oxindole alkaloids via C-3 substituted enepyrrolidine carbamate radical cyclization. Tetrahedron Letters, 39(16), 2331-2332 (English) 1998.

Chem. Abstr. 51:29816, compound with RN 6786-41-0. Van Tamelen et al. Spiro [pyrrolidine-3, 3'-oxindole and-2'-pseudoindoxyl]. Chemistry & Industry (London, United Kingdom) 1 145-6 (Unavailable) 1956.

Chem. Abstr. 138:401949, compound with RN 404871-51-8. Lizos Dimitrios E. et al. Concise synthesis of (−/−)-horsfiline and (+/−)-coerulescine by tandem cyclisation of iodoaryl alkenyl azides. Organic & Biomolecular Chemistry, 1(1), 117-122 (English) 2003. 136:247728, compound with RN 404871-51-8. Lizos Dimitrios et al. A novel and economical route to (+/−)-horsfiline using an aryl iodoazide tandem radical cyclization strategy. Chemical Communications (Cambridge, United Kingdom) (24); 2732-2733 (English) 2001.

Chem. Abstr. 132:93510 compound with RN 254428-32-5, Alper Phil B. Facile, novel methodology for the synthesis of spiro [pyrrolidin-3, 3' oxindoles]: catalyzed ring expansion reactions of cyclopropanes by aldimines. Angewandte Chemie, International Edition, 38(21), 3186-3189 (English) 1999.

Chem. Abstr. 130:352456 compound with RN 225110-75-8, Edmondson Scott et al. Total Synthesis of Spirotryprostatin A, Leading to the Discovery of Some Biologically Promising Analogs. Journal of the American Chemical Society, 121 (10), 2147-2155 (English) 1999.

Chem. Abstr. 95:220205 compound with RN 79888-04-3, Doe de maindreville Michele et al. Syntheses of indole derivatives. VII. Synthesis and chemical reactions of the tetracyclic system common to alkaloids with an anilinocrylic ester chromophore. Bulletin de la Societe Chimique de France (5-6, Pt.2), 179-84 (French) 1981.

Chem. Abstr. 137:185435 compound with RN 449777-56-4, Grigg Ronald et al. Spirooxindoles via bimetallic [Pd(O)/Ag (I)] catalytic intramolecular Heck-I, 3-dipolar cycloaddition cascade reactions. Tetrahedron letters, 43(14), 2605-2608 (English) 2002.

Schubert, et al., "Solvent injection as a new approach for manufacturing lipid nanoparticles—evaluation of the method and process parameters," European Journal of Pharmaceutics and Biopharmaceutics 55 (2003) 125-131.

Ding, et al., "Structure-Based Design of Potent Non-Peptide MdM2 Inhibitors" Journal of the American Chemical Society, Jul. 27, 2005, vol. 127, No. 29, pp. 10130-10131.

International Search Report and Written Opinion, PCT/US2007/019128, mailed Sep. 24, 2008.

Helvetica Chimica Acta; 1996, vol. 79, No. 1, pp. 151-168.

Ding, K., et al., "Synthesis of Spirooxindoles via asymmetric 1,3-dipolar cycloaddition", Tetrahedron Letters, Elsevier, Amsterdam, NL, Aug. 29, 2005, vol. 46, No. 35, pp. 5949-5951.

Baxter E.W., et al., Reductive animations of carbonyl compounds with boronhydride and borane reducing agents. Organic reactions (Hoboken, NJ, United States, 59 (online) Found from database ASC on STN, CA: 149-5759820, compound with RN 1071179-22-0 (2002).

Wu, Xiangwei, et al., "The p53-mdm-2 autoregulatory feedback loop," Genes & Development 7, pp. 1126-1132 (1993).

\* cited by examiner

SMALL MOLECULE INHIBITORS OF MDM2 AND THE USES THEREOF

CROSS-REFERENCE TO RELATED APPLICATIONS

The present application is a divisional of U.S. patent application Ser. No. 11/848,089, filed Aug. 30, 2007 which will issue on Jun. 15, 2010 as U.S. Pat. No. 7,737,174, which claims priority to expired U.S. Provisional Patent Application Ser. No. 60/841,150, filed Aug. 30, 2006, and expired U.S. Provisional Patent Application Ser. No. 60/878,795, filed Jan. 5, 2007, all of which are herein incorporated by reference in their entireties.

STATEMENT REGARDING FEDERALLY SPONSORED RESEARCH OR DEVELOPMENT

This invention was made with government support under CA069568 and CA121279 awarded by the National Institutes of Health. The government has certain rights in the invention.

BACKGROUND OF THE INVENTION

1. Field of the Invention

This invention is in the field of medicinal chemistry. In particular, the invention relates to small molecules which function as antagonists of the interaction between p53 and MDM2 and their use therapeutics for the treatment of cancer and other diseases.

2. Related Art

The aggressive cancer cell phenotype is the result of a variety of genetic and epigenetic alterations leading to deregulation of intracellular signaling pathways (Ponder, *Nature* 411:336 (2001)). The commonality for all cancer cells, however, is their failure to execute an apoptotic program, and lack of appropriate apoptosis due to defects in the normal apoptosis machinery is a hallmark of cancer (Lowe et al., *Carcinogenesis* 21:485 (2000)). The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407:810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

The p53 tumor suppressor plays a central role in controlling cell cycle progression and apoptosis (Vogelstein et al., *Nature* 408:307 (2000)). It is an attractive therapeutic target for anticancer drug design because its tumor suppressor activity can be stimulated to eradicate tumor cells (Vogelstein et al., *Nature* 408:307 (2000); Chene, *Nat. Rev. Cancer* 3:102 (2003)). A new approach to stimulating the activity of p53 is through inhibition of its interaction with the protein MDM2 using non-peptide small molecule inhibitors (Chene, *Nat. Rev. Cancer* 3:102 (2003); Vassilev et al., *Science* 303:844 (2004)). MDM2 and p53 are part of an auto-regulatory feedback loop (Wu et al., *Genes Dev.* 7:1126 (1993)). MDM2 is transcriptionally activated by p53 and MDM2, in turn, inhibits p53 activity by at least three mechanisms (Wu et al., *Genes Dev.* 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation. Hence, by functioning as a potent endogenous cellular inhibitor of p53 activity, MDM2 effectively inhibits p53-mediated apoptosis, cell cycle arrest and DNA repair. Therefore, small-molecule inhibitors that bind to MDM2 and block the interaction between MDM2 and p53 can promote the activity of p53 in cells with a functional p53 and stimulate p53-mediated cellular effects such as cell cycle arrest, apoptosis, or DNA repair (Chene, *Nat. Rev. Cancer* 3:102 (2003); Vassilev et al., *Science* 303:844 (2004))

Although high-affinity peptide-based inhibitors have been successfully designed in the past (Garcia-Echeverria et al., *Med. Chem.* 43:3205 (2000)), these inhibitors are not drug-like molecules because of their poor cell permeability and in vivo bioavailability. Despite intensive efforts by the pharmaceutical industry, high throughput screening strategies have had very limited success in identifying potent, non-peptide small molecule inhibitors. Accordingly, there is a need for non-peptide, drug-like, small molecule inhibitors of the p53-MDM2 interaction.

The design of non-peptide small-molecule inhibitors that target the p53-MDM2 interaction is currently being pursued as an attractive strategy for anti-cancer drug design (Chene, *Nat. Rev. Cancer* 3:102 (2003); Vassilev et al., *Science* 303:844 (2004)). The structural basis of this interaction has been established by x-ray crystallography (Kussie et al., *Science* 274:948 (1996)). The crystal structure shows that the interaction between p53 and MDM2 is primarily mediated by three hydrophobic residues (Phe19, Trp23 and Leu26) from p53 and a small, deep hydrophobic cleft in MDM2. This hydrophobic cleft is an ideal site for designing small-molecule inhibitors that can disrupt the p53-MDM2 interaction (Chene, *Nat. Rev. Cancer* 3:102 (2003)).

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is a decrease in the tumor suppressor activity of p53, which in many instances is due to the inhibitory actions of MDM2 on p53 in tumor cells containing functional p53. The inhibition of p53 activity results in alterations in apoptosis pathways as well as cell cycle regulation.

The present invention contemplates that exposure of animals suffering from cancer to therapeutically effective amounts of drug(s) (e.g., small molecules) that increase the function(s) of p53 and p53-related proteins (e.g., p63, p73) by inhibiting the interaction between p53 or p53-related proteins and MDM2 or MDM2-related proteins (e.g., MDMX) will inhibit the growth of cancer cells or supporting cells outright and/or render such cells as a population more susceptible to the cell death-inducing activity of cancer therapeutic drugs or radiation therapies. In particular, the inhibitors of the invention may prolong the half-life of p53 by interfering with the p53-MDM2 interaction that would normally promote degradation of p53. The present invention contemplates that inhibitors of the interaction between p53 or p53-related proteins and MDM2 and MDM2-related proteins satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds will lower the apoptotic threshold of all cells, the proportion of cells that will successfully execute the apoptosis program in response to the apoptosis inducing activity of anticancer drugs/radiation is increased. Alternatively, the compounds of the present invention will be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the present compounds. Also, since the compounds of the present invention may act at least in part by stimulating the pro-apoptotic and/or cell cycle-inhibiting activities of p53 and p53-related proteins, the exposure of cancer cells and supporting cells to therapeutically effective amounts of the compounds should be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

In other embodiments of the invention, inhibitors of the interaction between p53 or p53-related proteins and MDM2 and MDM2-related proteins may protect normal (e.g., non-hyperproliferative) cells from the toxic effects of certain chemotherapeutic agents and radiation, possibly through the ability of the inhibitors to induce cell cycle arrest. In particular, the inhibitors of the invention may cause cell cycle arrest in cells comprising wild-type p53 while having no effect on cancer cells comprising mutated or deleted p53. This differential protective effect may allow for more effective treatment of cancer by allowing the use of higher doses or longer treatments of chemotherapeutic agents or treatments without increasing the toxic side effects of such treatment.

The present invention relates to compounds that are useful for inhibiting the interaction between p53 or p53-related proteins and MDM2 or MDM2-related proteins and increasing the sensitivity of cells to inducers of apoptosis and/or cell cycle arrest. In one particular embodiment, the compounds have Formula I:

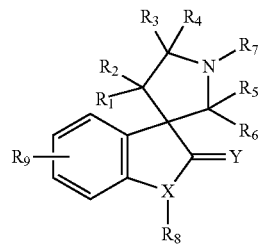

or a pharmaceutically acceptable salt or prodrug thereof, wherein:
X is CH, O, N, or S, wherein $R_8$ is absent if X is O or S;
Y is O, S, or NR';
$R_1$, $R_2$, $R_3$, $R_4$, $R_5$, $R_6$, and $R_7$ are independently H or optionally substituted alkyl, cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, (C=NR')NR''R''', or NR'R''; or
$R_7$ forms an aryl, cycloalkyl, or heterocyclic group with one of $R_5$ or $R_6$;
$R_8$ is H or optionally substituted alkyl, cycloalkyl, alkenyl, cycloalkenyl, alkynyl, aryl, heterocyclic, $CO_2R'$, $OCOR'$, $CONR'R''$, $SO_2NR'R''$, or (C=NR')NR''R''';
$R_9$ represents a 6-chloro and a 5-fluoro group; and
each R', R'' and R''' is independently H or optionally substituted alkyl, cycloalkyl, alkenyl, cycloalkenyl, alkynyl, aryl, or heterocyclic; or
R' and R'', or R'' and R''', form a ring;
wherein one of $R_3$ and $R_4$ is CONRR', and one of R and R' is an optionally substituted cycloalkyl-alkyl or monocyclo-heterocycloalkyl group or a dihydroxyalkyl amino group not containing a hydroxyl group at the 3-position of the alkyl group.

The invention relates to compounds represented by Formula I, which are inhibitors of the interaction between p53 or p53-related proteins and MDM2 or MDM2-related proteins. The invention relates to the use of the compounds of the invention to induce cell cycle arrest and/or apoptosis in cells containing functional p53 or p53-related proteins. The invention also relates to the use of the compounds of the invention for sensitizing cells to additional agent(s), such as inducers of apoptosis and/or cell cycle arrest, and chemoprotection of normal cells through the induction of cell cycle arrest prior to treatment with chemotherapeutic agents. In one embodiment, the invention relates to methods of rendering a normal cell resistant to chemotherapeutic agents or treatments, comprising contacting the cell with a compound of the invention. In one embodiment, the invention relates to methods of protecting normal cells in an animal with a hyperproliferative disease from the toxic side effects of chemotherapeutic agents or treatments, comprising administering to said animal a compound of the invention. In a particular embodiment, the invention is directed to the treatment, amelioration, or prevention of disorders, side effects, or conditions caused by the administration of chemotherapeutic agents to normal noncancerous cells by administering to an animal undergoing chemotherapy a compound of the present invention. Examples of such disorders and conditions caused by chemotherapy include, without limitation, mucositis, stomatitis, xerostomia, gastrointestinal disorders, and alopecia.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional p53 or p53-related proteins. In other embodiments, the invention relates to the use of the compounds of the invention to protect normal (e.g., non-hyperproliferative) cells from the toxic side effects of chemotherapeutic agents and treatments by the induction of cell cycle arrest in those cells.

The present invention provides pharmaceutical compositions comprising a compound of Formula I in a therapeutically effective amount to induce apoptosis in cells or to sensitize cells to inducers of apoptosis.

The invention further provides kits comprising a compound of Formula I and instructions for administering the compound to an animal. The kits may optionally contain other therapeutic agents, e.g., anticancer agents or apoptosis-modulating agents.

The invention also provides methods of making compounds of Formula I.

DETAILED DESCRIPTION OF THE INVENTION

The present invention relates to compounds represented by Formula I, which function as inhibitors of the interaction between p53 or p53-related proteins and MDM2 or MDM2-related proteins. By inhibiting the negative effect of MDM2 or MDM2-related proteins on p53 or p53-related proteins, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of Formula I alone or in combination with additional agent(s), e.g., an inducer of apoptosis or a cell cycle disrupter. The invention further relates to methods of treating, ameliorating, or preventing disorders in an animal, such as those that are responsive to induction of apoptosis, comprising administering to the animal a compound of Formula I and additional agent(s), e.g., an inducer of apoptosis. Such disorders include those characterized by a dysregulation of apoptosis and those characterized by the proliferation of cells expressing functional p53 or p53-related proteins. In other embodiments, the invention relates to methods of protecting normal (e.g., non-hyperproliferative) cells in an animal from the toxic side effects of chemotherapeutic agents and treatments comprising administering to the animal a compound of Formula I.

The terms "anticancer agent" and "anticancer drug," as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formula I), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "functional p53," as used herein, refers to wild-type p53 expressed at normal, high, or low levels and mutant p53 that retains at least 5% of the activity of wild-type p53, e.g., at least 10%, 20%, 30%, 40%, 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX and HDM2.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Apoptosis-modulating agents include those which are inducers of apoptosis, such as TNF or a TNF-related ligand, particularly a TRAMP ligand, a Fas/CD95 ligand, a TNFR-1 ligand, or TRAIL.

In one aspect of the invention, the inhibitors of the interaction between p53 and MDM2 are compounds of Formula I:

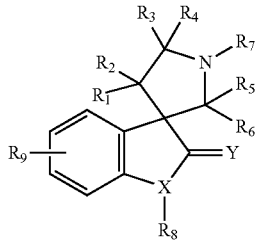

I or a pharmaceutically acceptable salt or prodrug thereof, wherein:

X is CH, O, N, or S, wherein $R_8$ is absent if X is O or S;

Y is O, S, or NR';

$R_1$, $R_2$, $R_3$, $R_4$, $R_5$, $R_6$, and $R_7$ are independently H or optionally substituted alkyl, cycloalkyl, alkenyl, cycloalkenyl, alkynyl, aryl, heterocyclic, $CO_2R'$, OCOR', CONR'R'', NR''COR', NR'SO$_2$R'', SO$_2$NR'R'', (C=NR')NR''R''', or NR'R''; or $R_7$ forms an aryl, cycloalkyl, or heterocyclic group with one of $R_5$ or $R_6$;

$R_8$ is H or optionally substituted alkyl, cycloalkyl, alkenyl, cycloalkenyl, alkynyl, aryl, heterocyclic, $CO_2R'$, OCOR', CONR'R'', SO$_2$NR'R'', or (C=NR')NR''R''';

$R_9$ represents a 6-chloro and a 5-fluoro group; and each R', R'' and R''' is independently H or optionally substituted alkyl, cycloalkyl, alkenyl, cycloalkenyl, alkynyl, aryl, or heterocyclic; or R' and R'', or R'' and R''', form a ring;

wherein one of $R_3$ and $R_4$ is CONRR', and one of R and R' is an optionally substituted cycloalkyl-alkyl or monocyclo-heterocycloalkyl group or a dihydroxyalkyl amino group not containing a hydroxyl group at the 3-position of the alkyl group.

In a more particular embodiment, one of $R_1$ and $R_2$ of Formula I is a substituted or unsubstituted aryl (e.g., phenyl), substituted or unsubstituted heteroaryl, cycloalkyl, straight or branched alkyl, amide or ester.

In another embodiment, one of $R_5$ and $R_6$ is a $C_{3-18}$ alkyl group, e.g., propyl, isopropyl, sec-butyl, tert-butyl, isopentyl, cyclopentyl, norbornyl, or adamantyl, or a 5- or 6-membered aryl or heteroaryl group.

In another embodiment, the compounds of Formula I have a stereochemical structure as shown in Formula II or Formula III:

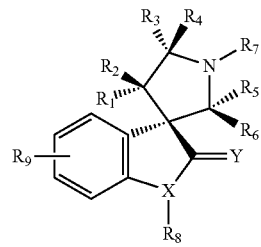

II

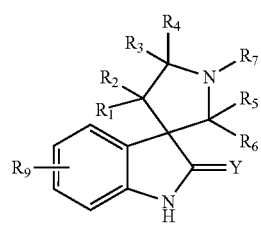

III or a pharmaceutically acceptable salt or prodrug thereof.

In one embodiment, the compounds of Formula I have Formula IV:

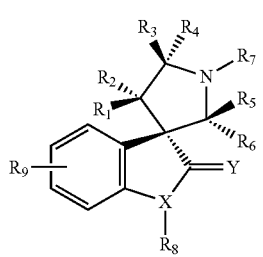

IV wherein $R_1$-$R_9$ and Y are as defined above.

In another embodiment, the compounds of Formula IV have a stereochemical structure as shown in Formula V or Formula VI:

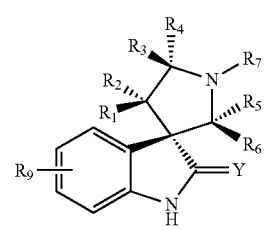

V

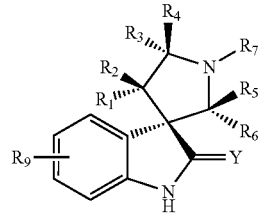

VI or a pharmaceutically acceptable salt or prodrug thereof.

In one embodiment, the compounds of Formula I have Formula VII:

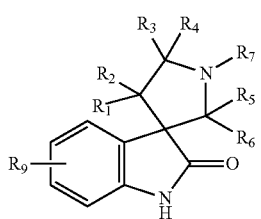

VII wherein $R_1$-$R_9$ are as defined above.

In another embodiment, the compounds of Formula VII have a stereochemical structure as shown in Formula VIII or Formula IX:

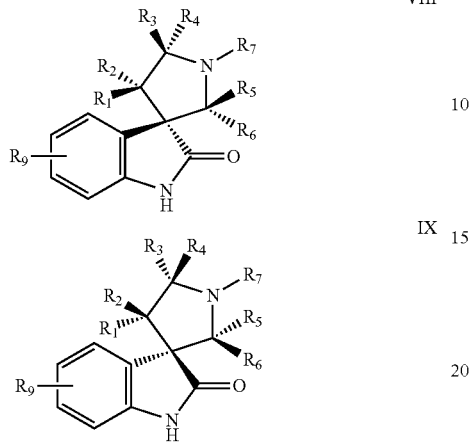

VIII

IX or a pharmaceutically acceptable salt or prodrug thereof.

In one embodiment, the compounds of Formula I have Formula X:

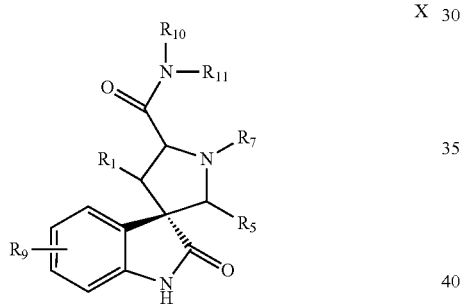

X wherein:
$R_1$, $R_5$, $R_7$, and $R_9$ are as defined above;
$R_{10}$ is H; and
$R_{11}$ is an optionally substituted cycloalkyl-alkyl or monocyclo-heterocycloalkyl group or a dihydroxyalkyl amino group not containing a hydroxyl group at the 3-position of the alkyl group;
or $R_{10}$ and $R_{11}$ together form an optionally substituted monocyclo-heterocycloalkyl group.

Examples of substituted cycloalkyl-alkyl groups include $C_{1-6}$ alkyl substituted by a cycloalkyl group as described herein below which is substituted further by one or more hydroxyl groups. Examples of heterocycloalkyl groups include $C_{1-6}$ alkyl substituted by a monocyclo-heterocycloalkyl group as described herein below.

Particular examples of cycloalkyl-alkyl groups include 2-(3-hydroxycyclopentyl)ethylamino, and 3-(3-hydroxycyclopentyl)propylamino groups. The respective hydroxyl groups may have either the R or S configurations.

Particular examples of substituted heterocycloalkyl groups include 2-(1-morpholinyl)ethylamino and 3-(1-morpholinyl)propylamino groups.

Particular examples of dihydroxyalkylamino groups include R and S 4,5-dihydroxypentylamino, and 4-hydroxy-3-(methylhydroxy)butylamino groups.

It is expected that when a hydroxyl group is not present at the 3-position of the alkyl group, the compound may exhibit improved stability during its preparation. Without being limited to any particular theory, the improved stability may result from the absence of a nucleophilic 3-hydroxyl group which may displace the amino group of the amide thus forming a 6-membered ester containing ring. It is believed that dihydroxyalkyl groups not containing a 3-hydroxy group will not participate in such a reaction and will be more stable and able to be made in higher yield.

In a further embodiment, the compounds of Formula I have one of Formulae XI-XXVI:

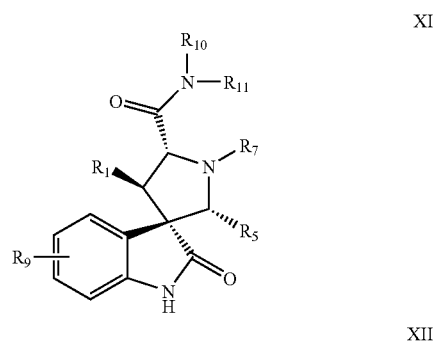

XI

XII

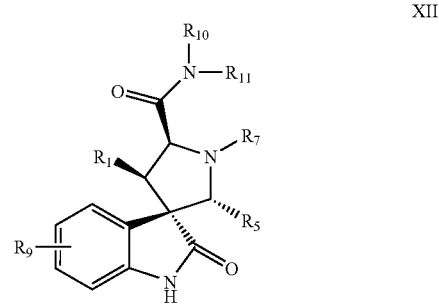

XIII

XIV

XV
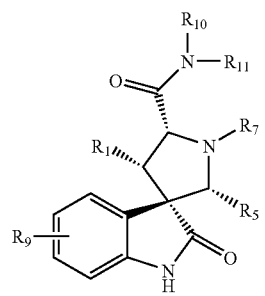
XVI
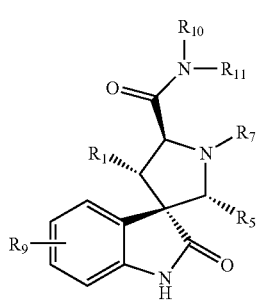
XVII
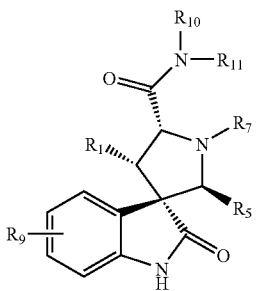
XVIII
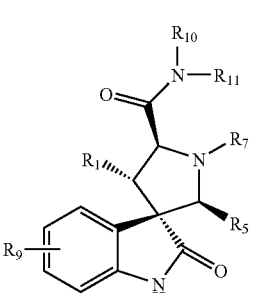
XIX
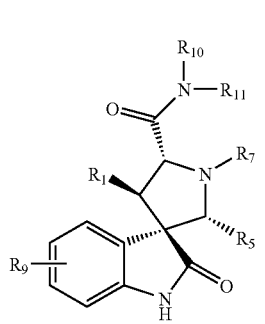
XX
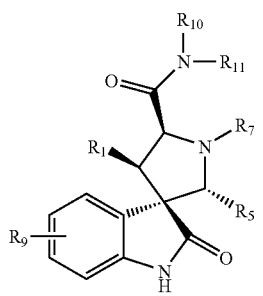
XXI
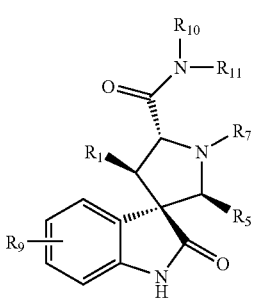
XXII
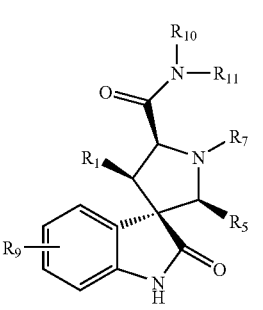
XXIII
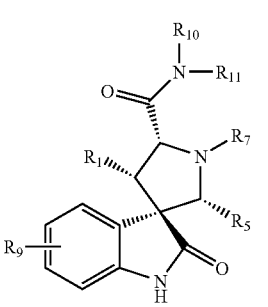
XXIV
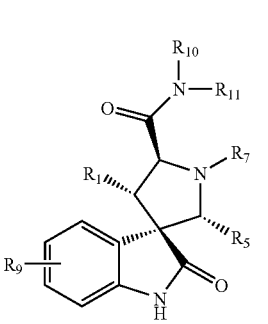

-continued

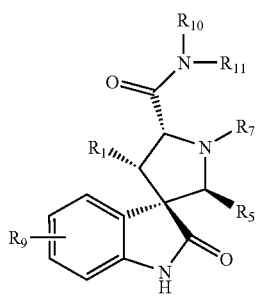
XXV

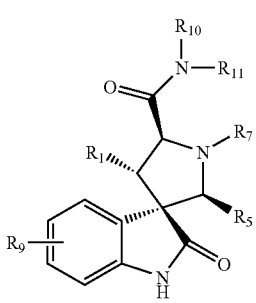
XXVI wherein $R_1$, $R_5$, $R_7$, $R_9$, $R_{10}$, and $R_{11}$ are as defined above.

In another embodiment, the compounds of Formula I have one of Formulae XXVII and XXVIII:

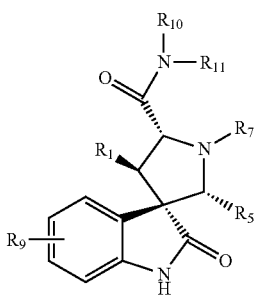
XXVII

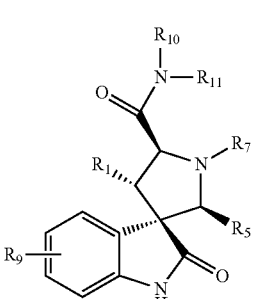
XXVIII wherein $R_1$, $R_5$, $R_7$, $R_9$, $R_{10}$, and $R_{11}$ are as defined above.

In another embodiment, the compounds of Formula I have Formula XLVIII:

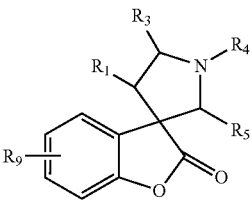
XLVIII wherein:

$R_1$, $R_3$, $R_4$, $R_5$ and $R_9$ are as defined above.

In a further embodiment, the compounds of Formula I have one of Formulae XLIX-LXIV:

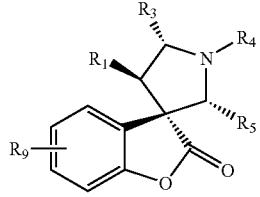
XLIX

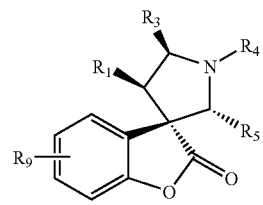
L

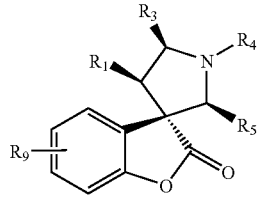
LI

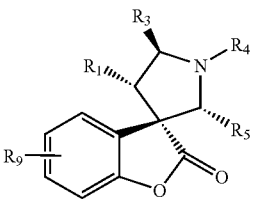
LII

LIII

LIV
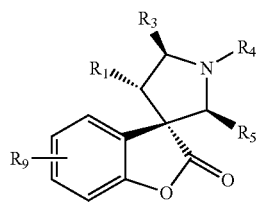
LV
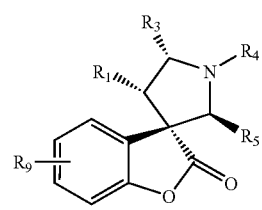
LVI
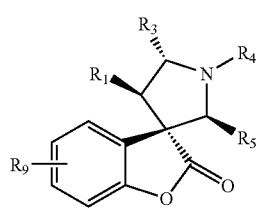
LVII
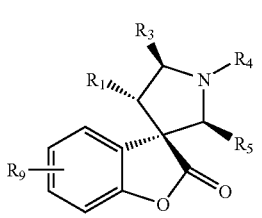
LVIII
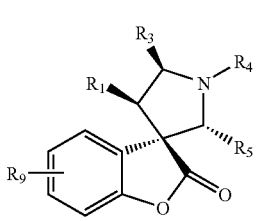
LIX
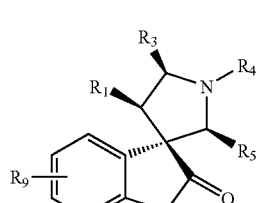
LX
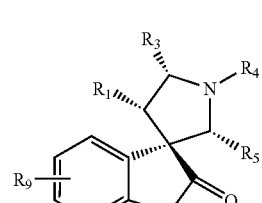
LXI
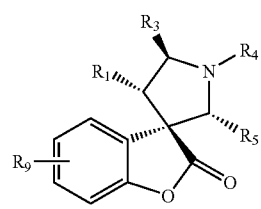
LXII
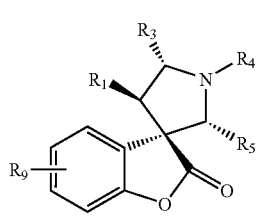
LXIII
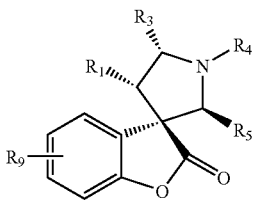
LXIV
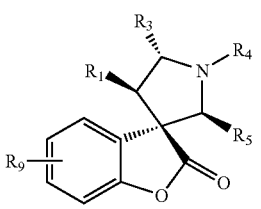
wherein:
$R_1$, $R_3$, $R_4$, $R_5$ and $R_9$ are as defined above.
In a further embodiment, the compounds of Formula I have Formula LXV:
LXV
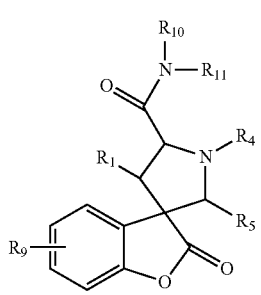
wherein:
$R_1$, $R_4$, $R_5$, $R_9$, $R_{10}$, and $R_{11}$ are as defined above.

In a further embodiment, the compounds of Formula I have one of Formulae LXVI and LXVII:
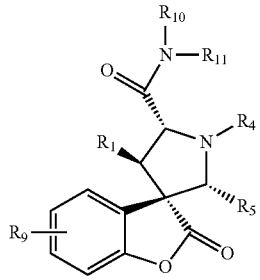
LXVI
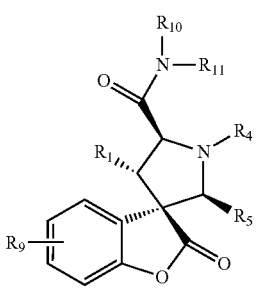
LXVII
wherein:
$R_1$, $R_4$, $R_5$, $R_9$, $R_{10}$, and $R_{11}$ are as defined above.
Particular embodiments of the present invention include, without limitation, any one of the following compounds:
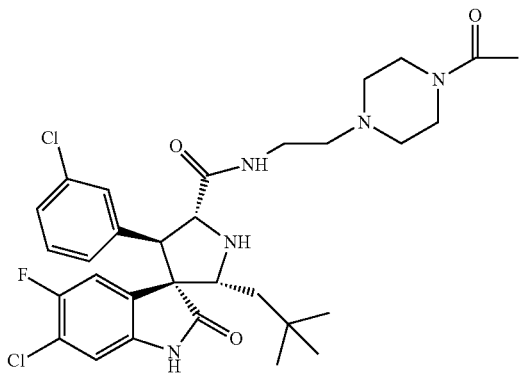
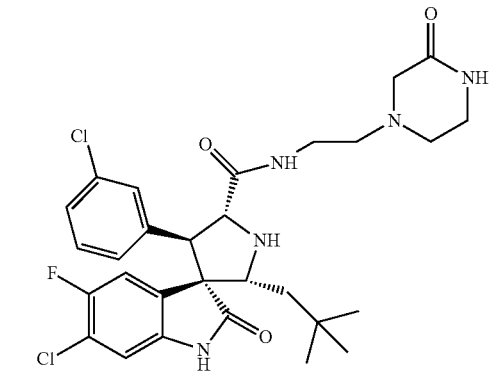
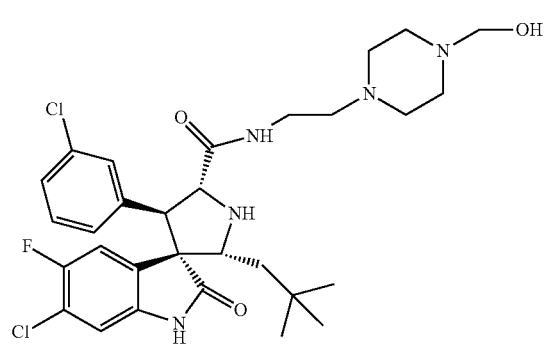
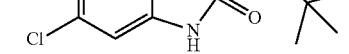
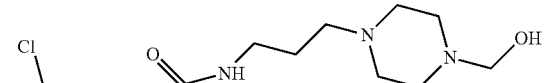
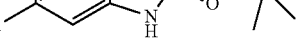
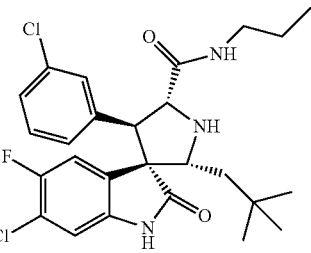

-continued
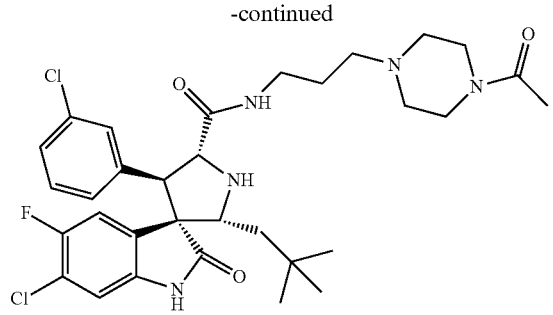
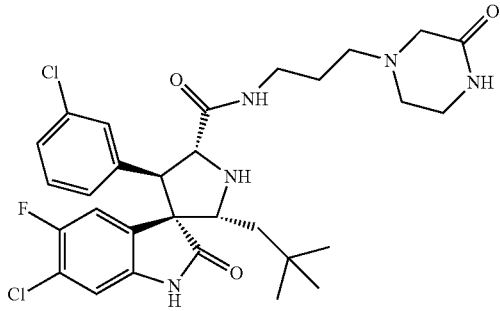
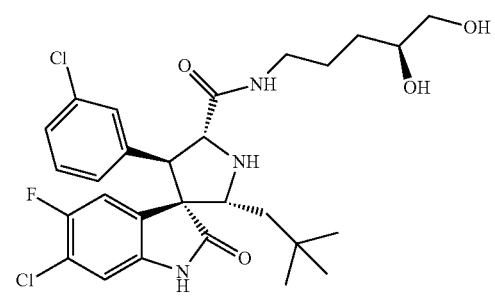
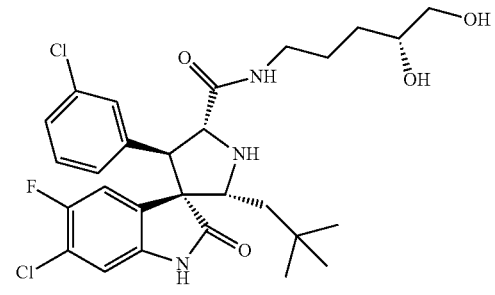
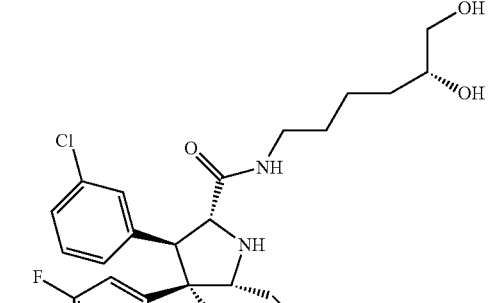
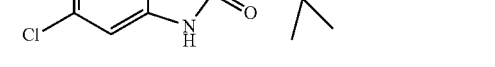
-continued
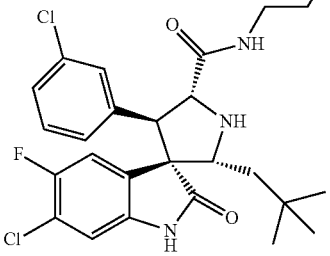
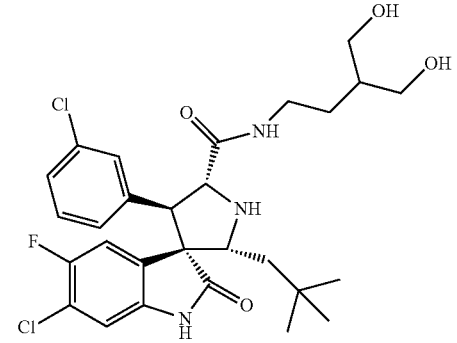
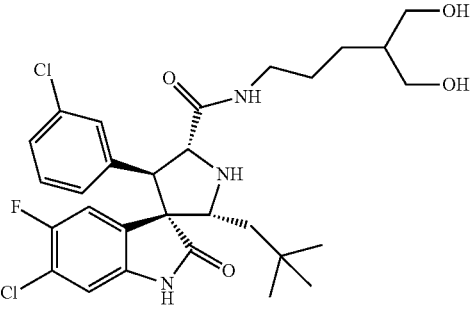
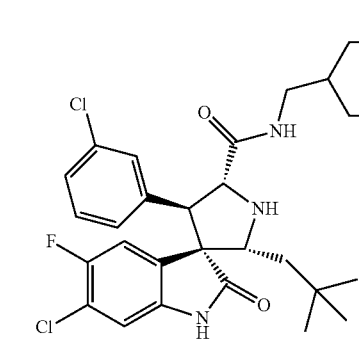
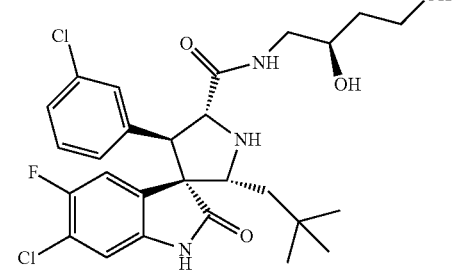

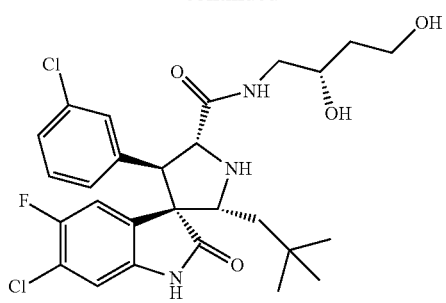
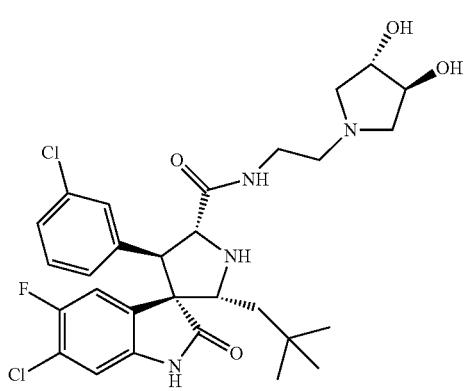
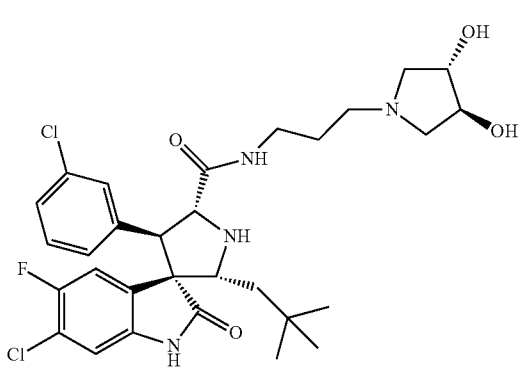
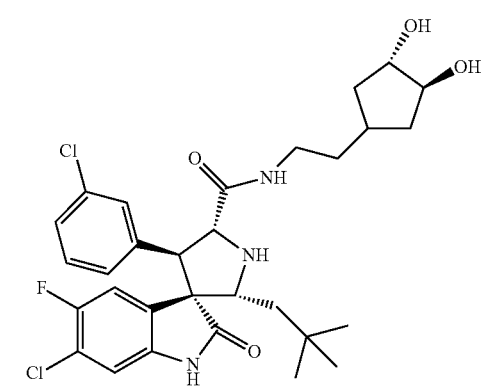
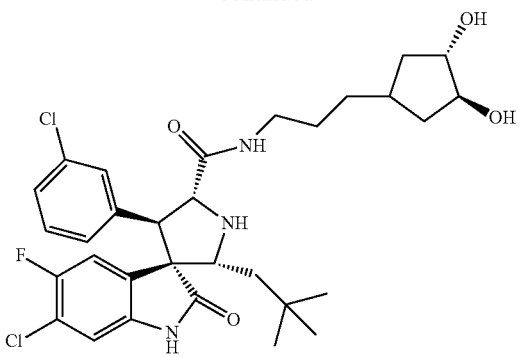
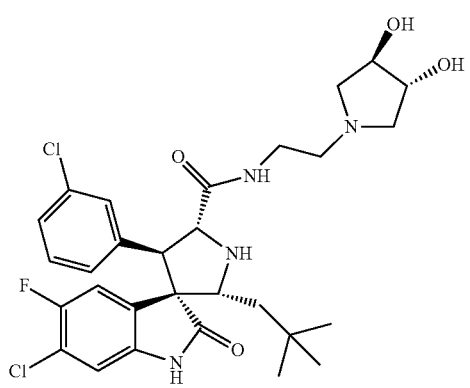
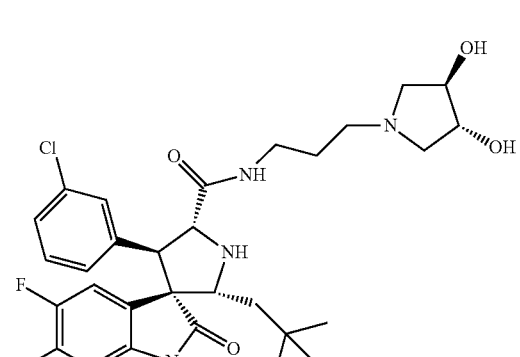
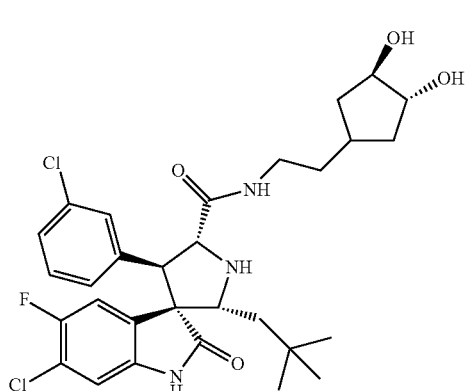

25
-continued
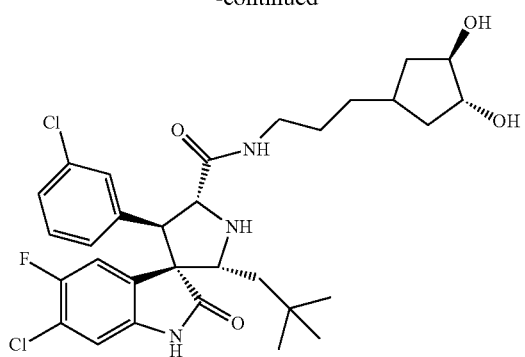
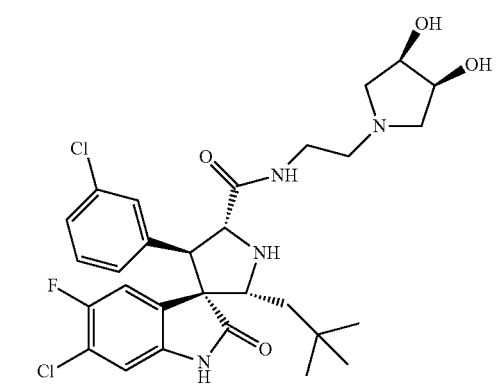
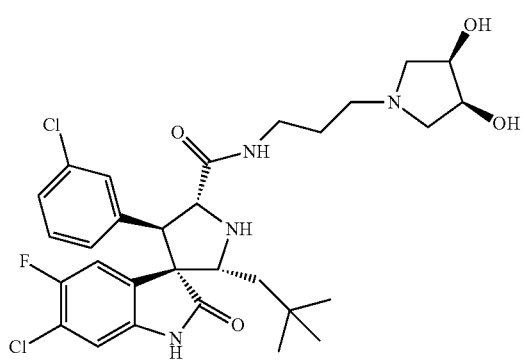
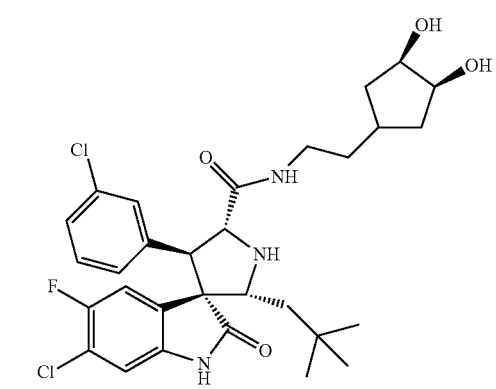
26
-continued
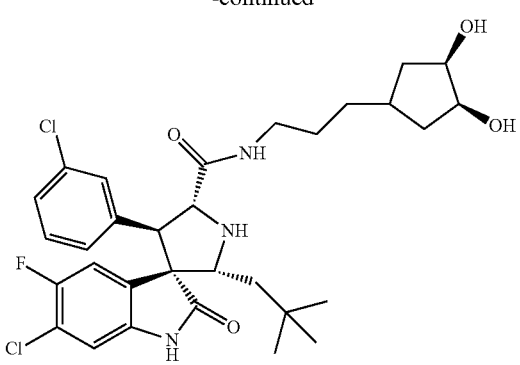
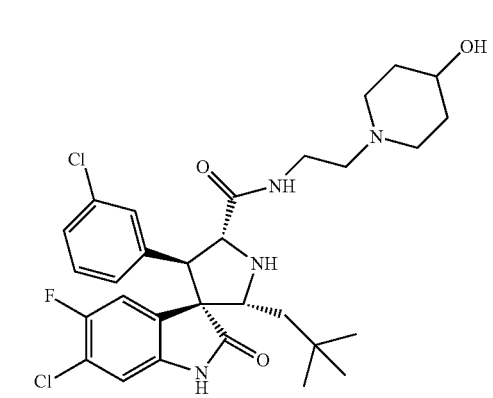
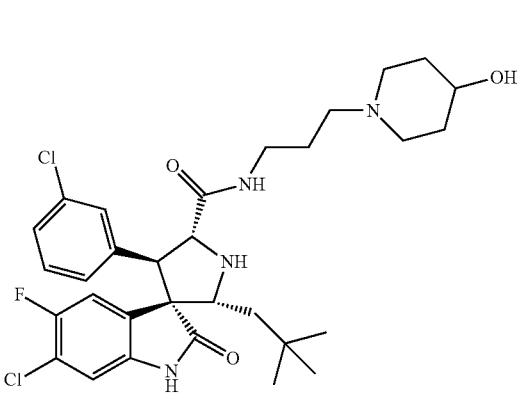
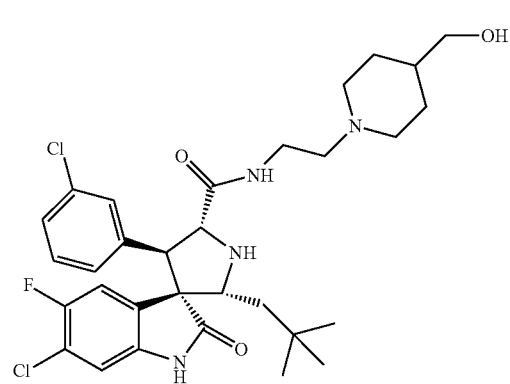

27
-continued
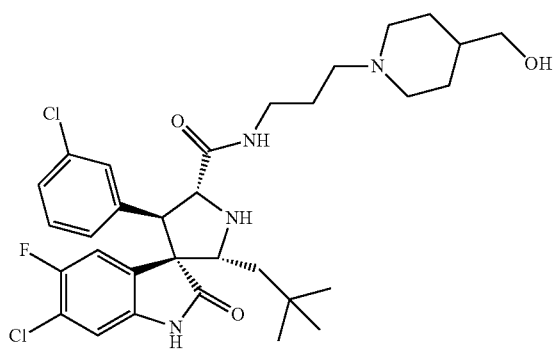
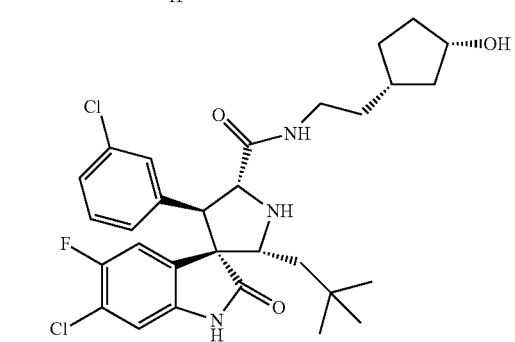
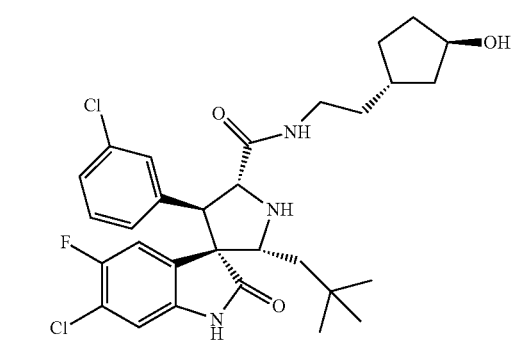
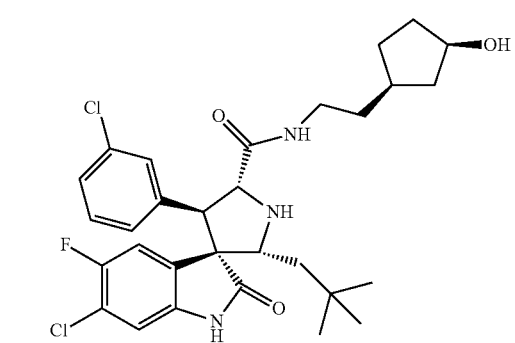
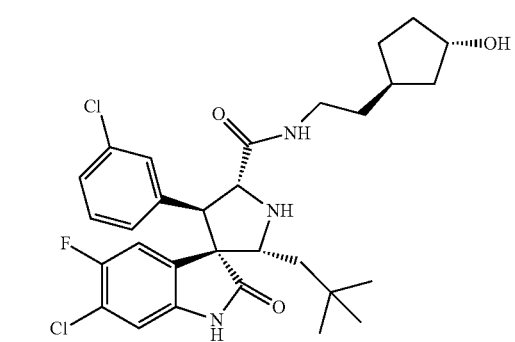
28
-continued
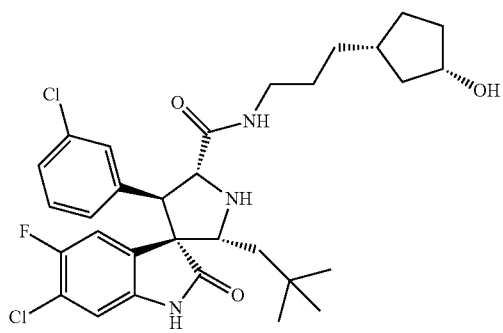
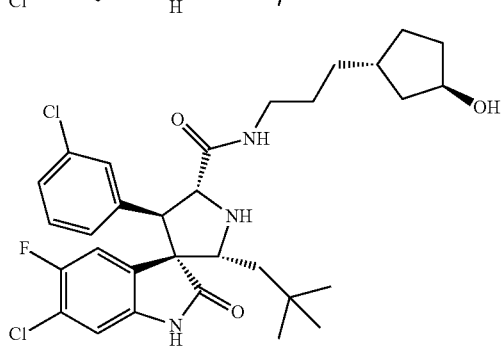
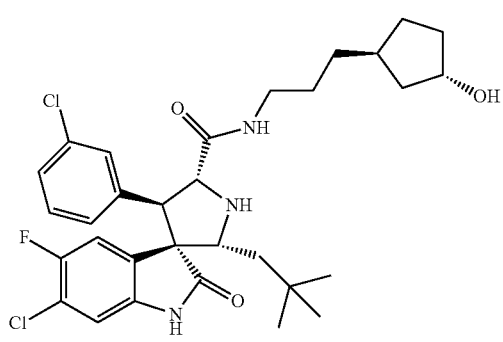
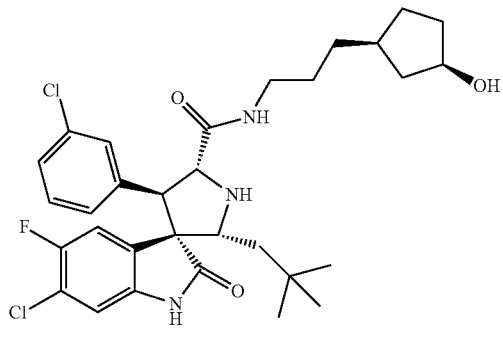
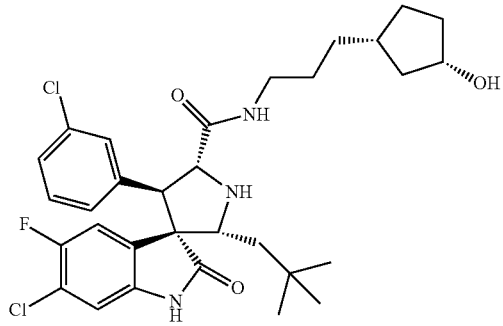

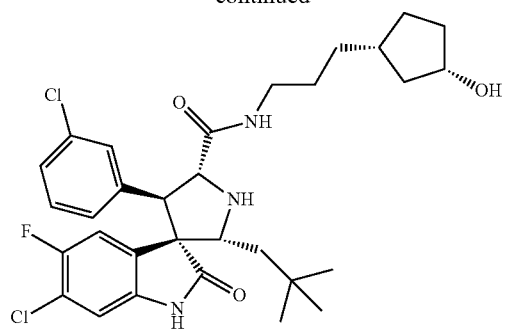
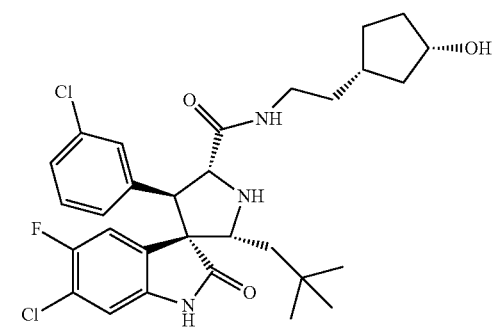
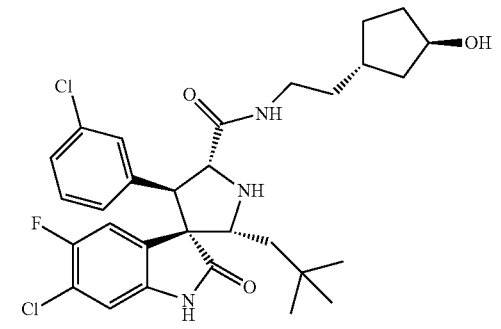
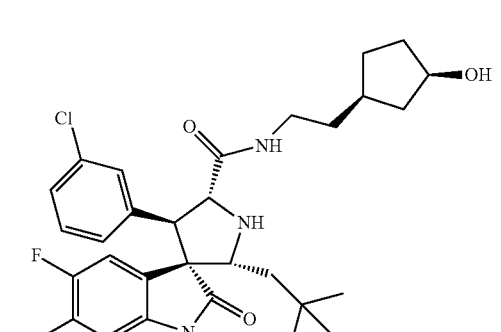
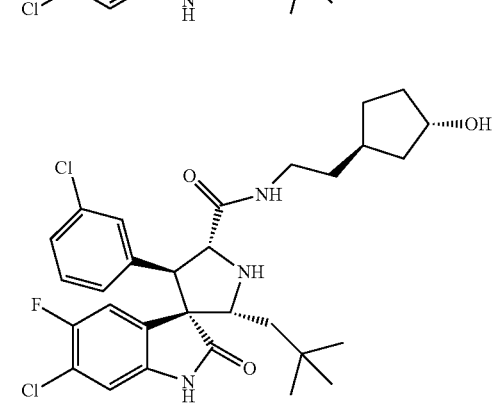
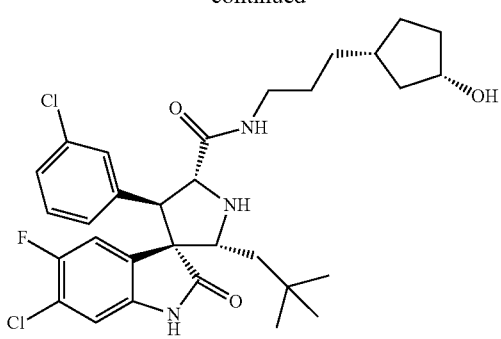
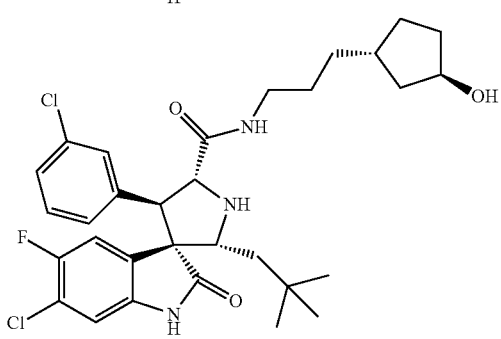
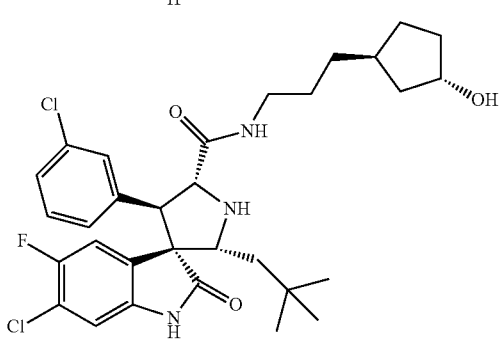
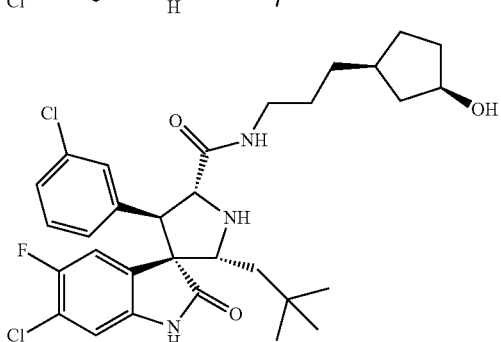
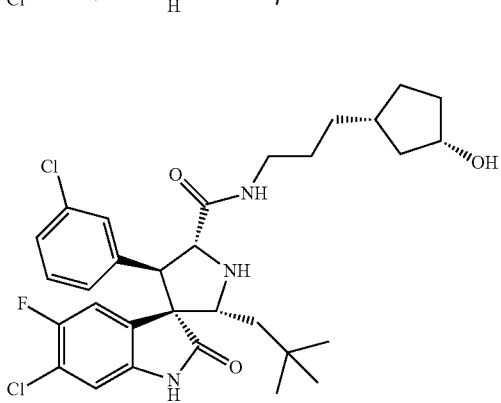

| 31 -continued | 32 -continued |
|---|---|
| 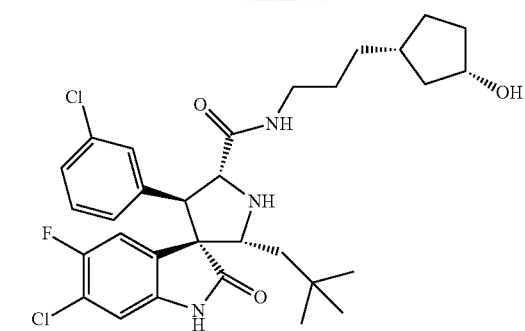 | 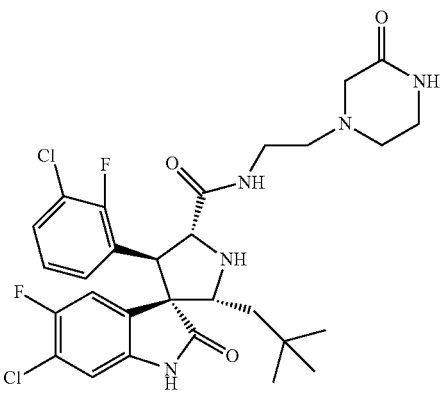 |
| 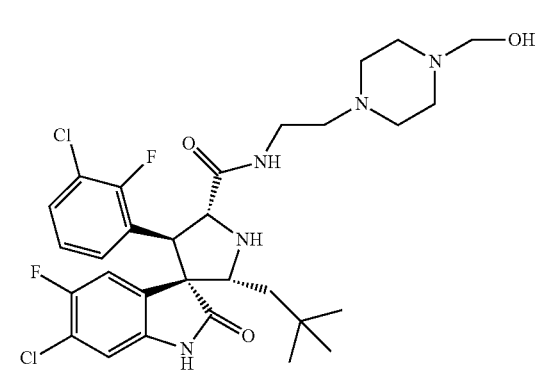 | 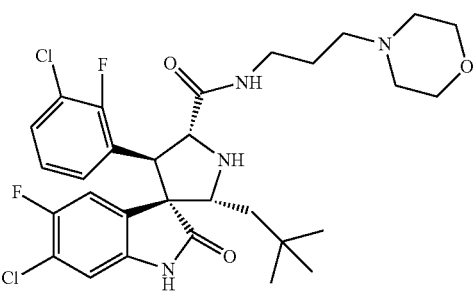 |
| 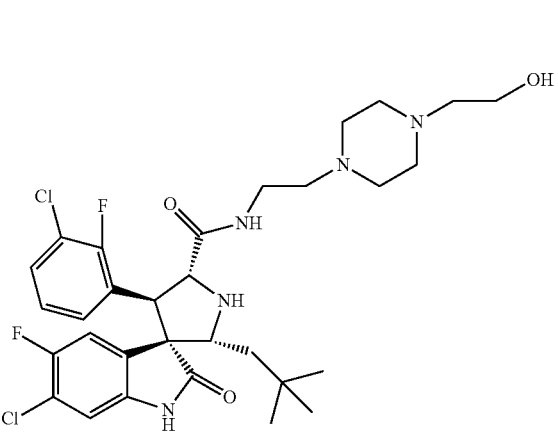 | 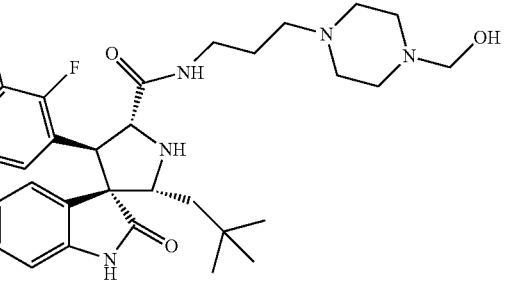 |
| 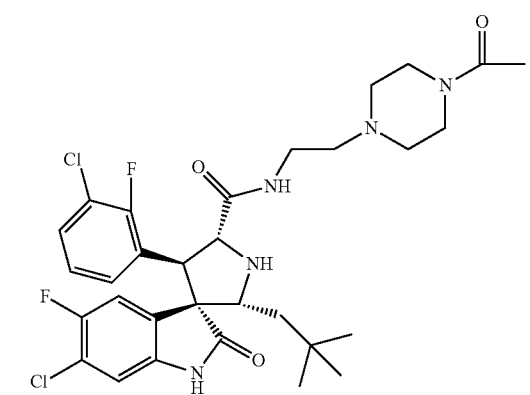 | 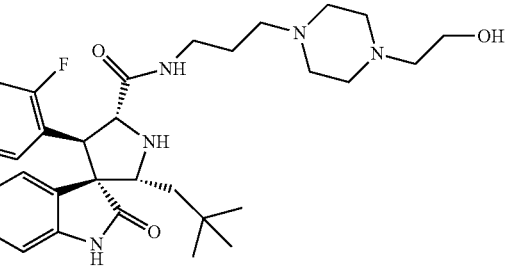 |
| | 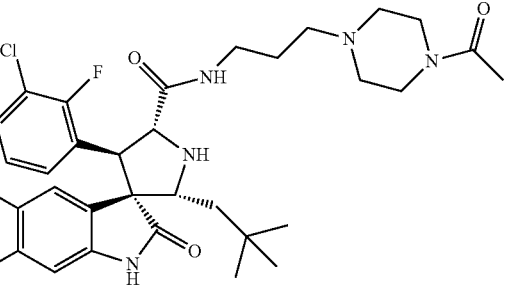 |

33
-continued
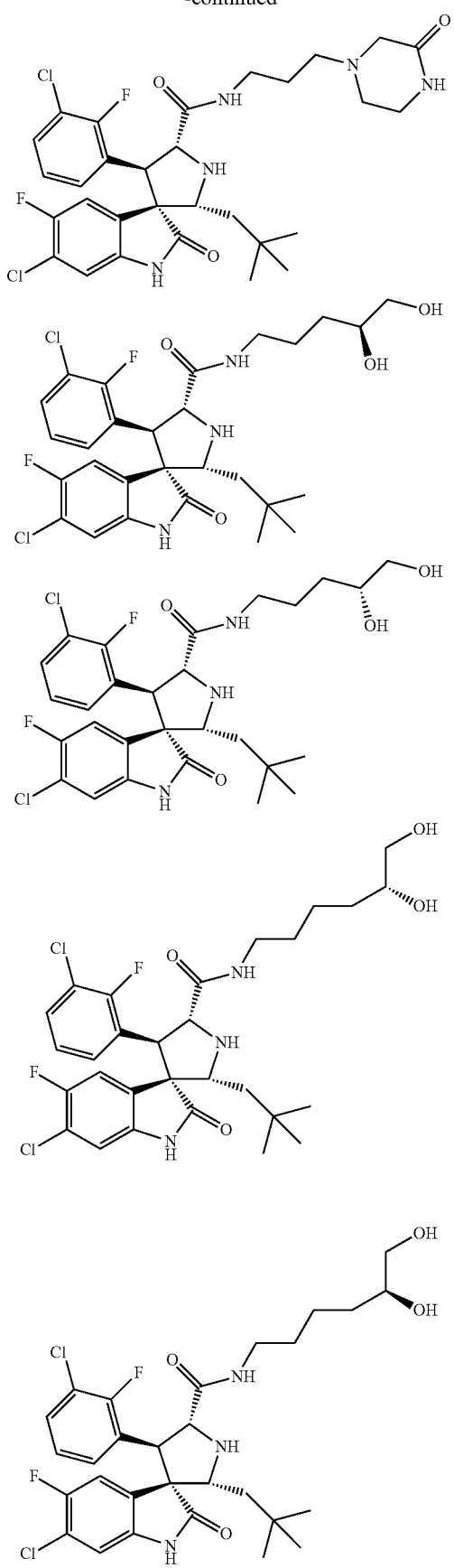
34
-continued
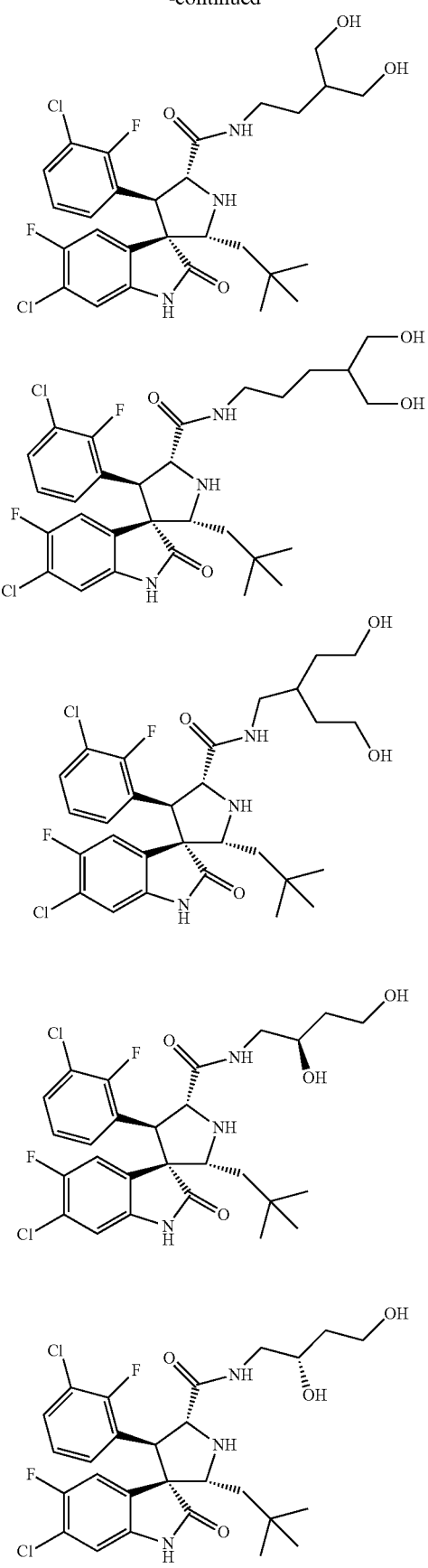

35
-continued
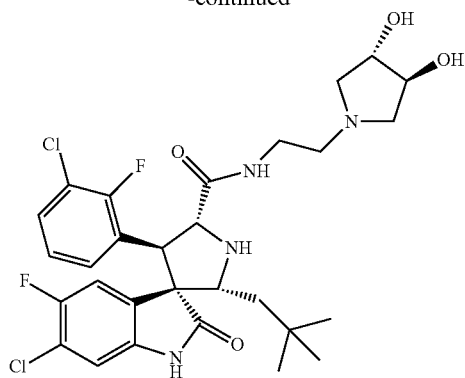
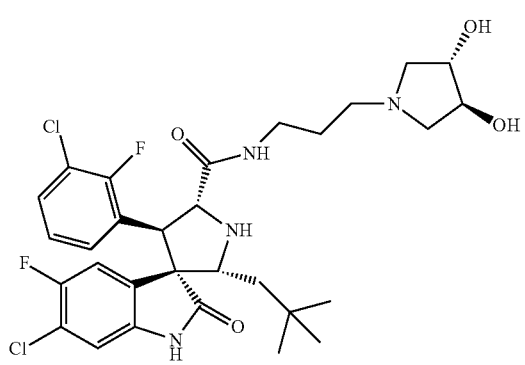
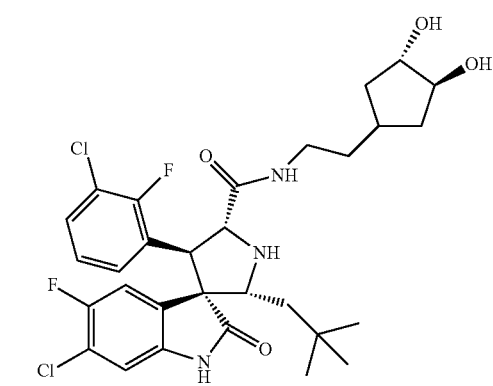
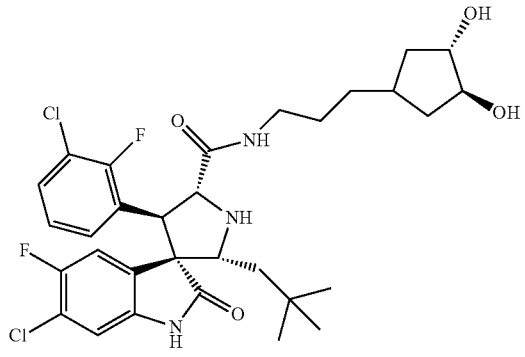
36
-continued
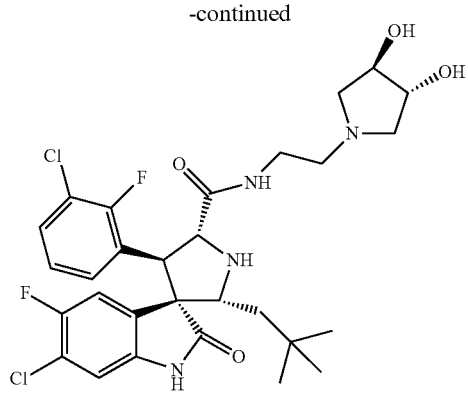
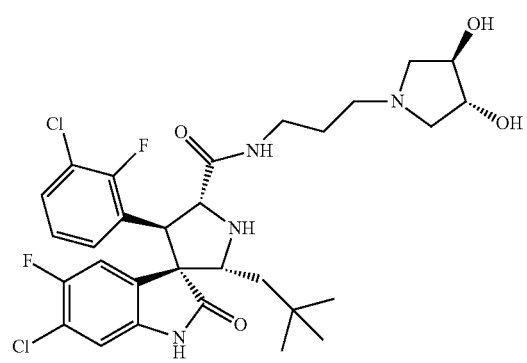
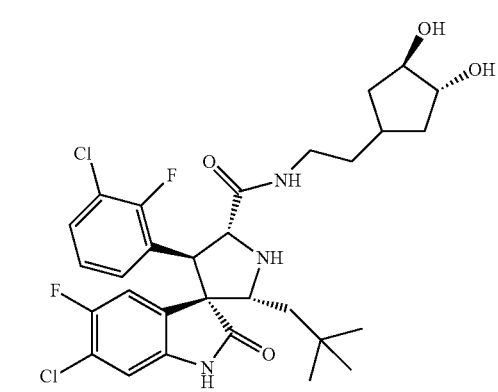
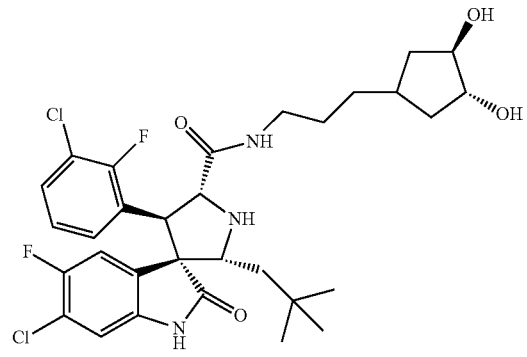

37
-continued
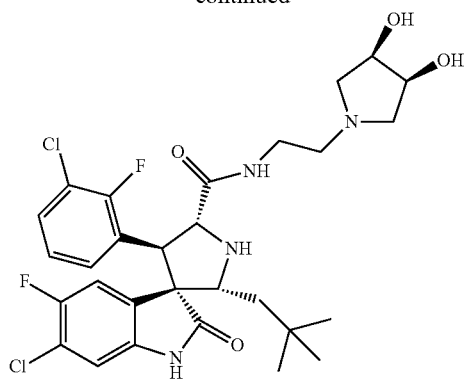
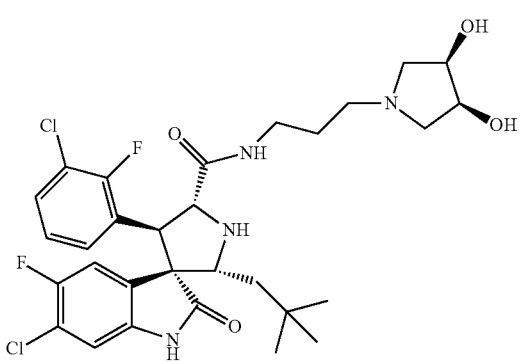
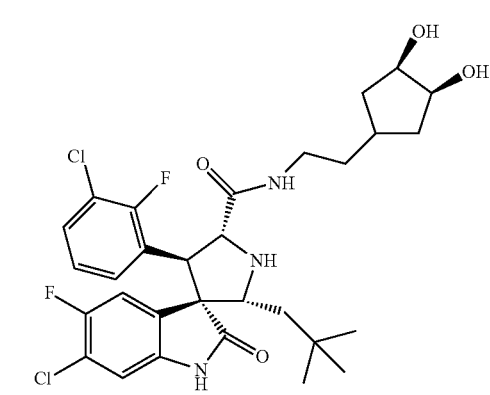
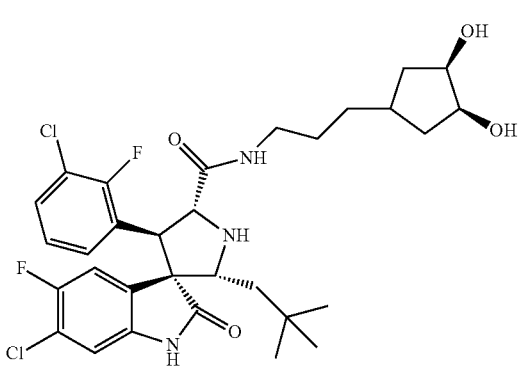
38
-continued
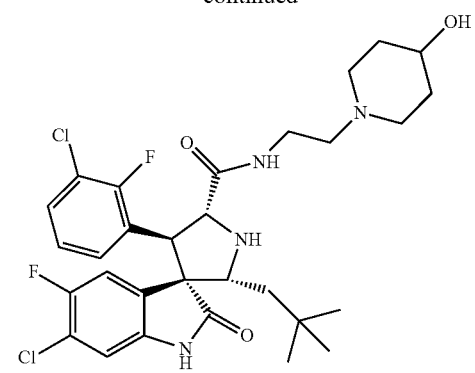
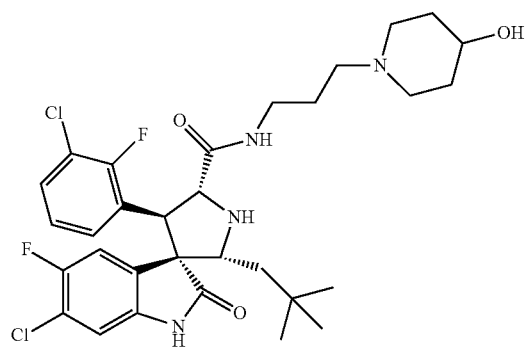
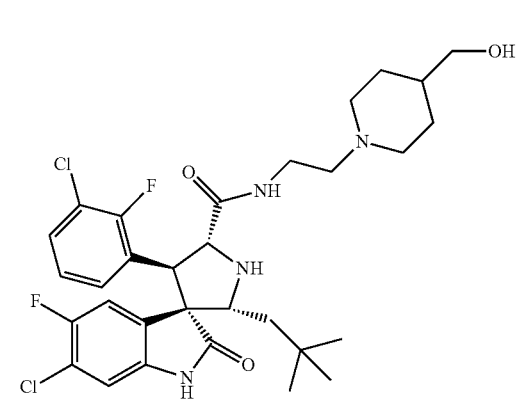
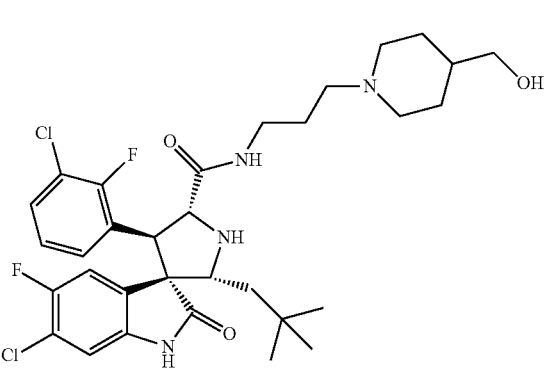

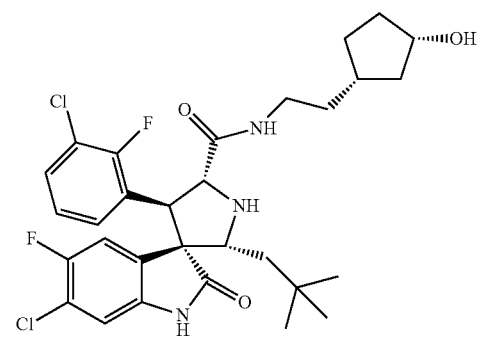
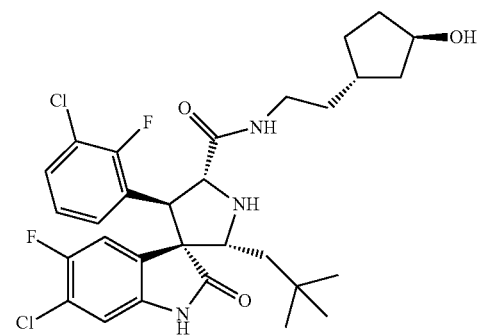
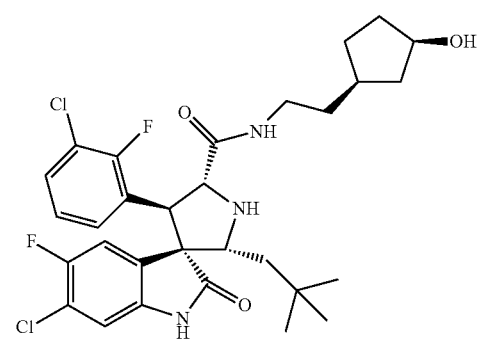
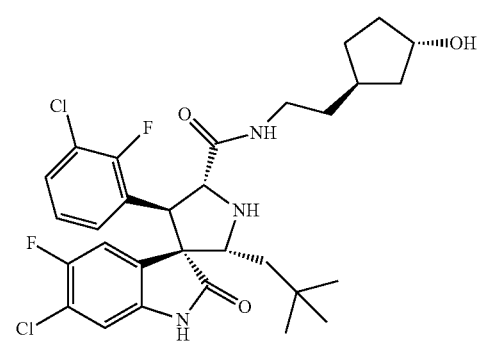
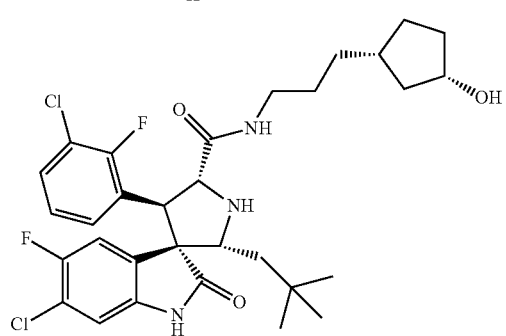
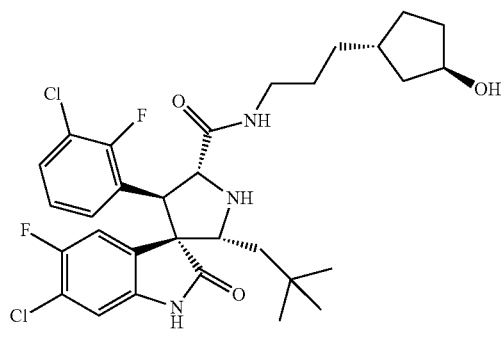
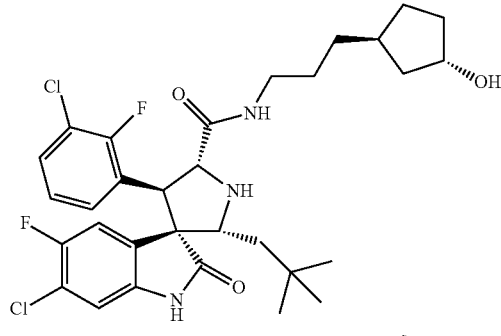
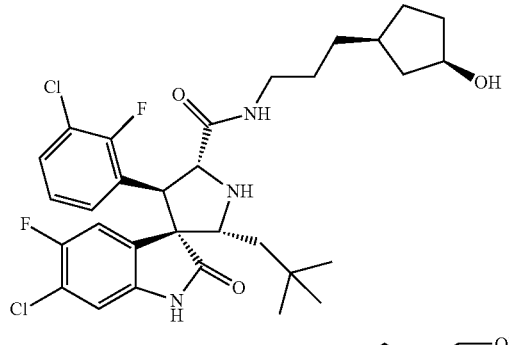
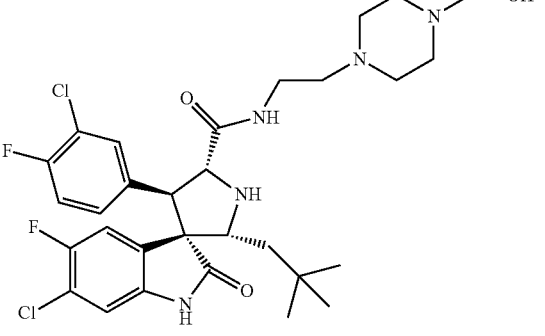
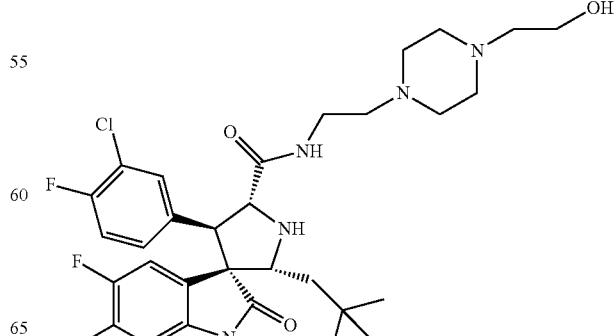

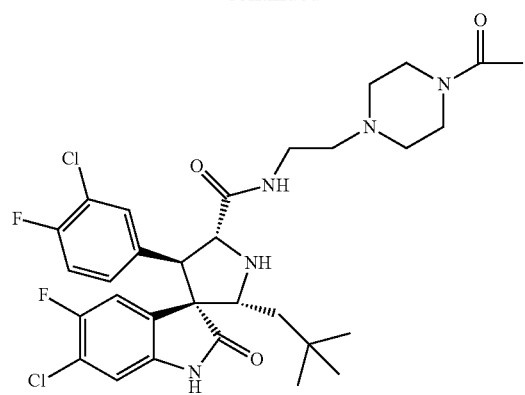
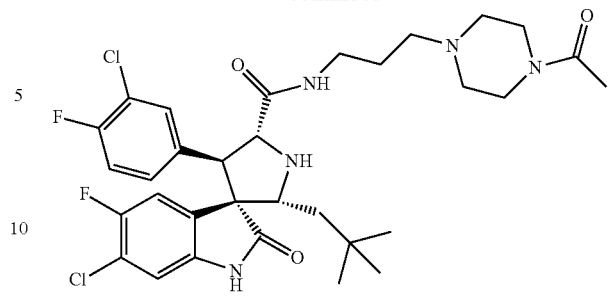
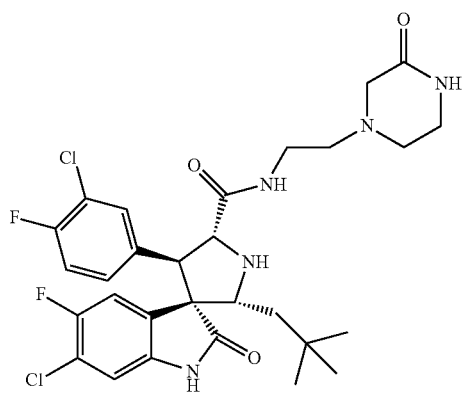
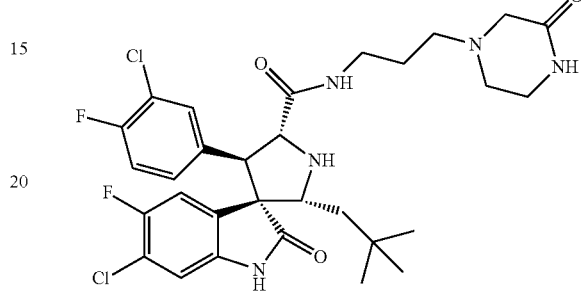
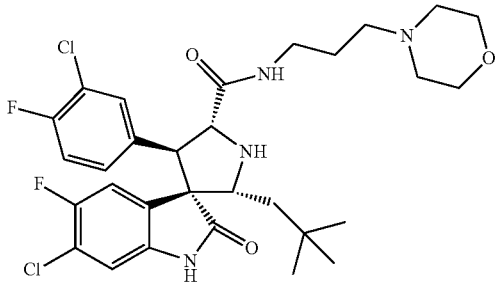
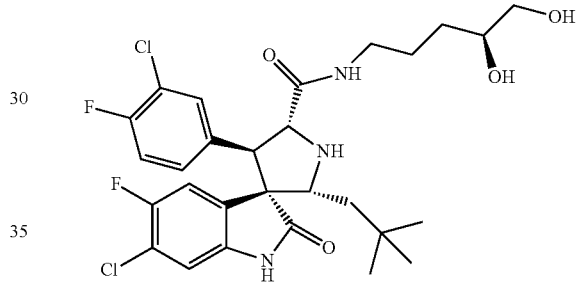
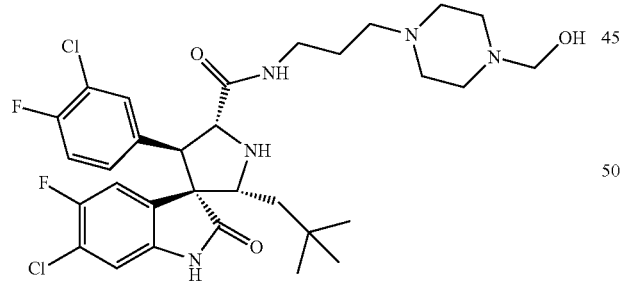
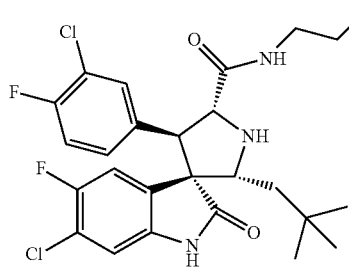
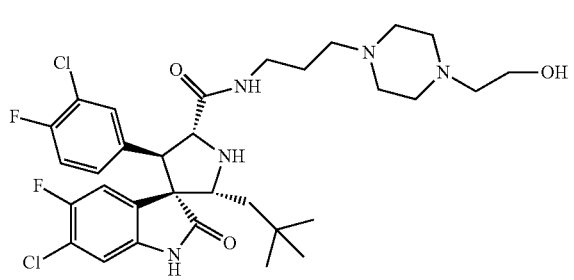
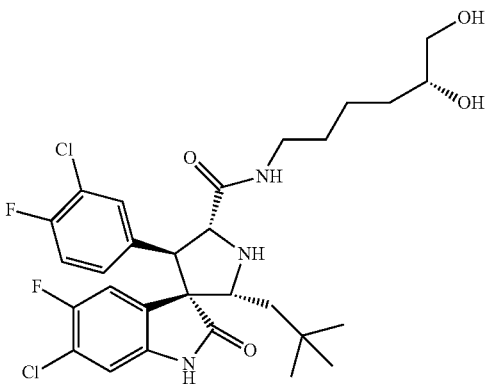

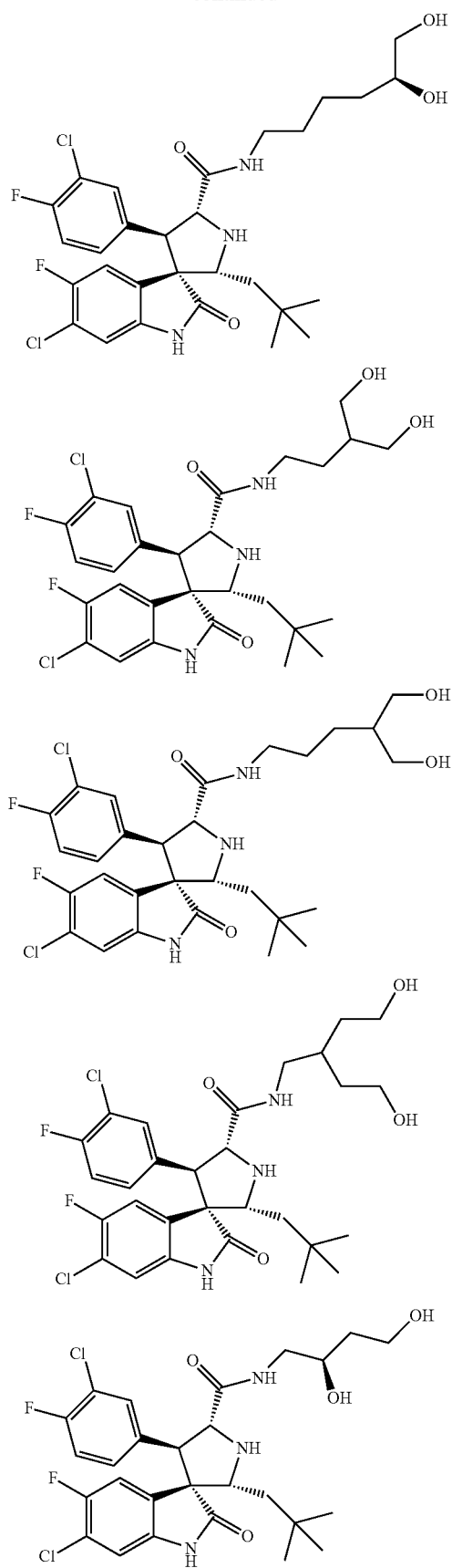
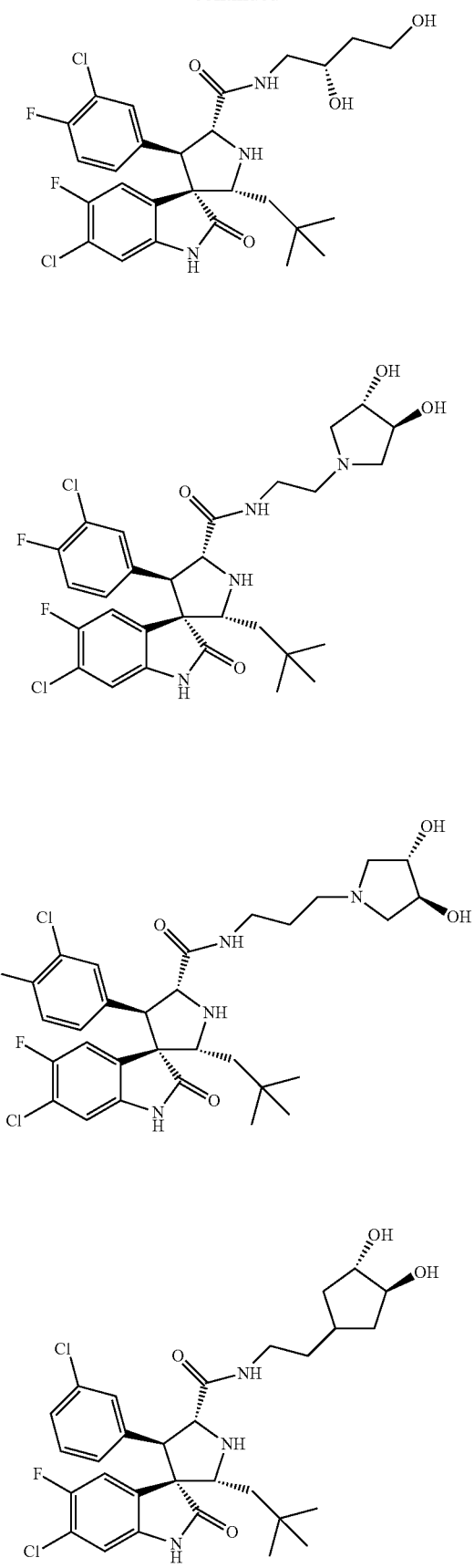

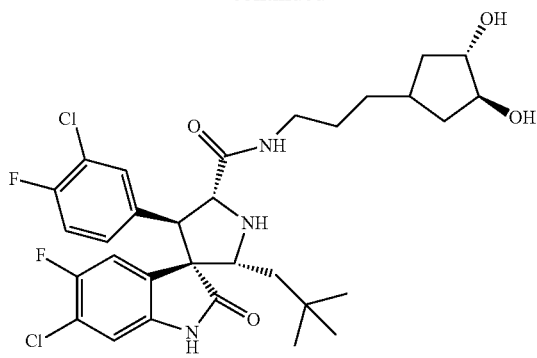
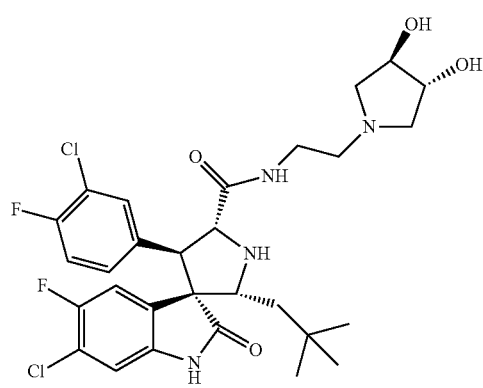
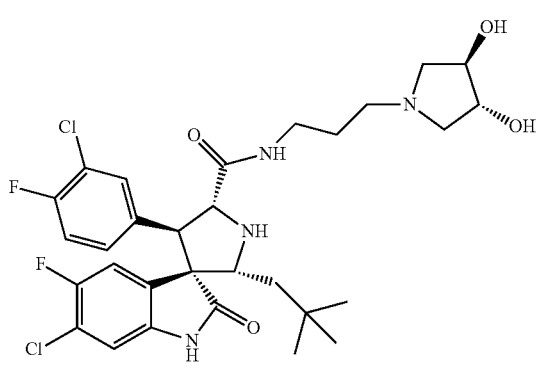
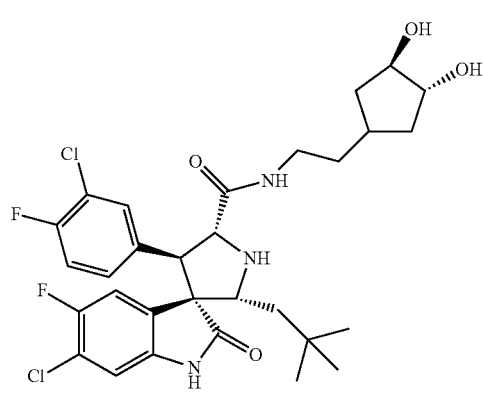
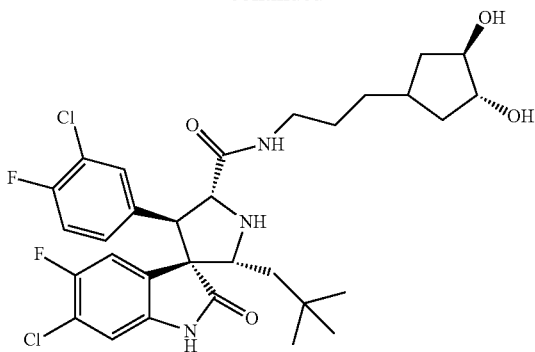
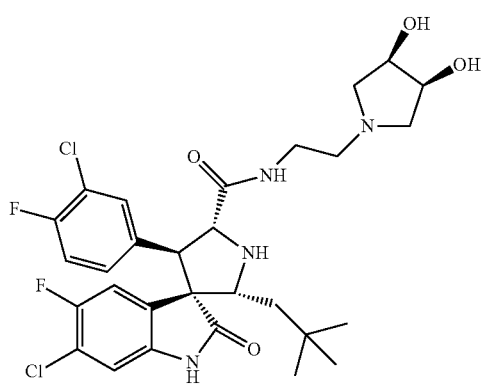
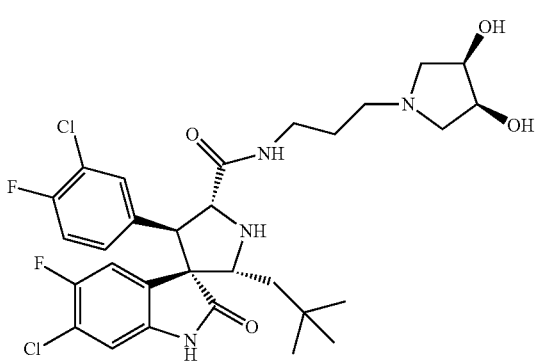
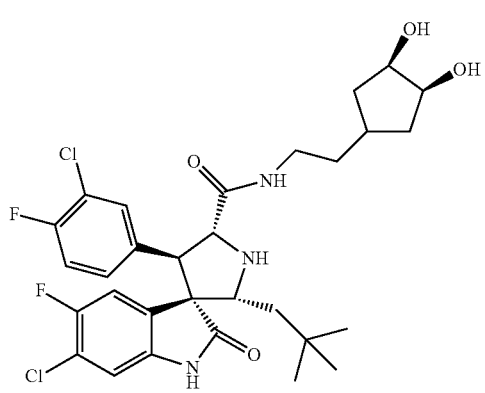

47
-continued
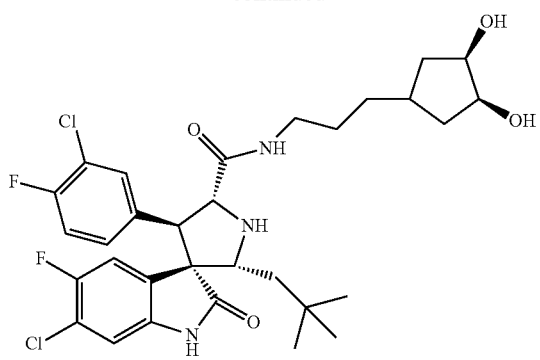
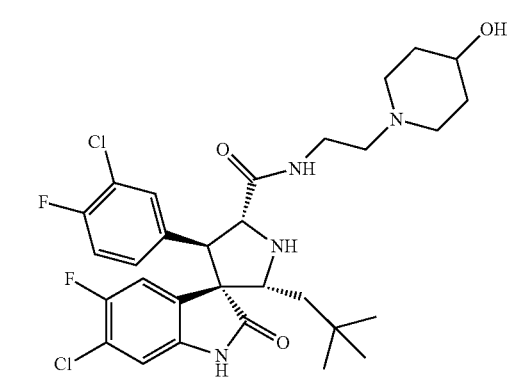
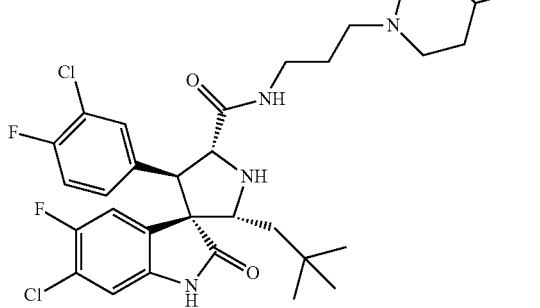
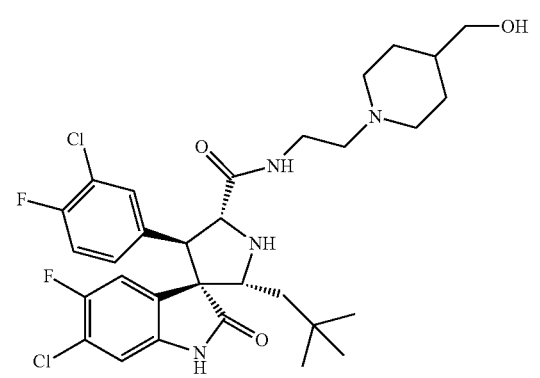
48
-continued
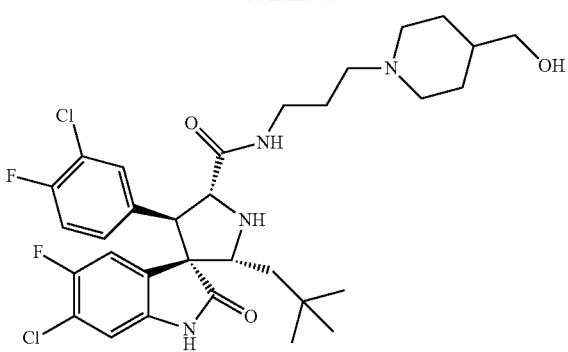
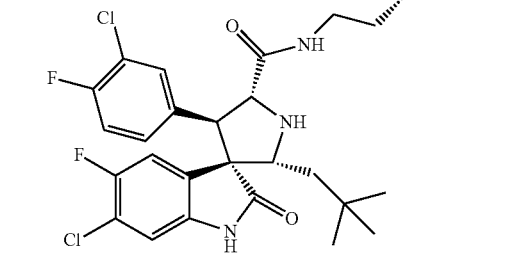
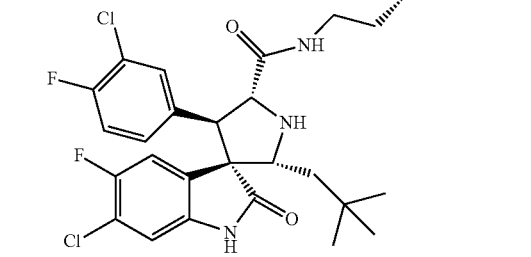
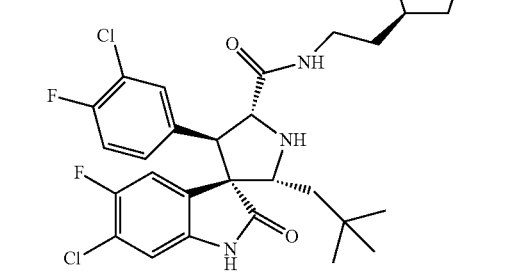
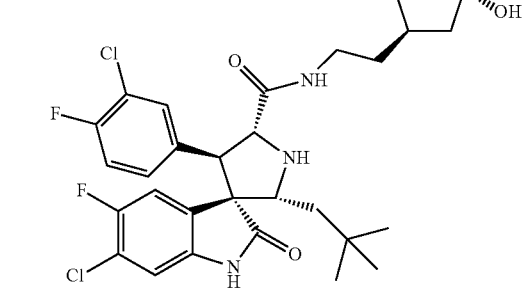

49
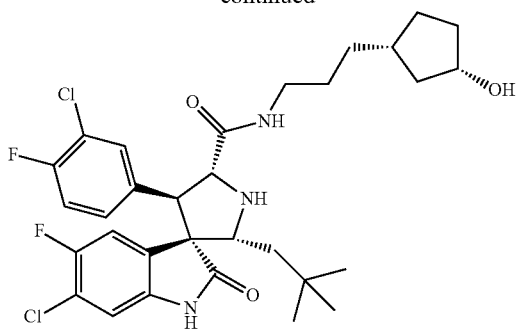
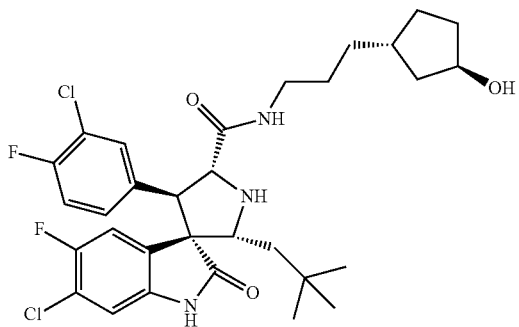
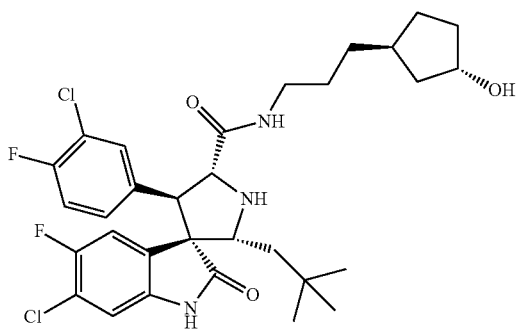
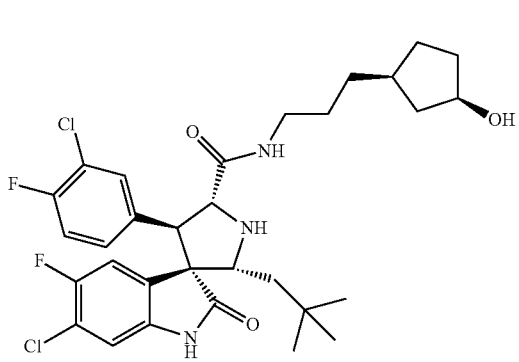
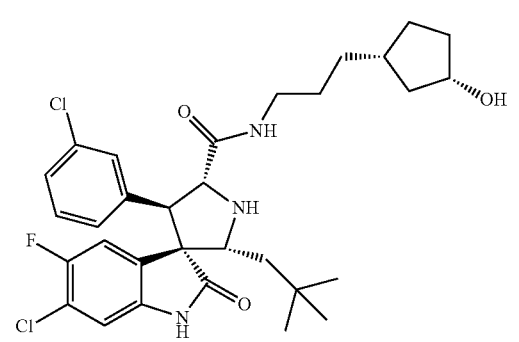
50
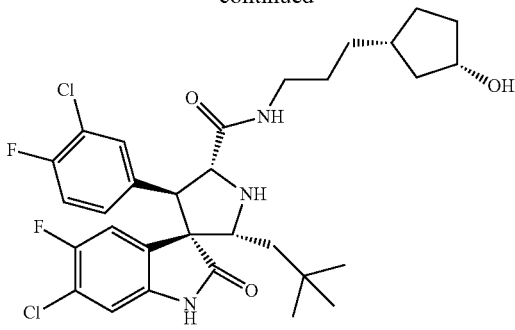
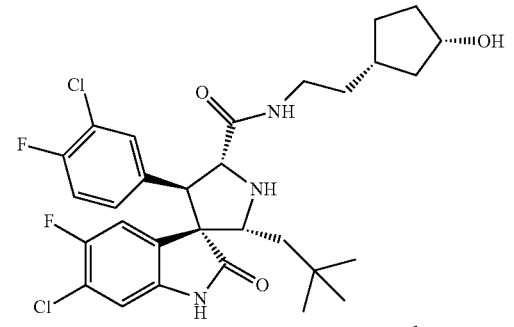
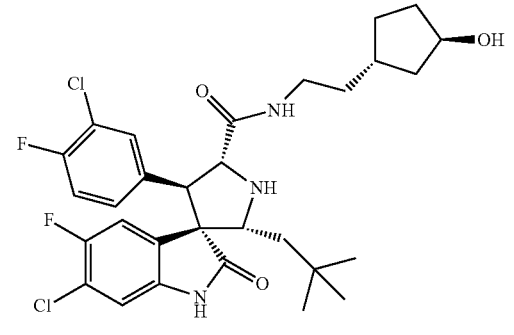
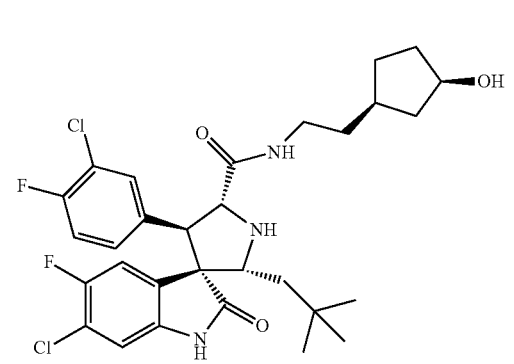
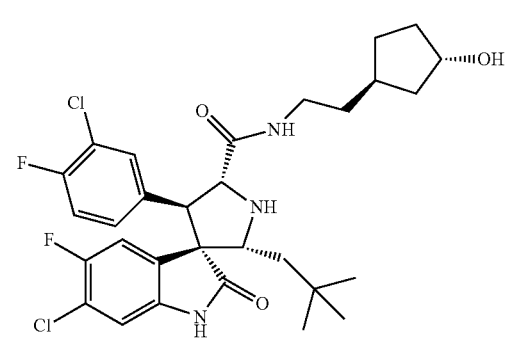

51
-continued
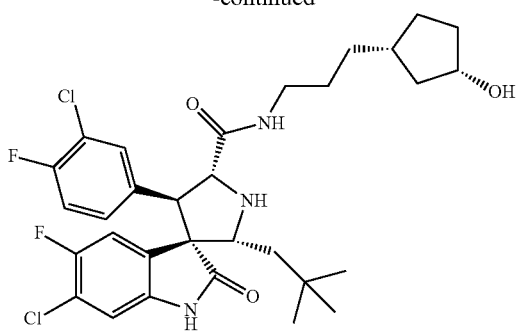
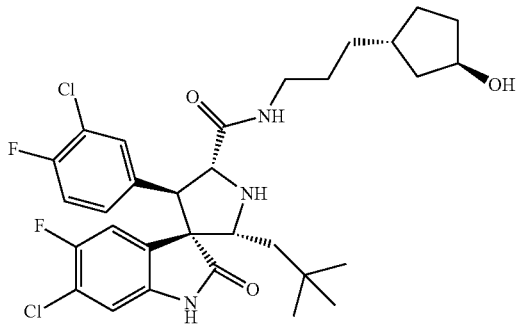
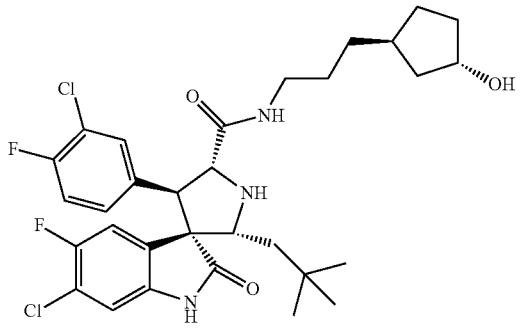
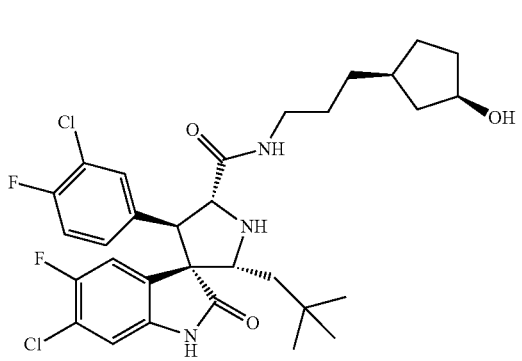
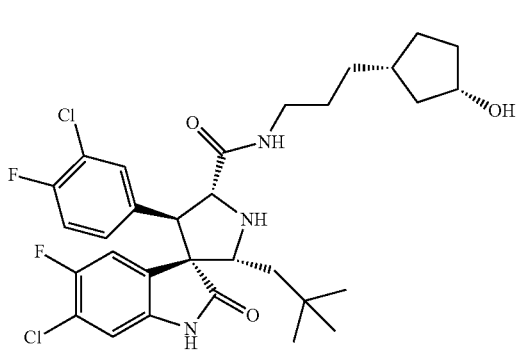
52
-continued
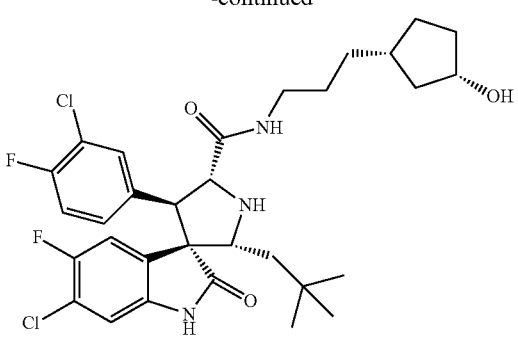
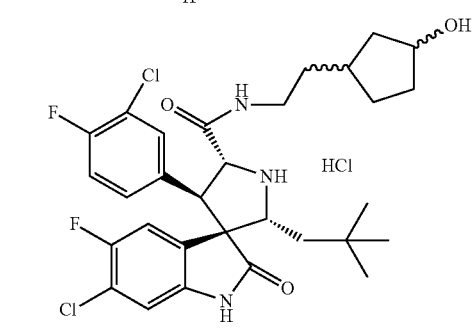
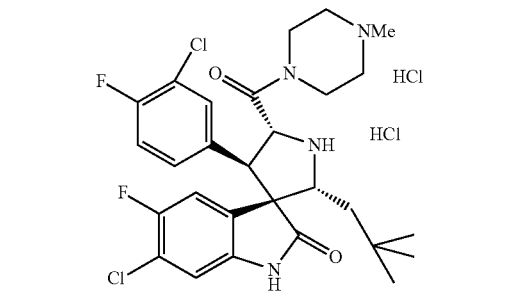
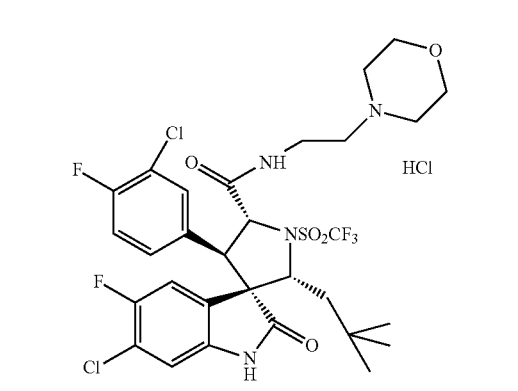
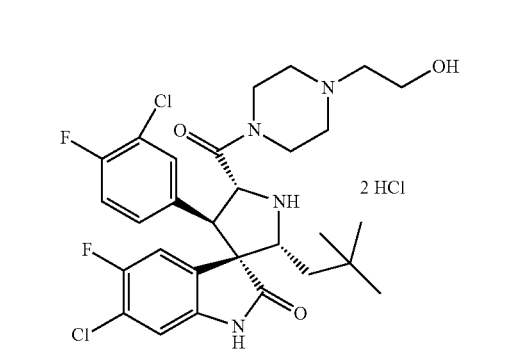

-continued
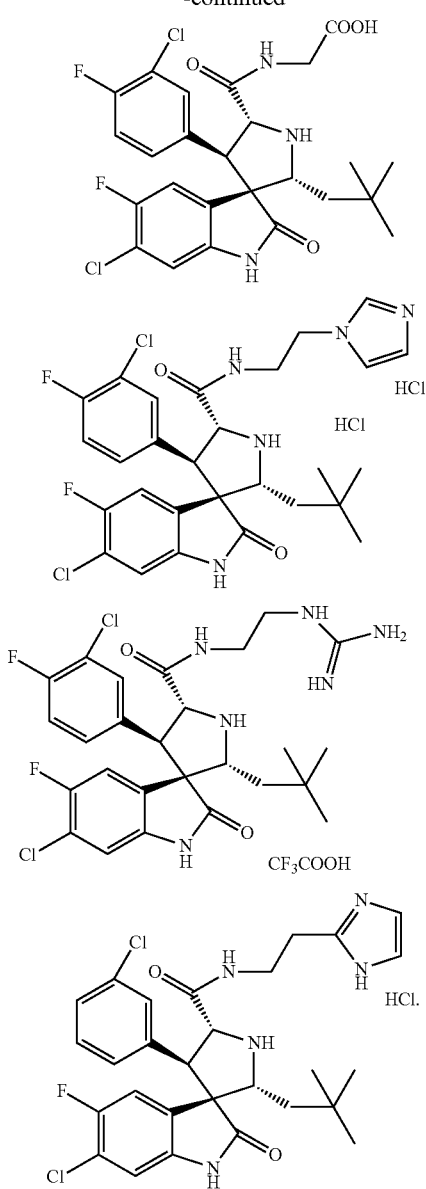
Another particular embodiment of the present invention includes, without limitation, any one of the following compounds:
-continued
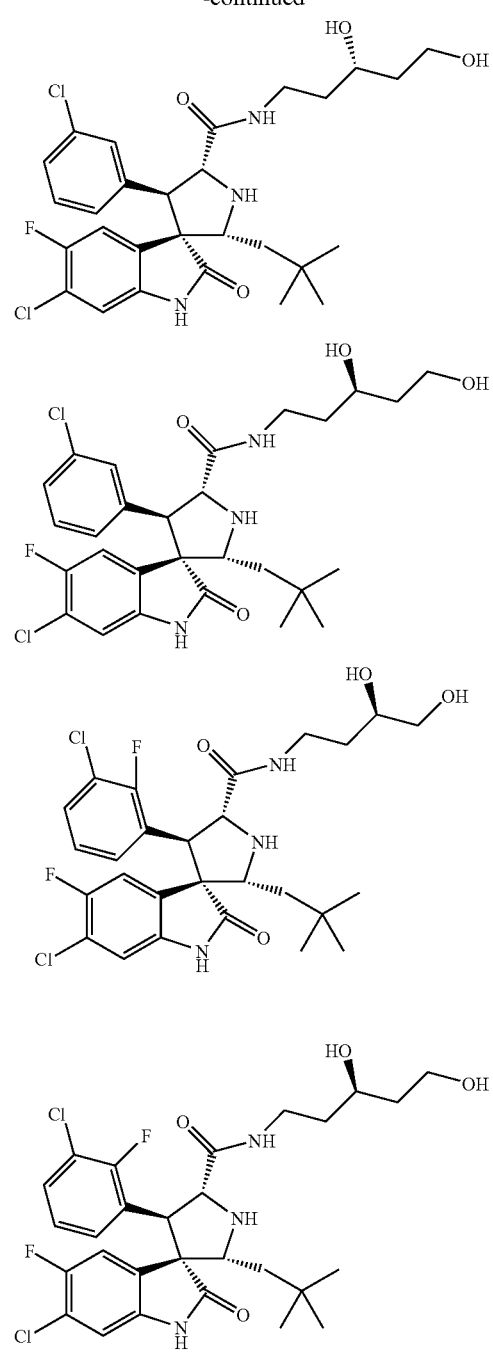

55
-continued
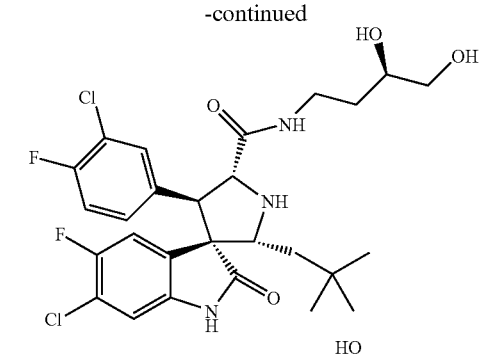
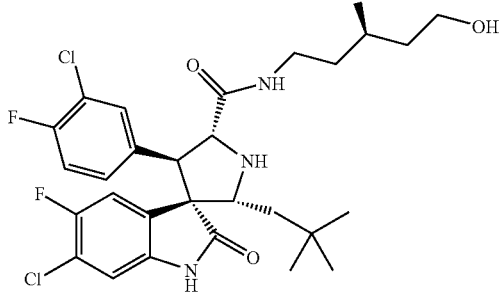
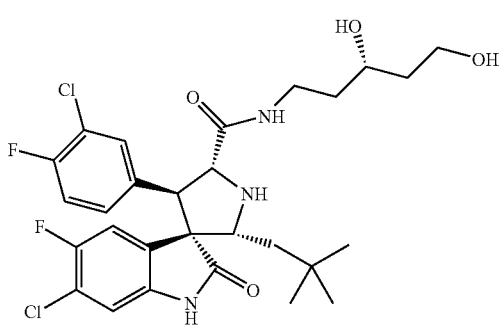
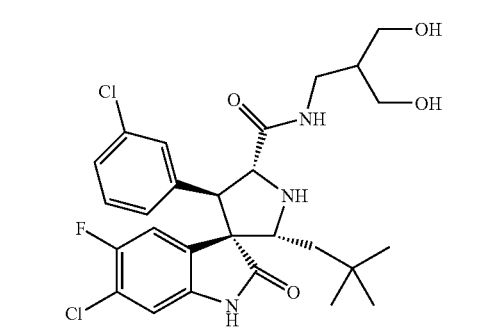
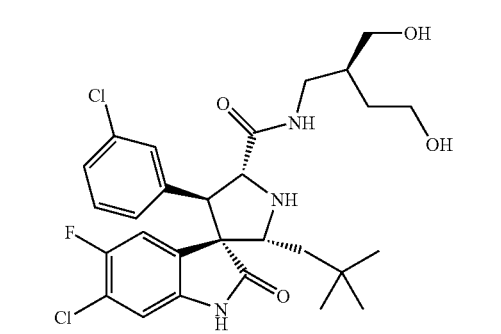
56
-continued
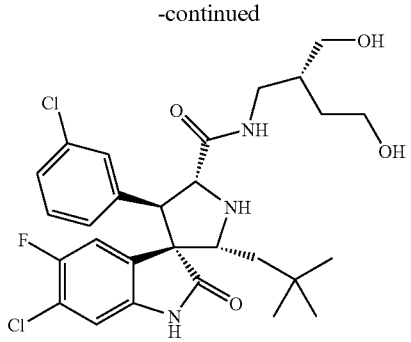
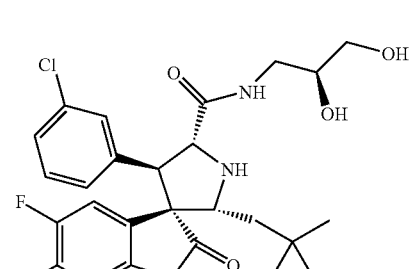
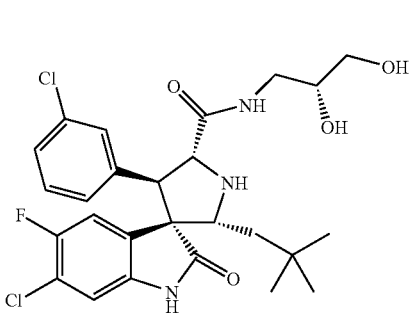
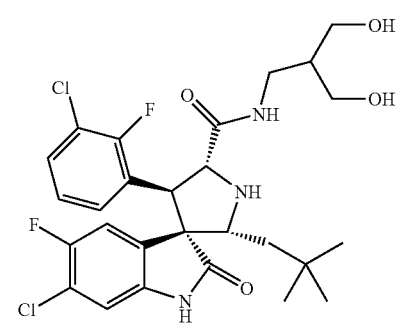
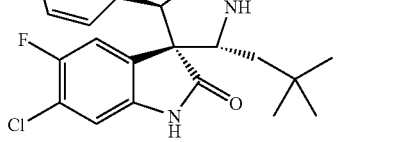

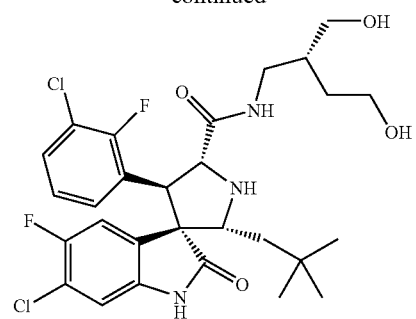
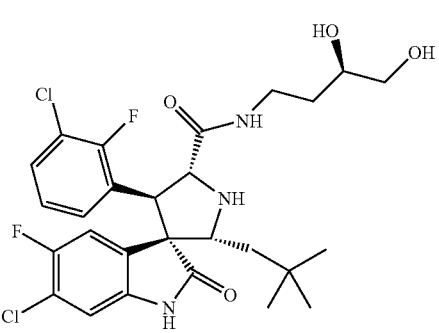
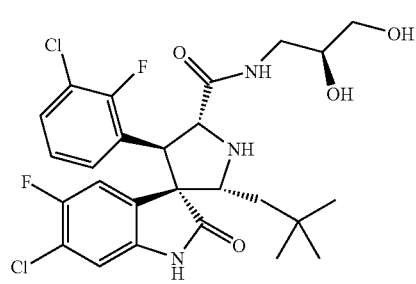
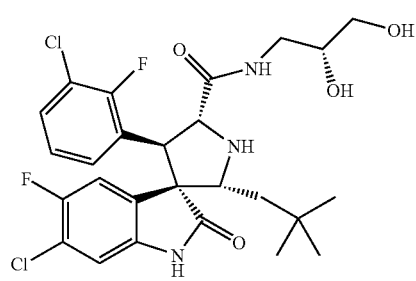
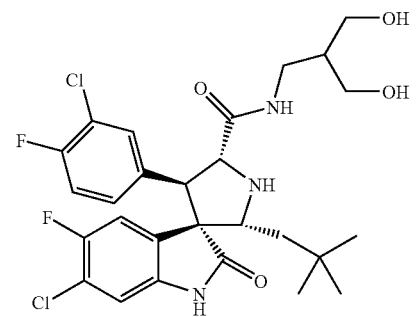
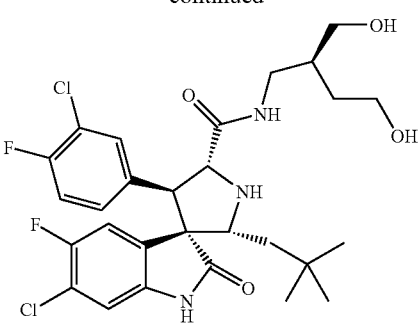
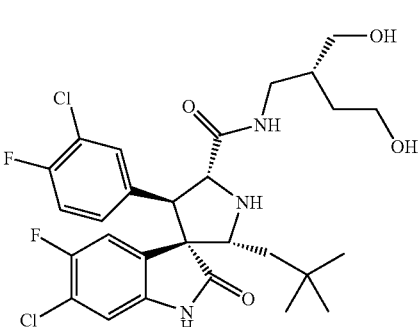
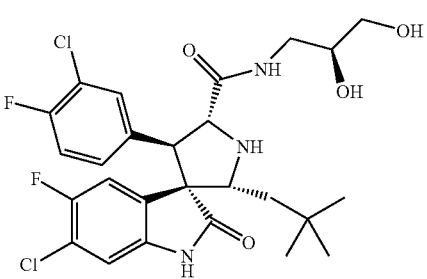
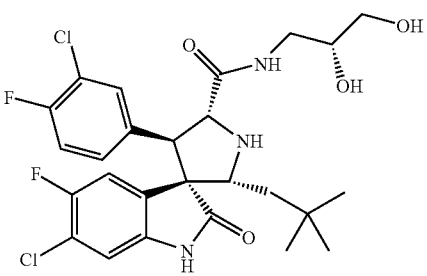
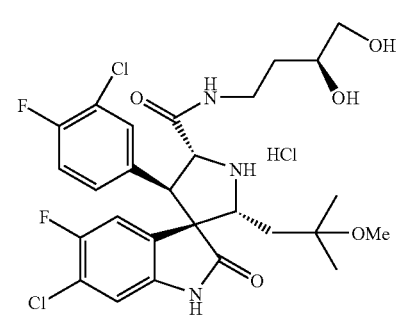

59
-continued
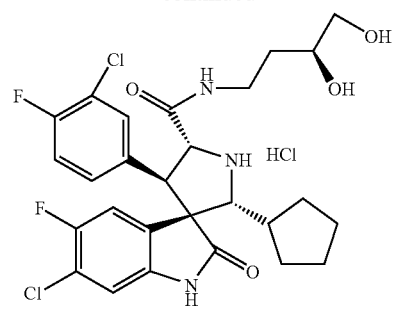
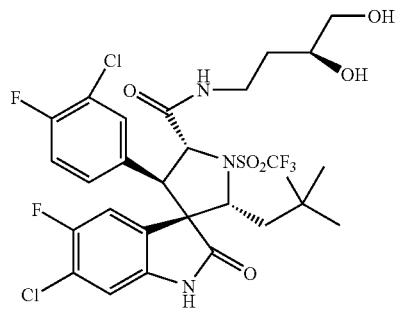
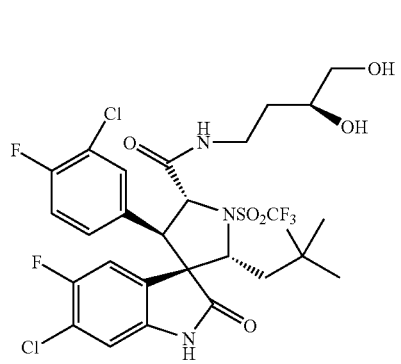
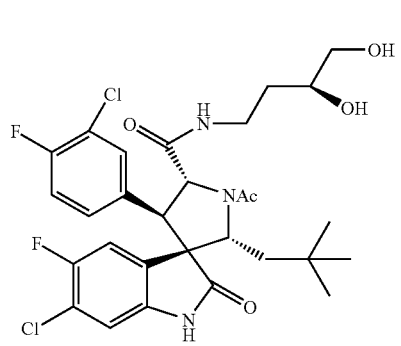
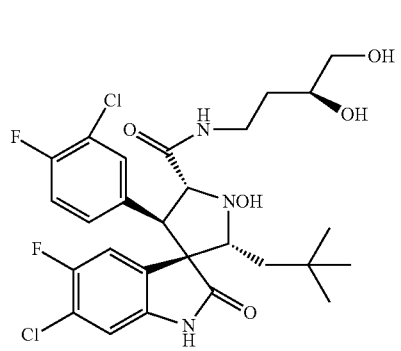
60
-continued
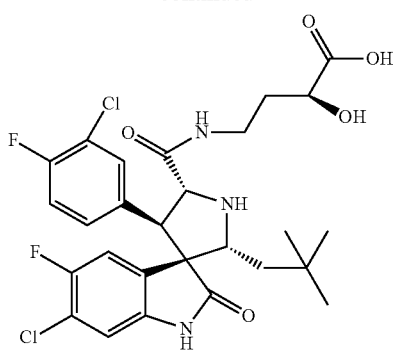
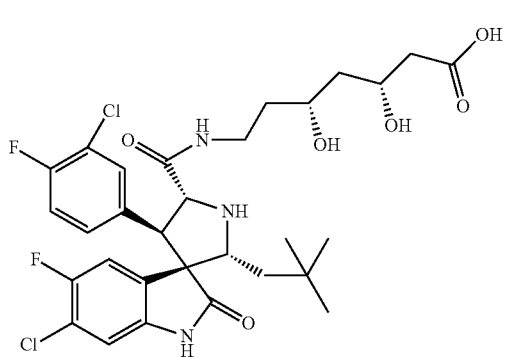
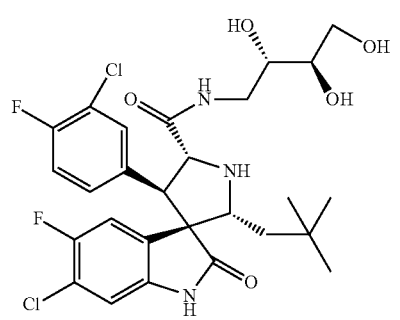
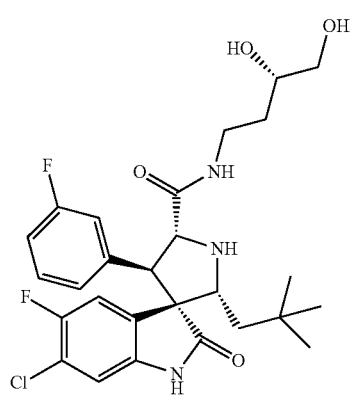

-continued

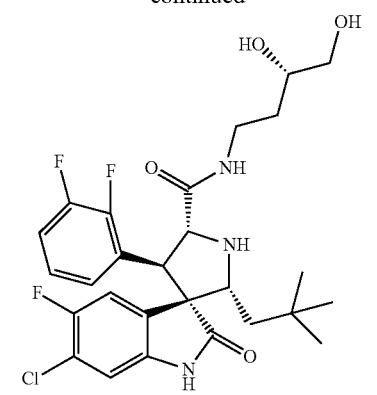

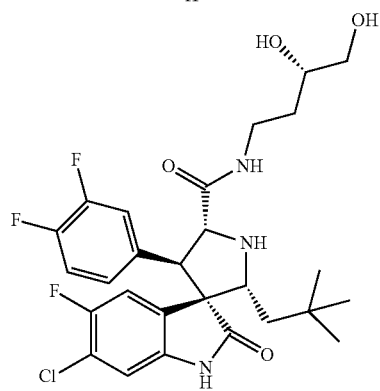

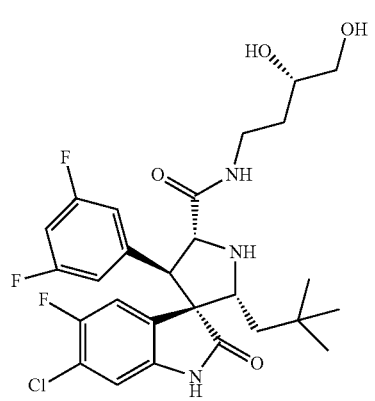

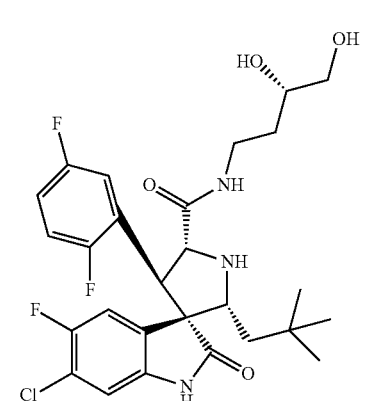

-continued

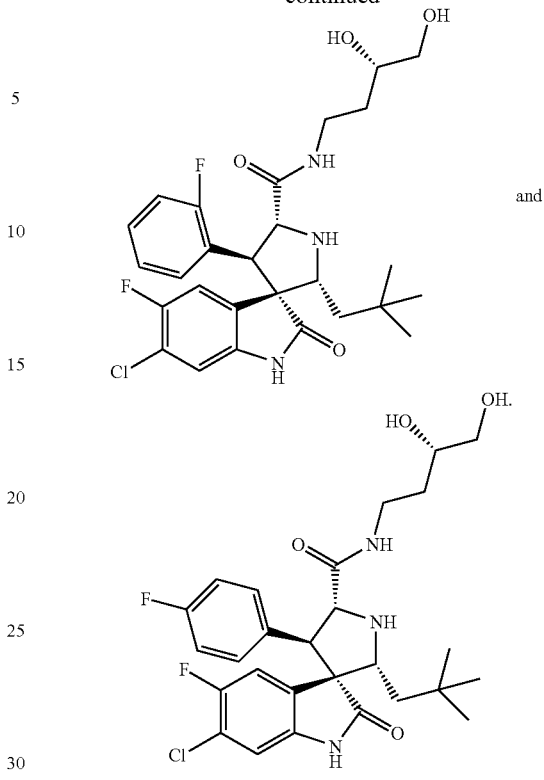

Useful alkyl groups include straight-chained or branched $C_{1-18}$ alkyl groups, especially methyl, ethyl, propyl, isopropyl, t-butyl, sec-butyl, 3-pentyl, adamantyl, norbornyl, and 3-hexyl groups.

Useful alkenyl groups include straight-chained or branched $C_{2-18}$ alkyl groups, especially ethenyl, propenyl, isopropenyl, butenyl, isobutenyl, and hexenyl.

Useful alkynyl groups are $C_{2-18}$ alkynyl groups, especially ethynyl, propynyl, butynyl, and 2-butynyl groups Useful cycloalkyl groups are $C_{3-8}$ cycloalkyl. Typical cycloalkyl groups include cyclopropyl, cyclobutyl, cyclopentyl, cyclohexyl and cycloheptyl.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Useful heterocyclic groups include monocyclic heterocyclic groups such as tetrahydrofuranyl, pyranyl, piperidinyl, piperizinyl, pyrrolidinyl, imidazolidinyl, imidazolinyl, morpholinyl, pyrazolidinyl, pyrazolinyl, and the like. Multi-cyclo heterocyclic groups include indolinyl, isoindolinyl, quinuclidinyl, chromanyl, isochromanyl, tetronoyl, tetrahydroisoquinolinyl groups, as well as heterocyclic groups fused with a heteroaryl ring, e.g. optionally substituted 5,6-dihydro-8H-[1,2,4]triazolo[4,3-A]pyrazinyl groups.

Optional substituents include one or more alkyl; halo; haloalkyl; cycloalkyl; aryl optionally substituted with one or more lower alkyl, lower alkoxy, methylenedioxy, halo, haloalkyl, aminosulfonyl, aryl, or heteroaryl groups; aryloxy optionally substituted with one or more lower alkyl, lower alkoxy, methylenedioxy, halo, haloalkyl, aminosulfonyl, aryl, or heteroaryl groups; aralkyl; heteroaryl optionally substituted with one or more lower alkyl, lower alkoxy, methylenedioxy, halo, haloalkyl, aminosulfonyl, aryl, or heteroaryl groups; heteroaryloxy optionally substituted with one or more lower alkyl, lower alkoxy, methylenedioxy, halo, haloalkyl, aminosulfonyl, aryl, or heteroaryl groups; alkoxy; alkylthio; arylthio; amido; amino; aminoalkyl, alkylamino, acyloxy; arylacyloxy optionally substituted with one or more lower alkyl, lower alkoxy, methylenedioxy, halo, haloalkyl, aminosulfonyl, aryl, or heteroaryl groups; diphenylphosphinyloxy optionally substituted with one or more lower alkyl, lower alkoxy, methylenedioxy, halo, haloalkyl, aminosulfonyl, aryl, or heteroaryl groups; heterocyclo optionally substituted with one or more lower alkyl, lower alkoxy, methylenedioxy, halo, haloalkyl, aminosulfonyl, aryl, heteroaryl, amino acid substituted sulfonyl, or amino acid derivative substituted sulfonyl groups; heterocycloacyl optionally substituted with one or more lower alkyl, lower alkoxy, methylenedioxy, halo, haloalkyl, aminosulfonyl, aryl, or heteroaryl groups; heterocycloalkoxy optionally substituted with one or more lower alkyl, lower alkoxy, methylenedioxy, halo, haloalkyl, aminosulfonyl, aryl, or heteroaryl groups; partially unsaturated heterocycloalkyl optionally substituted with one or more lower alkyl, lower alkoxy, methylenedioxy, halo, haloalkyl, aminosulfonyl, aryl, or heteroaryl groups; or partially unsaturated heterocycloalkyloxy optionally substituted with one or more lower alkyl, lower alkoxy, methylenedioxy, halo, haloalkyl, aminosulfonyl, aryl, or heteroaryl groups.

Certain of the compounds of the present invention may exist as stereoisomers including optical isomers. The invention includes all stereoisomers, both as pure individual stereoisomer preparations and enriched preparations of each, and both the racemic mixtures of such stereoisomers as well as the individual enantiomers that may be separated according to methods that are well known to those of skill in the art.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Compounds have the general structure of formula X are synthesized by using a asymmetric 1,3-dipolar cycloaddition as the key step (Scheme 1).

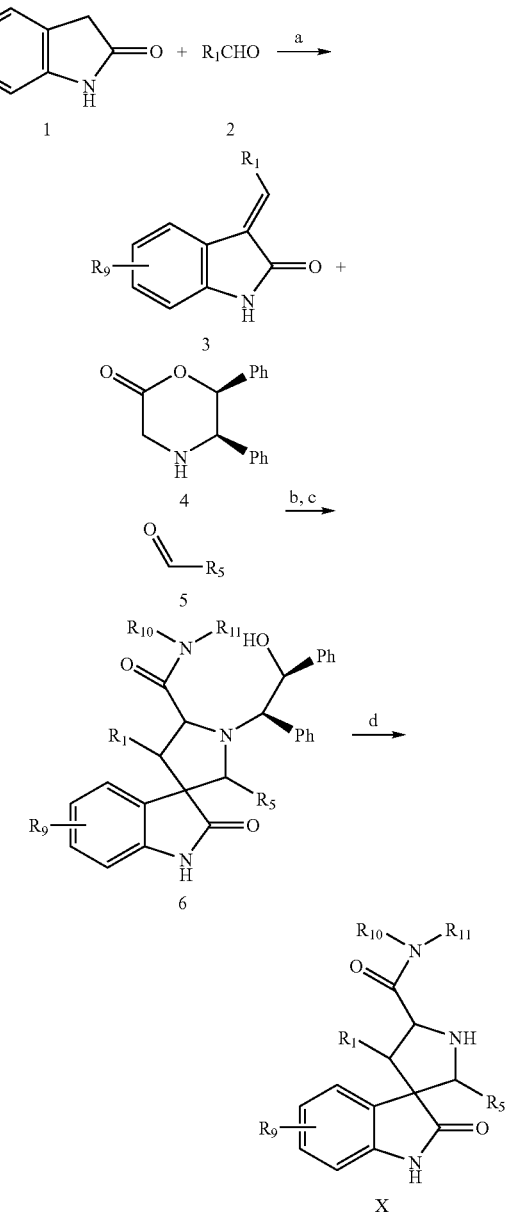

Reagents and conditions: a) $CH_2Cl_2$—$CH_3CN$, KF—$Al_2O_3$, microwave, or methanol, piperidine reflux; b) 4 Å molecular sieves, toluene, 70° C.; c) amine, r.t.; d) $Pb(OAc)_4$, $CH_2Cl_2$-MeOH (1:1), 0° C., or ammonium cerium (IV) nitrate (CAN), $CH_3CN$, $K_2CO_3$, r.t.

Compounds having Formula LXV are prepared by a similar method as the preparation of Formula X (Scheme 5).

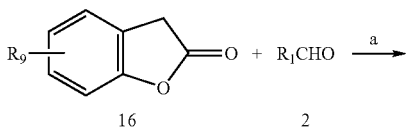

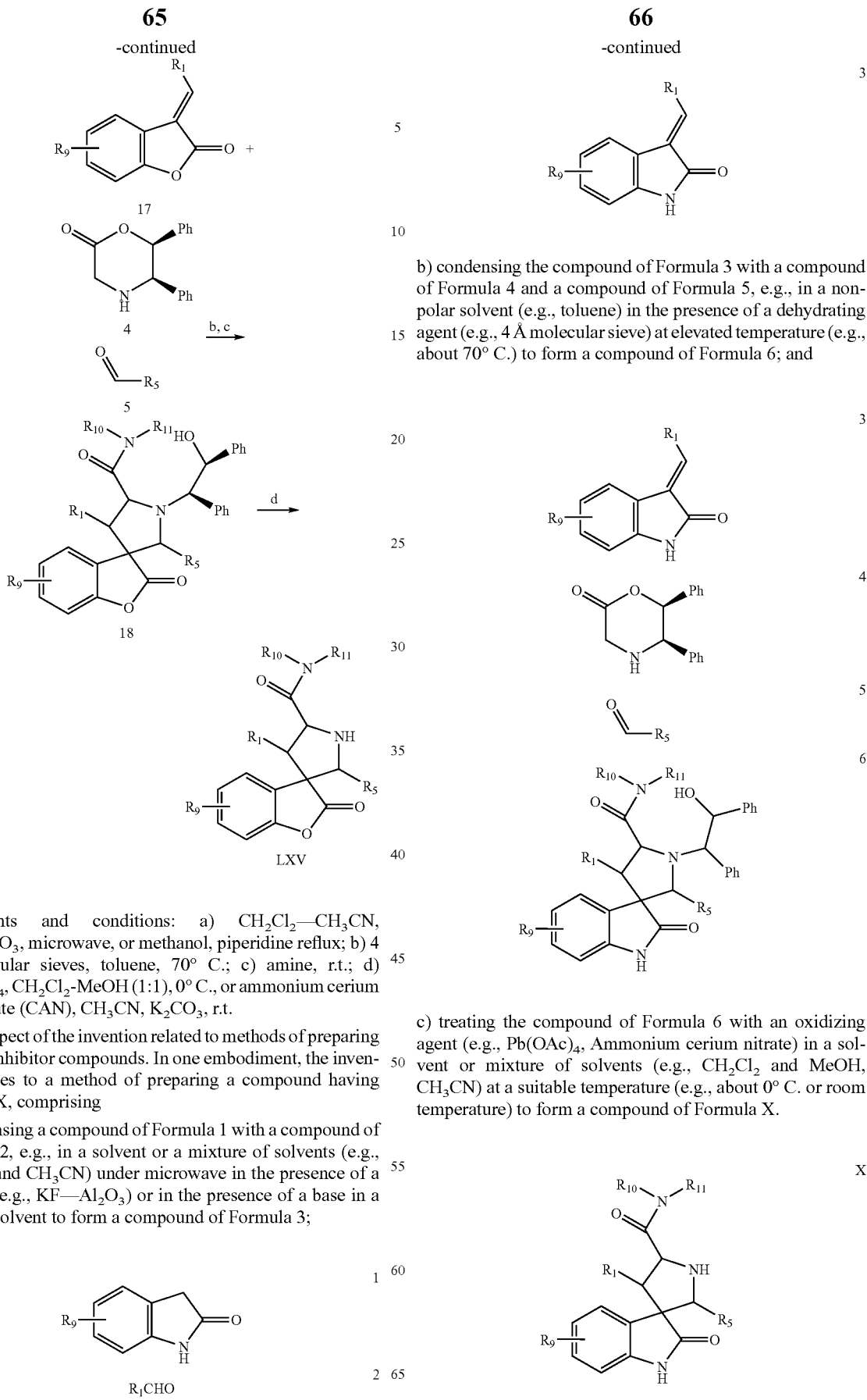

Reagents and conditions: a) $CH_2Cl_2$—$CH_3CN$, KF—$Al_2O_3$, microwave, or methanol, piperidine reflux; b) 4 Å molecular sieves, toluene, 70° C.; c) amine, r.t.; d) Pb(OAc)$_4$, $CH_2Cl_2$-MeOH (1:1), 0° C., or ammonium cerium (IV) nitrate (CAN), $CH_3CN$, $K_2CO_3$, r.t.

One aspect of the invention related to methods of preparing MDM2 inhibitor compounds. In one embodiment, the invention relates to a method of preparing a compound having formula X, comprising a) condensing a compound of Formula 1 with a compound of Formula 2, e.g., in a solvent or a mixture of solvents (e.g., $CH_2Cl_2$ and $CH_3CN$) under microwave in the presence of a catalyst (e.g., KF—$Al_2O_3$) or in the presence of a base in a suitable solvent to form a compound of Formula 3;

b) condensing the compound of Formula 3 with a compound of Formula 4 and a compound of Formula 5, e.g., in a nonpolar solvent (e.g., toluene) in the presence of a dehydrating agent (e.g., 4 Å molecular sieve) at elevated temperature (e.g., about 70° C.) to form a compound of Formula 6; and c) treating the compound of Formula 6 with an oxidizing agent (e.g., Pb(OAc)$_4$, Ammonium cerium nitrate) in a solvent or mixture of solvents (e.g., $CH_2Cl_2$ and MeOH, $CH_3CN$) at a suitable temperature (e.g., about 0° C. or room temperature) to form a compound of Formula X.

In another embodiment, the invention relates to a method of preparing a compound having formula LXV, comprising a) condensing a compound of Formula 16 with a compound of Formula 2, e.g., in a solvent or a mixture of solvents (e.g., $CH_2Cl_2$ and $CH_3CN$) under microwave in the presence of a catalyst (e.g., $KF$—$Al_2O_3$) or in the presence of a base in a suitable solvent to form a compound of Formula 17;

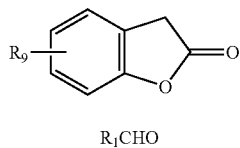

16

$R_1CHO$  2

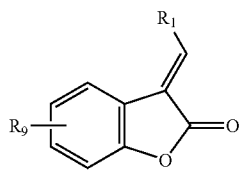

17 b) condensing the compound of Formula 17 with a compound of Formula 4 and a compound of Formula 5, e.g., in a non-polar solvent (e.g., toluene) in the presence of a dehydrating agent (e.g., 4 Å molecular sieve) at elevated temperature (e.g., about 70° C.) to form a compound of Formula 18; and

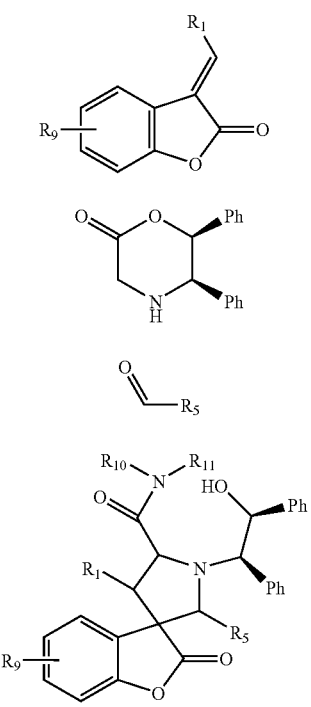

c) treating the compound of Formula 18 with an oxidizing agent (e.g., $Pb(OAc)_4$, Ammonium cerium nitrate) in a solvent or mixture of solvents (e.g., $CH_2Cl_2$ and MeOH, $CH_3CN$) at a suitable temperature (e.g., about 0° C. or room temperature) to form a compound of Formula LXV;

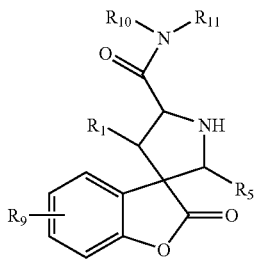

LXV wherein:

$R_1$, $R_5$, $R_9$, $R_{10}$ and $R_{11}$ are as defined above.

An important aspect of the present invention is that compounds of Formula I induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The inhibitors of the interaction between p53 or p53-related proteins and MDM2 or MDM2-related proteins of the present invention can be used to induce apoptosis in any disorder that can be treated, ameliorated, or prevented by the induction of apoptosis. In one embodiment, the inhibitors can be used to induce apoptosis in cells comprising functional p53 or p53-related proteins.

In another embodiment, the invention pertains to modulating an apoptosis associated state which is associated with one or more apoptosis-modulating agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Apoptosis-modulating agents include those which are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formula I and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formula I and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl]benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |

TABLE 1-continued

| | | |
|---|---|---|
| daunorubicin liposomal<br>((8S-cis)-8-acetyl-10-[(3-amino-2,3,6-trideoxy-<br>a-L-lyxo-hexopyranosyl)oxy]-7,8,9,10-<br>tetrahydro-6,8,11-trihydroxy-1-methoxy-5,12-<br>naphthacenedione hydrochloride) | DanuoXome | Nexstar Pharmaceuticals,<br>Inc., Boulder, CO |
| Daunorubicin HCl, daunomycin<br>((1S,3S)-3-Acetyl-1,2,3,4,6,11-hexahydro-<br>3,5,12-trihydroxy-10-methoxy-6,11-dioxo-1-<br>naphthacenyl 3-amino-2,3,6-trideoxy-(alpha)-<br>L-lyxo-hexopyranoside hydrochloride) | Cerubidine | Wyeth Ayerst, Madison, NJ |
| Denileukin diftitox<br>(recombinant peptide) | Ontak | Seragen, Inc., Hopkinton,<br>MA |
| Dexrazoxane<br>((S)-4,4'-(1-methyl-1,2-ethanediyl)bis-2,6-<br>piperazinedione) | Zinecard | Pharmacia & Upjohn<br>Company |
| Docetaxel<br>((2R,3S)-N-carboxy-3-phenylisoserine, N-tert-<br>butyl ester, 13-ester with 5b-20-epoxy-<br>12a,4,7b,10b,13a-hexahydroxytax-11-en-9-<br>one 4-acetate 2-benzoate, trihydrate) | Taxotere | Aventis Pharmaceuticals,<br>Inc., Bridgewater, NJ |
| Doxorubicin HCl<br>(8S,10S)-10-[(3-amino-2,3,6-trideoxy-a-L-<br>lyxo-hexopyranosyl)oxy]-8-glycolyl-7,8,9,10-<br>tetrahydro-6,8,11-trihydroxy-1-methoxy-5,12-<br>naphthacenedione hydrochloride) | Adriamycin,<br>Rubex | Pharmacia & Upjohn<br>Company |
| doxorubicin | Adriamycin<br>PFS<br>Intravenous<br>injection | Pharmacia & Upjohn<br>Company |
| doxorubicin liposomal | Doxil | Sequus Pharmaceuticals, Inc.,<br>Menlo park, CA |
| dromostanolone propionate<br>(17b-Hydroxy-2a-methyl-5a-androstan-3-one<br>propionate) | Dromostanolone | Eli Lilly & Company,<br>Indianapolis, IN |
| dromostanolone propionate | Masterone<br>injection | Syntex, Corp., Palo Alto, CA |
| Elliott's B Solution | Elliott's B<br>Solution | Orphan Medical, Inc |
| Epirubicin<br>((8S-cis)-10-[(3-amino-2,3,6-trideoxy-a-L-<br>arabino-hexopyranosyl)oxy]-7,8,9,10-<br>tetrahydro-6,8,11-trihydroxy-8-<br>(hydroxyacetyl)-1-methoxy-5,12-<br>naphthacenedione hydrochloride) | Ellence | Pharmacia & Upjohn<br>Company |
| Epoetin alfa<br>(recombinant peptide) | Epogen | Amgen, Inc |
| Estramustine<br>(estra-1,3,5(10)-triene-3,17-diol(17(beta))-, 3-<br>[bis(2-chloroethyl)carbamate] 17-(dihydrogen<br>phosphate), disodium salt, monohydrate, or<br>estradiol 3-[bis(2-chloroethyl)carbamate] 17-<br>(dihydrogen phosphate), disodium salt,<br>monohydrate) | Emcyt | Pharmacia & Upjohn<br>Company |
| Etoposide phosphate<br>(4'-Demethylepipodophyllotoxin 9-[4,6-O—(R)-<br>ethylidene-(beta)-D-glucopyranoside], 4'-<br>(dihydrogen phosphate)) | Etopophos | Bristol-Myers Squibb |
| etoposide, VP-16<br>(4'-demethylepipodophyllotoxin 9-[4,6-0-(R)-<br>ethylidene-(beta)-D-glucopyranoside]) | Vepesid | Bristol-Myers Squibb |
| Exemestane<br>(6-methylenandrosta-1,4-diene-3,17-dione) | Aromasin | Pharmacia & Upjohn<br>Company |
| Filgrastim<br>(r-metHuG-CSF) | Neupogen | Amgen, Inc |
| floxuridine (intraarterial)<br>(2'-deoxy-5-fluorouridine) | FUDR | Roche |
| Fludarabine<br>(fluorinated nucleotide analog of the antiviral<br>agent vidarabine, 9-b-D-<br>arabinofuranosyladenine (ara-A)) | Fludara | Berlex Laboratories, Inc.,<br>Cedar Knolls, NJ |
| Fluorouracil, 5-FU<br>(5-fluoro-2,4(1H,3H)-pyrimidinedione) | Adrucil | ICN Pharmaceuticals, Inc.,<br>Humacao, Puerto Rico |
| Fulvestrant<br>(7-alpha-[9-(4,4,5,5,5-penta<br>fluoropentylsulphinyl) nonyl]estra-1,3,5-(10)-<br>triene-3,17-beta-diol) | Faslodex | IPR Pharmaceuticals,<br>Guayama, Puerto Rico |
| Gemcitabine<br>(2'-deoxy-2',2'-difluorocytidine<br>monohydrochloride (b-isomer)) | Gemzar | Eli Lilly |

TABLE 1-continued

| | | |
|---|---|---|
| Gemtuzumab Ozogamicin (anti-CD33 hP67.6) | Mylotarg | Wyeth Ayerst |
| Goserelin acetate (acetate salt of [D-Ser(But)⁶,Azgly¹⁰]LHRH; pyro-Glu-His-Trp-Ser-Tyr-D-Ser(But)-Leu-Arg-Pro-Azgly-NH2 acetate [C₅₉H₈₄N₁₈O₁₄•(C₂H₄O₂)ₓ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6, 7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene)dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin Leucovorin | Immunex, Corp., Seattle, WA |
| Levamisole HCl (((−)-(S)-2,3,5,6-tetrahydro-6-phenylimidazo [2,1-b] thiazole monohydrochloride C₁₁H₁₂N₂S•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |

TABLE 1-continued

| | | |
|---|---|---|
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'][oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by Streptomyces plicatus) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine)butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |

TABLE 1-continued

| | | |
|---|---|---|
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl)phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formula I with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formula I and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (3,4-DIHYDROXY-BUTYL)-AMIDE

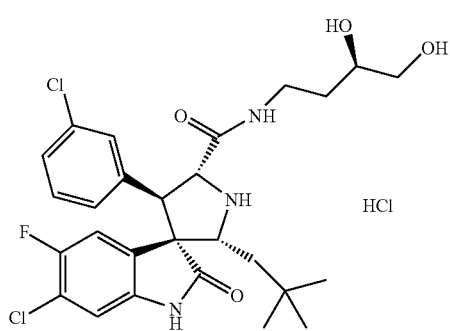

$^{1}$H NMR (300 MHz, CD$_{3}$OH), δ 7.70 (d, 1H, J=8.4 Hz), 7.40-7.20 (m, 3H), 7.09 (m, 1H), 6.88 (d, 1H, J=6.0 Hz), 5.22 (d, 1H, J=11.4 Hz), 4.39 (m, 1H), 4.11 (d, 1H, J=11.1 Hz), 3.65-3.32 (m, 9H), 1.85 (m, 1H), 1.60 (m, 1H), 1.41 (m, 1H), 1.19 (m, 1H), 0.84 (s, 9H).

Example 2

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2,3-DIHYDROXY-PROPYL)-AMIDE

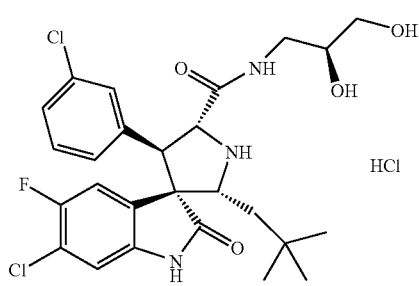

$^{1}$H NMR (300 MHz, CD$_{3}$OH), δ 7.74 (d, 1H, J=7.5 Hz), 7.35-7.15 (m, 3H), 7.11 (m, 1H), 6.88 (d, 1H, J=6.0 Hz), 5.22 (d, 1H, J=11.4 Hz), 4.33 (m, 1H), 4.28 (d, 1H, J=10.5 Hz), 3.67 (m, 2H), 3.65-3.32 (m, 4H), 2.05 (m, 1H), 1.90 (m, 1H), 1.56 (m, 1H), 0.87 (s, 9H).

Example 3

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (3,5-DIHYDROXY-PENTYL)-AMIDE

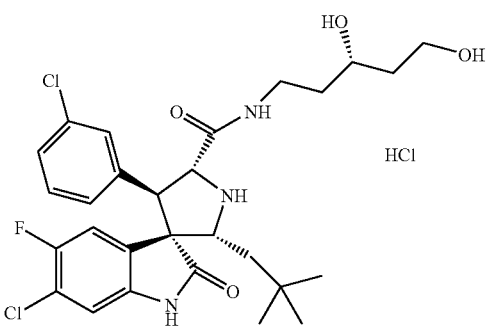

$^{1}$H NMR (300 MHz, CD$_{3}$OH), δ 7.72 (d, 1H, J=8.4 Hz), 7.35-7.15 (m, 3H), 7.10 (m, 1H), 6.88 (d, 1H, J=6.0 Hz), 5.23 (d, 1H, J=11.1 Hz), 4.65 (m, 1H), 4.13 (d, 1H, J=11.4 Hz), 3.61 (m, 2H), 3.65-3.32 (m, 5H), 2.02 (m, 1H), 1.93 (m, 1H), 1.56 (m, 3H), 1.15 (m, 1H), 0.92 (s, 9H).

Example 4

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID [2-(3-HYDROXY-CYCLOPENTYL)-ETHYL]-AMIDE

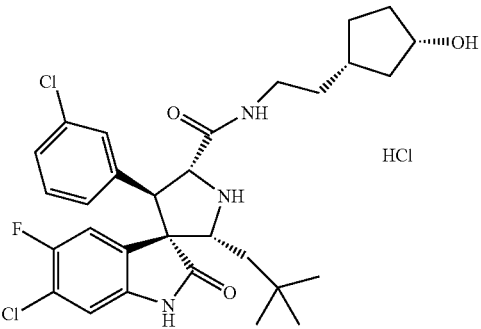

$^{1}$H NMR (300 MHz, CD$_{3}$OH), δ 7.69 (d, 1H, J=8.4 Hz), 7.40-7.20 (m, 3H), 7.10 (m, 1H), 6.86 (m, 1H), 5.24 (d, 1H,

J=11.1 Hz), 4.35 (d, 1H, J=8.4 Hz), 4.09 (m, 1H), 3.61-3.32 (m, 2H), 2.96 (m, 1H), 2.21-1.12 (m, 11H), 0.85 (s, 9H).

Example 5

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID [2-(3-HYDROXY-CYCLOPENTYL)-ETHYL]-AMIDE

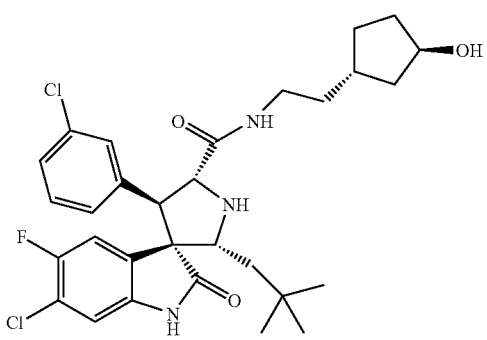

$^1$H NMR (300 MHz, CD$_3$OH), δ 7.69 (d, 1H, J=8.4 Hz), 7.40-7.20 (m, 3H), 7.10 (m, 1H), 6.86 (m, 1H), 5.24 (d, 1H, J=11.1 Hz), 4.48 (d, 1H, J=8.4 Hz), 4.12 (m, 1H), 3.64-3.32 (m, 2H), 2.96 (m, 1H), 2.20-1.10 (m, 11H), 0.85 (s, 9H).

Example 6

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID [2-(3-HYDROXY-CYCLOPENTYL)-ETHYL]-AMIDE

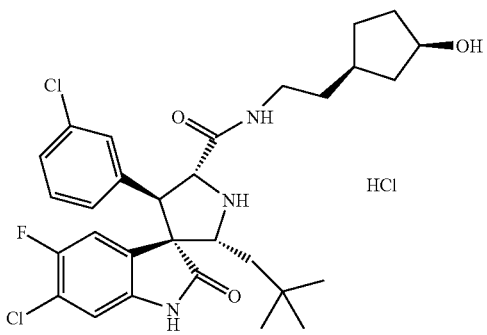

$^1$H NMR (300 MHz, CD$_3$OH), δ 7.69 (d, 1H, J=8.4 Hz), 7.40-7.20 (m, 3H), 7.10 (m, 1H), 6.86 (m, 1H), 5.24 (d, 1H, J=11.1 Hz), 4.47 (d, 1H, J=8.4 Hz), 4.11 (m, 1H), 3.65-3.32 (m, 2H), 2.96 (m, 1H), 2.20-1.10 (m, 11H), 0.91 (s, 9H).

Example 7

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID [2-(3-HYDROXY-CYCLOPENTYL)-ETHYL]-AMIDE

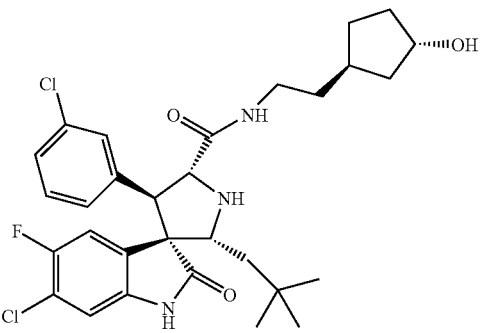

$^1$H NMR (300 MHz, CD$_3$OH), δ 7.72 (d, 1H, J=8.4 Hz), 7.38-7.22 (m, 3H), 7.10 (m, 1H), 6.87 (m, 1H), 5.23 (d, 1H, J=11.1 Hz), 4.48 (d, 1H, J=8.4 Hz), 4.12 (m, 1H), 3.56-3.25 (m, 2H), 2.98 (m, 1H), 2.20-1.10 (m, 11H), 0.86 (s, 9H).

Example 8

6-CHLORO-4'-(3-CHLORO-4-FLUORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID(4,5-DIHYDROXY-PENTYL)-AMIDE

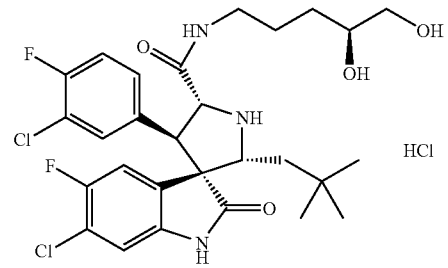

$^1$H NMR (CD$_3$OD, 300 MHz), δ 7.73 (d, J=8.4 Hz, 1H), 7.41 (d, J=7.0 Hz, 1H), 7.14 (d, J=6.7 Hz, 2H), 5.25 (d, J=11.3 Hz, 1H), 4.49 (d, J=6.6 Hz, 1H), 4.15 (d, J=6.4 Hz, 1H), 3.48-3.10 (m, 5H), 1.94 (dd, J=8.1, 15.4 Hz, 1H), 1.70-1.10 (m, 5H), 0.92 (s, 9H).

Example 9

6-CHLORO-4'-(3-CHLORO-4-FLUORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (3-MORPHOLIN-4-YL-PROPYL)-AMIDE

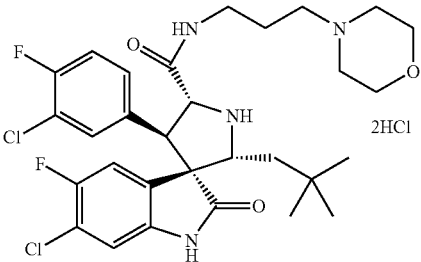

¹H NMR (CD₃OD, 300 MHz), δ 7.82-7.19 (m, 4H), 6.90 (d, J=5.56, 1H), 5.39 (d, J=9.9 Hz, 1H), 4.55 (d, J=6.9 Hz, 1H), 4.28 (d, J=9.3 Hz, 1H), 4.20-3.85 (m, 4H), 3.70-3.40 (m, 2H), 3.25-3.00 (m, 4H), 2.20-1.85 (m, 3H), 1.69 (d, J=15.3 Hz, 2H), 0.934 (s, 9H), 0.70 (t, J=11.3 Hz, 1H).

Example 10

6-CHLORO-4'-(3-CHLORO-2-FLUORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (4-HYDROXY-3-HYDROXYMETHYL-BUTYL)-AMIDE

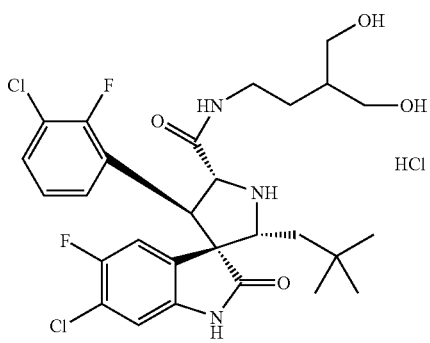

H¹ (300 MHz CD₃OD), δ 8.56 (s br, 1H), 7.68 (t, J=6.6 Hz, 1H), 7.42 (t, J=7.2 Hz, 1H), 7.25 (t, J=7.8 Hz, 1H), 7.05 (d, J=8.7 Hz, 1H), 6.95 (d, J=6.0 Hz, 1H), 5.22 (d, J=10.5 Hz, 1H), 4.54 (d, J=10.5 Hz, 1H), 4.34-4.31 (m, 1H), 3.51-3.49 (m, 4H), 3.36-3.32 (m, 2H), 2.08 (dd, J=15.3, 7.5 Hz, 1H), 1.53-1.49 (m, 2H), 1.33 (dd, J=15.3, 2.7 Hz, 1H), 0.93-0.89 (m, 1H), 0.86 (s, 9H).

Example 11

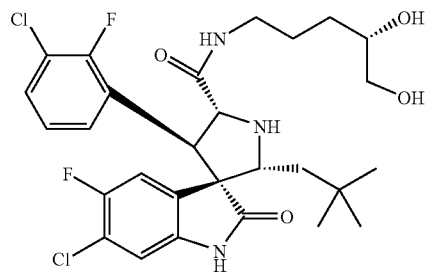

H¹ (300 MHz CD₃OD), δ 8.56 (s br, 1H), 7.65 (t, J=6.6 Hz, 1H), 7.45 (t, J=7.2 Hz, 1H), 7.26 (t, J=7.8 Hz, 1H), 7.01 (d, J=8.7 Hz, 1H), 6.95 (d, J=6.0 Hz, 1H), 5.14 (d, J=10.5 Hz, 1H), 4.51 (d, J=10.5 Hz, 1H), 4.26 (m, 1H), 3.55-3.50 (m, 2H), 3.37-3.31 (m, 3H), 2.08-2.02 (m, 1H), 1.71-1.45 (m, 2H), 1.35-1.23 (m, 3H), 0.86 (s, 9H).

Example 12

6-CHLORO-4'-(3-CHLORO-2-FLUORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID(3,4-DIHYDROXY-BUTYL)-AMIDE

MI-419

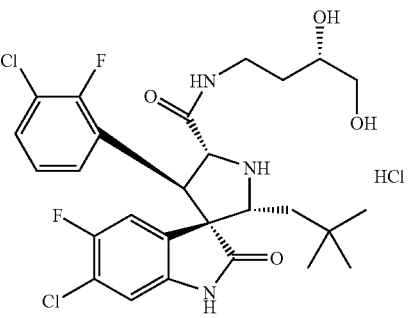

H¹ (300 MHz CD₃OD), δ 8.55 (s br, 1H), 7.66 (t, J=6.6 Hz, 1H), 7.42 (t, J=7.8 Hz, 1H), 7.28-7.23 (m, 2H), 7.01 (d, J=8.7 Hz, 1H), 6.95 (d, J=6.0 Hz, 1H), 5.20 (d, J=10.5 Hz, 1H), 4.53 (d, J=10.5 Hz, 1H), 4.26 (m, 1H), 3.52 (m, 1H), 3.40-3.33 (m, 4H), 2.03 (m, 1H), 1.71-1.45 (m, 2H), 1.35-1.28 (m, 1H), 0.86 (s, 9H).

Example 13

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2-MORPHOLIN-4-YL-ETHYL)-AMIDE

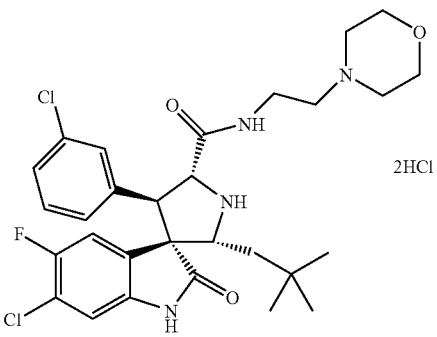

¹H NMR (300 MHz, CD₃OH), δ 7.74 (d, 1H, J=7.5 Hz), 7.35-7.15 (m, 3H), 7.11 (m, 1H), 6.88 (d, 1H, J=6.0 Hz), 5.22 (d, 1H, J=11.4 Hz), 4.55 (d, 1H, J=9.6 Hz), 4.24 (d, 1H, J=6.3

Hz), 4.20-3.85 (m, 4H), 3.70-3.40 (m, 4H), 3.25-3.00 (m, 4H), 2.09 (m, 1H), 1.27 (m, 1H), 0.934 (s, 9H).

Example 14

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (3-MORPHOLIN-4-YL-PROPYL)-AMIDE

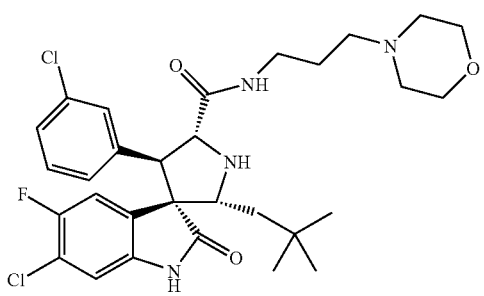

$^1$H NMR (CD$_3$OD, 300 MHz), δ 7.72 (d, 1H, J=8.4 Hz), 7.38-7.22 (m, 3H), 7.10 (m, 1H), 6.87 (m, 1H), 5.23 (d, 1H, J=11.1 Hz), 4.55 (d, J=6.9 Hz, 1H), 4.28 (d, J=9.3 Hz, 1H), 4.20-3.85 (m, 4H), 3.70-3.40 (m, 2H), 3.25-3.00 (m, 4H), 2.20-1.85 (m, 4H), 1.69 (d, J=15.3 Hz, 2H), 0.934 (s, 9H).

Example 15

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (4,5-DIHYDROXY-PENTYL)-AMIDE

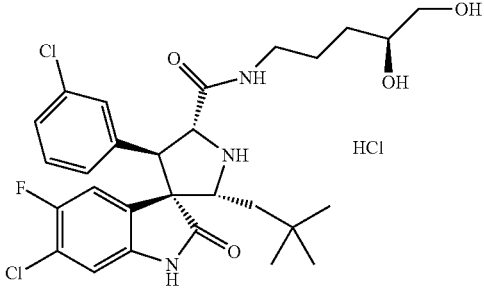

$^1$H NMR (CD$_3$OD, 300 MHz), δ 7.69 (d, 1H, J=8.4 Hz), 7.40-7.20 (m, 3H), 7.10 (m, 1H), 6.86 (m, 1H), 5.24 (d, 1H, J=11.1 Hz), 4.51 (d, J=10.5 Hz, 1H), 4.26 (d, 1H), 3.55-3.50 (m, 2H), 3.37-3.31 (m, 3H), 2.08-2.02 (m, 2H), 1.71-1.45 (m, 2H), 1.35-1.23 (m, 3H), 0.86 (s, 9H).

Example 16

6-CHLORO-4'-(3-CHLORO-PHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (4-HYDROXY-3-HYDROXYMETHYL-BUTYL)-AMIDE

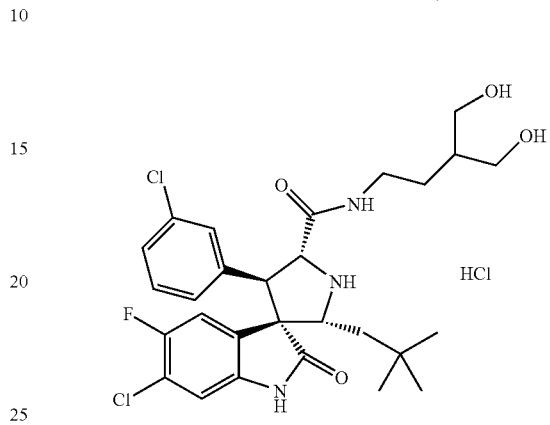

$^1$H NMR (300 MHz, CD$_3$OH), δ 7.69 (d, 1H, J=8.4 Hz), 7.40-7.20 (m, 3H), 7.10 (m, 1H), 6.86 (m, 1H), 5.24 (d, 1H, J=11.1 Hz), 4.54 (d, J=10.5 Hz, 1H), 4.34-4.31 (m, 1H), 3.51-3.49 (m, 4H), 3.36-3.32 (m, 2H), 2.08 (dd, J=15.3, 7.5 Hz, 1H), 1.53-1.49 (m, 2H), 1.33 (dd, J=15.3, 2.7 Hz, 1H), 0.93-0.89 (m, 1H), 0.86 (s, 9H).

Example 17

(2'R,3S,3"S,4'R,5'R)6-CHLORO-4'-(3-CHLORO-4-FLUORO-PHENYL)-2'-(2,2-DIMETHYL-PROPYL)-5-FLUORO-2-OXO-1,2-DIHYDRO-SPIRO [INDOLE-3,3'-PYRROLIDINE]-5'-CARBOXYLIC ACID (3,4-DIHYDROXY-BUTYL)-AMIDE

MI-319

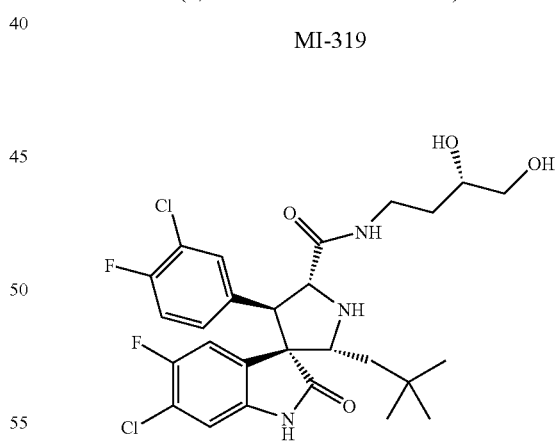

Formula: C$_{27}$H$_{31}$Cl$_2$F$_2$N$_3$O$_4$.HCl (HCl Salt) $^1$H NMR (300 MHz, MeOD), δ 8.44 (m, 1H), 7.70 (d, 1H, J=8.4 Hz), 7.41 (m, 1H), 7.14 (m, 2H), 6.90 (d, 1H, J=6.0 Hz), 5.20 (d, 1H, J=11.1 Hz), 4.47 (d, 1H, J=8.1 Hz), 4.14 (d, 1H, J=10.8 Hz), 3.47 (m, 4H), 1.91 (dd, 1H, J=15.6, 8.4 Hz), 1.57 (m, 1H), 1.43 (m, 1H), 1.21 (dd, 1H, J=15.6, 1.8 Hz), 0.92 (s, 9H); $^{13}$C NMR (75 MHz, MeOD), δ 176.28, 166.52, 157.03, 153.19, 139.65, 130.67, 129.58, 129.48, 128.46, 128.40, 124.54, 124.44, 122.58, 122.33, 121.41, 121.17, 117.21, 116.93, 113.37, 113.03, 112.41, 69.69, 66.05, 64.36, 62.93, 61.91, 55.48, 42.25, 36.99, 32.59, 29.84, 28.40.

Example 18

MI-219

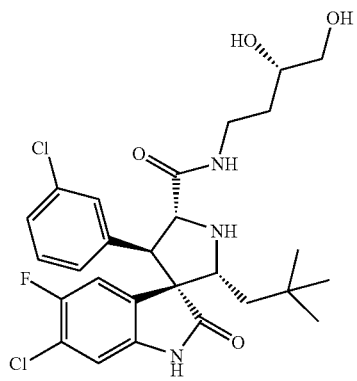

Example 19

6-CHLORO-4'-(3-CHLORO-4-FLUOROPHENYL)-
2'-CYCLOPENTYLMETHYL-5-FLUORO-2-OXO-
1,2-DIHYDRO-SPIRO[INDOLE-3,3'-PYRROLI-
DINE]-5'-CARBOXYLIC ACID (3,4-
DIHYDROXY-BUTYL)-AMIDE

MDM2-319-1

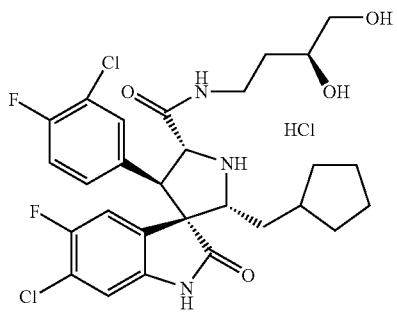

$^1$H NMR (300 MHz, CD$_3$OD), δ 7.72 (d, 1H, J=8.5 Hz), 7.46-7.40 (m, 1H), 7.23-7.12 (m, 2H), 6.88 (d, 1H, J=6.0 Hz), 5.12 (d, 1H, J=11.3 Hz), 4.39-4.35 (m, 1H), 4.14 (d, 1H, J=11.3 Hz), 3.41-3.28 (m, 5H), 1.92-1.78 (m, 2H), 1.62-1.42 (m, 8H), 1.28 (d, 1H, J=15.8 Hz), 1.10-0.90 (m, 2H).

Example 20

MDM2-319-2

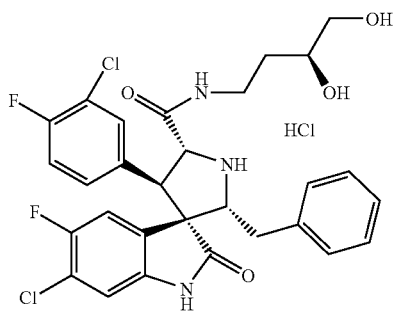

Example 21

MDM2-319-3

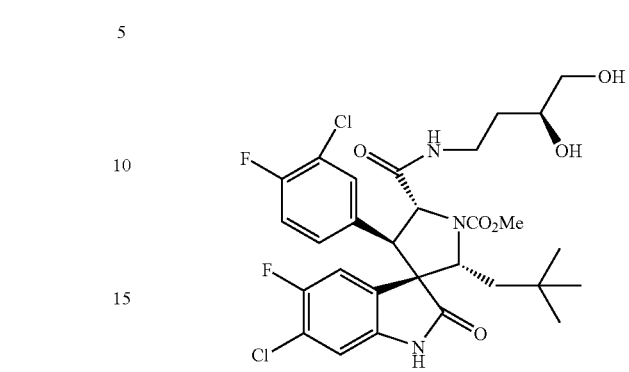

Example 22

6-CHLORO-4'-(3-CHLORO-4-FLUOROPHENYL)-
2'-CYCLOHEXYL-5-FLUORO-2-OXO-1,2-DIHY-
DRO-SPIRO[INDOLE-3,3'-PYRROLIDINE]-5'-
CARBOXYLIC ACID (3,4-DIHYDROXY-
BUTYL)-AMIDE

MDM2-319-4

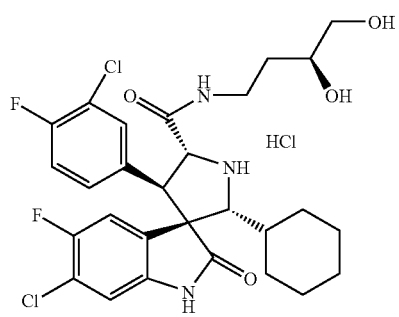

$^1$H NMR (300 MHz, CD$_3$OD), δ 8.54-8.40 (m, 2H), 7.56 (d, 1H, J=8.4 Hz), 7.31-7.29 (m, 1H), 7.16-7.11 (m, 2H), 6.82 (d, 1H, J=6.1 Hz), 4.99-4.95 (m, 1H), 4.21-4.01 (m, 2H), 3.39-3.19 (m, 5H), 2.50-2.40 (m, 1H), 2.00-1.83 (m, 2H), 1.63-1.54 (m, 4H), 1.44-1.09 (m, 6H).

Example 23

MDM2-319-5

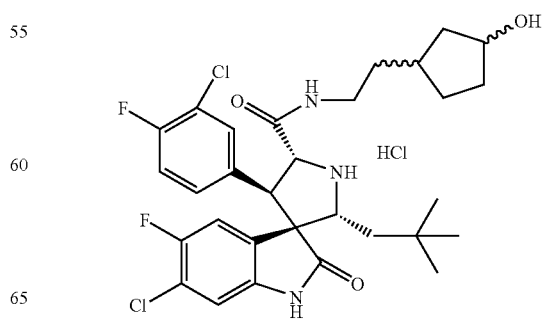

Example 24

6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID [2-(3-HYDROXY-CYCLOPENTYL)-ETHYL]-AMIDE

MDM2-319-6

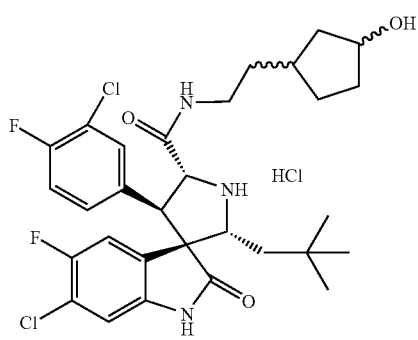

¹H NMR (300 MHz, CD₃OD), δ 8.52-8.49 (m, 1H), 7.72 (d, 1H, J=8.5 Hz), 7.40 (d, 1H, J=10.0 Hz), 7.16-7.15 (m, 2H), 6.90 (d, 1H, J=6.0 Hz), 5.27-5.23 (m, 1H), 4.49 (d, 1H, J=8.2 Hz), 4.14-4.07 (m, 2H), 3.24-3.22 (m, 1H), 3.10-3.02 (m, 1H), 1.93-1.83 (m, 2H), 1.75-1.18 (m, 7H), 1.05-0.93 (m, 1H), 0.92 (s, 9H), 0.85-0.81 (m, 1H).

Example 25

MI-319-7

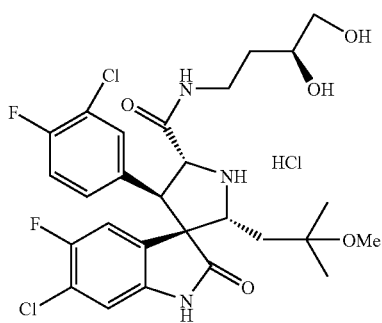

Example 26

6-CHLORO-4'-(3-CHLORO-4-FLUOROPHENYL)-2'-CYCLOPENTYL-5-FLUORO-2-OXO-1,2-DIHYDRO-SPIRO[INDOLE-3,3'-PYRROLIDINE]-5'-CARBOXYLIC ACID (3,4-DIHYDROXY-BUTYL)-AMIDE

MI-319-8

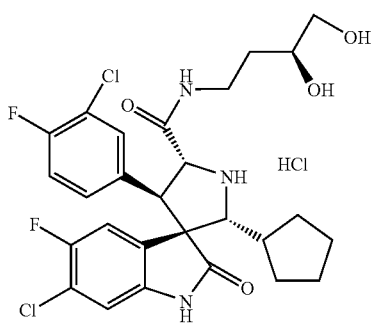

¹H NMR (300 MHz, CD₃OD), δ 7.68 (d, 1H, J=8.5 Hz), 7.40-7.37 (m, 1H), 7.16-7.11 (m, 2H), 6.86 (d, 1H, J=6.0 Hz), 5.15 (d, 1H, J=11.6 Hz), 4.27 (d, 1H, J=11.0 Hz), 4.15 (d, 1H, J=11.6 Hz), 3.39-3.24 (m, 5H), 2.30-2.28 (m, 1H), 2.10-2.05 (m, 1H), 1.62-1.31 (m, 7H), 1.15-1.12 (m, 1H), 0.78-0.75 (m, 1H).

Example 27

6-CHLORO-4'-(3-CHLORO-4-FLUOROPHENYL)-2'-(2,2-DIMETHYL-PROPYL)-5-FLUORO-5'-(4-METHYL-PIPERAZINE-1-CARBONYL)-1H-SPIRO[INDOLE-3,3'-PYRROLIDIN]-2-ONE

MI-319-9

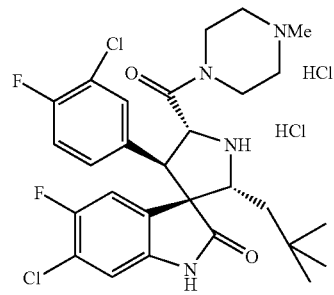

¹H NMR (300 MHz, CD₃OD), δ 7.73-7.70 (m, 1H), 7.58-7.51 (m, 1H), 7.29-7.19 (m, 2H), 6.93-6.89 (m, 1H), 5.83-5.80 (m, 1H), 4.70-4.68 (m, 1H), 4.44-4.25 (m, 2H), 3.98-3.52 (m, 3H), 3.36-3.22 (m, 2H), 2.92-2.85 (m, 3H), 2.40-1.89 (m, 2H), 1.20 (d, 1H, J=15.3 Hz), 0.95-0.90 (m, 9H).

Example 28

MI-319-10

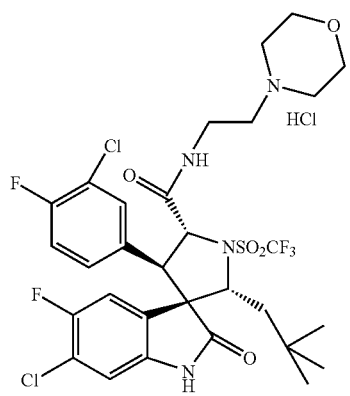

Example 29

MI-319-11

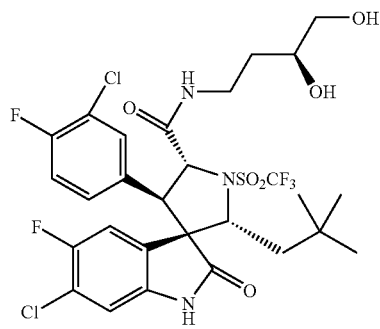

Example 30

MI-319-11

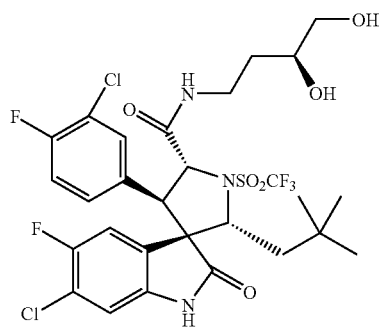

Example 31

MI-319-12

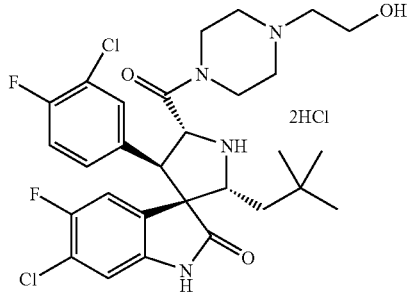

Example 32

1'-ACETYL-6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (3,4-DIHYDROXY-BUTYL)-AMIDE

MI-319-13

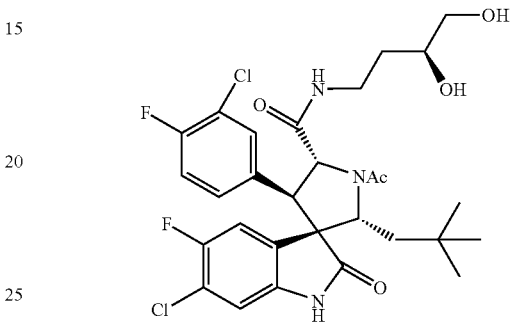

$^1$H NMR (300 MHz, CD$_3$Cl), δ 8.08 (s, 1H), 7.19-7.12 (m, 1H), 6.93-6.77 (m, 4H), 4.93 (d, 1H, J=10.2 Hz), 4.75 (d, 1H, 10.2 Hz), 4.00-3.98 (m, 1H), 3.78-3.30 (m, 5H), 2.80-2.77 (m, 1H), 2.23 (s, 3H), 1.76-1.64 (m, 1H), 1.56-1.52 (m, 2H), 0.92 (s, 9H).

Example 33

6-CHLORO-4'-(3-CHLORO-4-FLUOROPHENYL)-2'-(2,2-DIMETHYL-PROPYL)-5-FLUORO-2-OXO-1'-OXY-1,2,4',5'-TETRAHYDRO-SPIRO[INDOLE-3,3'-PYRROLE]-5'-CARBOXYLIC ACID (3,4-DIHYDROXY-BUTYL)-AMIDE

MI-319-14

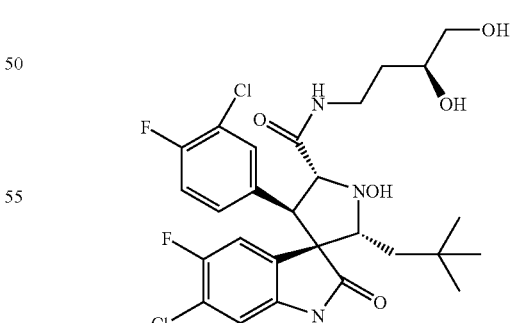

$^1$H NMR (300 MHz, CD$_3$Cl), δ 7.35-7.27 (m, 1H), 7.09-7.07 (m, 1H), 6.92-6.89 (m, 1H), 6.79-6.75 (m, 2H), 5.55 (d, 1H, J=11.0 Hz), 4.20 (d, 1H, J=11.0 Hz), 3.67-3.65 (m, 2H), 3.44-3.32 (m, 3H), 2.80 (d, 1H, J=13.1 Hz), 1.80 (d, 1H, J=13.1 Hz), 1.70-1.60 (m, 2H), 0.84 (s, 9H).

Example 34

{[6-CHLORO-4'-(3-CHLORO-4-FLUOROPHE-NYL)-2'-(2,2-DIMETHYL-PROPYL)-5-FLUORO-2-OXO-1,2-DIHYDRO-SPIRO[INDOLE-3,3'-PYRROLIDINE]-5'-CARBONYL]-AMINO}-ACETIC ACID

MI-319-15

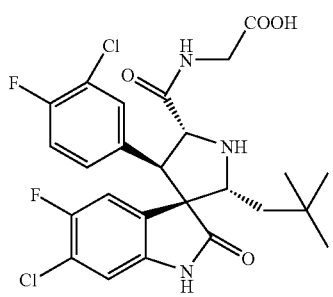

$^1$H NMR (300 MHz, CD$_3$OD), δ 7.64 (d, 1H, J=8.4 Hz), 7.38 (d, 1H, J=6.2 Hz), 7.27-7.21 (m, 1H), 7.10-7.07 (m, 1H), 6.90-6.84 (m, 1H), 5.08 (d, 1H, J=9.9 Hz), 4.22-3.88 (m, 4H), 1.76-1.68 (m, 1H), 1.12-1.06 (m, 1H), 0.84 (s, 9H).

Example 35

MI-319-16

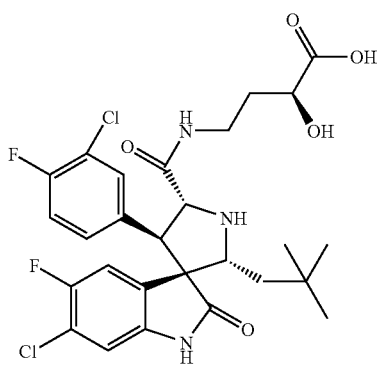

Example 36

6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2-IMIDAZOL-1-YL-ETHYL)-AMIDE

MI-319-17

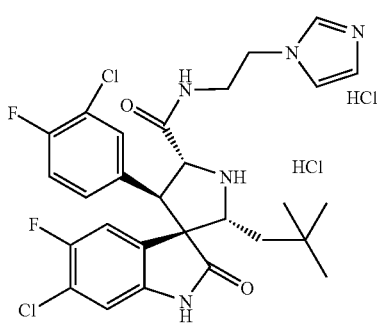

$^1$H NMR (300 MHz, CD$_3$OD), δ 8.99 (s, 1H), 7.78 (d, 1H, J=8.4 Hz), 7.50-7.45 (m, 2H), 7.37-7.35 (m, 1H), 7.19-7.11 (m, 2H), 6.89 (d, 1H, J=6.0 Hz), 5.32 (d, 1H, J=11.4 Hz), 4.52 (d, 1H, J=6.8 Hz), 4.41-4.36 (m, 2H), 4.19 (d, 1H, J=11.4 Hz), 3.73-3.31 (m, 2H), 1.99-1.91 (m, 1H), 1.21-1.16 (m, 1H), 0.92 (s, 9H).

Example 37

7-{[6-CHLORO-4'-(3-CHLORO-4-FLUOROPHE-NYL)-2'-(2,2-DIMETHYL-PROPYL)-5-FLUORO-2-OXO-1,2-DIHYDRO-SPIRO[INDOLE-3,3'-PYRROLIDINE]-5'-CARBONYL]-AMINO}-3,5-DIHYDROXY-HEPTANOIC ACID

MI-319-18

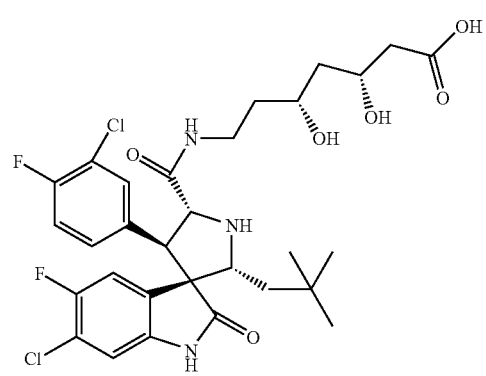

$^1$H NMR (300 MHz, CD$_3$OD), δ 7.60 (d, 1H, J=8.4 Hz), 7.37 (d, 1H, J=7.5 Hz), 7.08-7.06 (m, 2H), 6.87-6.84 (m, 1H), 4.84 (d, 1H, J=10.2 Hz), 4.15-4.08 (m, 1H), 4.00-3.96 (m, 2H), 3.80-3.75 (m, 1H), 3.36-3.32 (m, 2H), 2.49-2.43 (m, 2H), 1.65-1.55 (m, 6H), 1.04 (m, 1H), 0.92 (s, 9H).

Example 38

6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2,3,4-TRIHYDROXY-BUTYL)-AMIDE

MI-319-19

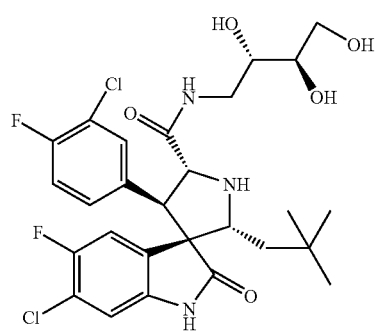

$^1$H NMR (300 MHz, CD$_3$OD), δ 7.83-7.66 (m, 1H), 7.30-7.10 (m, 3H), 6.92-6.88 (m, 1H), 5.30-5.11 (m, 1H), 4.48-4.21 (m, 1H), 4.15-3.95 (m, 1H), 3.64-3.60 (m, 2H), 3.51-3.47 (m, 2H), 3.32-3.24 (m, 2H), 1.95-1.88 (m, 1H), 1.23-1.13 (m, 1H), 0.92-0.82 (m, 9H).

Example 39

6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2-GUANIDINO-ETHYL)-AMIDE

MI-319-20

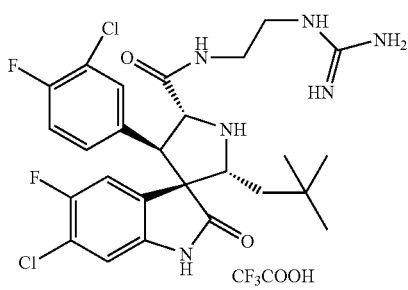

$^1$H NMR (300 MHz, CD$_3$OD), δ 7.69 (d, 1H, J=8.4 Hz), 7.39 (d, 1H, J=6.7 Hz), 7.14-7.04 (m, 2H), 6.89 (d, 1H, J=5.8 Hz), 5.24 (d, 1H, J=11.3 Hz), 4.44 (d, 1H, J=8.0 Hz), 3.80-3.65 (m, 2H), 3.08-3.00 (m, 2H), 1.89-1.87 (m, 1H), 1.71-1.64 (m, 2H), 1.40-1.33 (m, 1H), 0.91 (s, 9H).

Example 40

MI-319-21

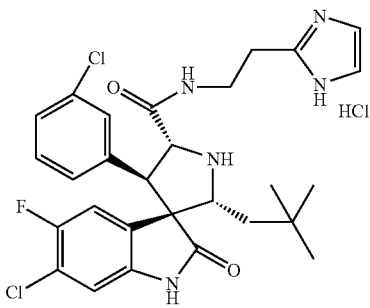

Example 41

6-CHLORO-4'-(3-CHLORO-4-FLUOROPHENYL)-5-FLUORO-2'-(2-METHYL-PROPENYL)-2-OXO-1,2-DIHYDRO-SPIRO[INDOLE-3,3'-PYRROLIDINE]-5'-CARBOXYLIC ACID (3,4-DIHYDROXY-BUTYL)-AMIDE

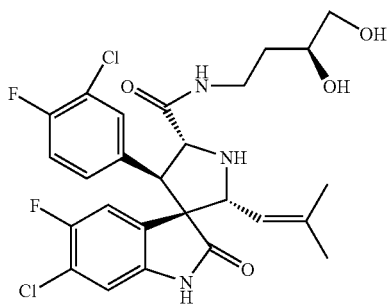

$^1$H NMR (300 MHz, CD$_3$Cl), δ 8.19-8.11 (m, 1H), 7.28-7.19 (m, 3H), 6.96-6.85 (m, 2H), 6.68 (d, 1H, J=5.9 Hz), 4.97 (d, 1H, J=8.9 Hz), 4.60-4.55 (m, 1H), 4.30-4.27 (m, 1H), 3.82 (d, 1H, J=9.2 Hz), 3.71-3.23 (m, 4H), 1.58-1.54 (m, 5H), 1.46 (s, 3H).

Example 42

6-CHLORO-4'-(3-CHLORO-4-FLUOROPHENYL)-2'-(2,2-DIMETHYL-PROPYL)-5-FLUORO-2-OXO-1,2-DIHYDRO-SPIRO[INDOLE-3,3'-PYRROLIDINE]-5'-CARBOXYLIC ACID (2-UREIDO-ETHYL)-AMIDE

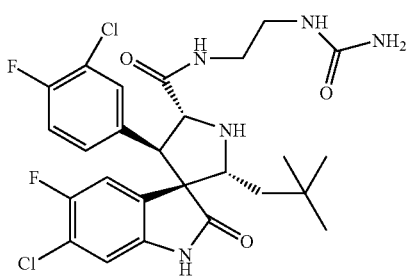

$^1$H NMR (300 MHz, CD$_3$OD), δ 7.71 (d, 1H, J=8.4 Hz), 7.43 (d, 1H, J=6.0 Hz), 7.15-7.12 (m, 2H), 6.93-6.89 (m, 1H), 5.19 (d, 1H, J=11.2 Hz), 4.48 (d, 1H, J=11.2 Hz), 4.16-4.13 (m, 1H), 3.32-3.23 (m, 2H), 2.97-2.89 (m, 2H), 1.95-1.90 (m, 1H), 1.57-1.53 (m, 2H), 1.23-1.18 (m, 1H), 0.92 (s, 9H).

Example 43

(2'R,3S,4'R,5'R)-6-CHLORO-N—((S)-3,4-DIHYDROXYBUTYL)-5-FLUORO-4'-(3-FLUOROPHENYL)-2'-NEOPENTYL-2-OXOSPIRO[INDOLINE-3,3'-PYRROLIDINE]-5'-CARBOXAMIDE

MI-519-1

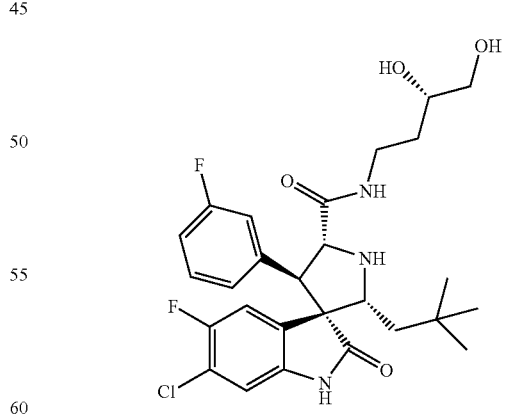

$^1$H NMR (300 MHz, CD$_3$OD), δ 8.43 (m, 1H), 7.72 (d, 1H, J=8.4 Hz), 7.30-7.15 (m, 1H), 7.06 (d, 2H, J=8.88 Hz), 6.95 (d, 1H, J=7.8 Hz), 6.88 (d, 1H, J=6.0 Hz), 5.28 (d, 1H, J=11.3 Hz), 4.51-4.40 (m, 1H), 4.16 (d, J=11.3 Hz), 3.50-3.20 (m, 5H), 1.93 (dd, 1H, J=8.3, 15.5 Hz), 1.62-1.36 (m, 2H), 1.23-1.13 (m, 1H), 0.92 (s, 9H).

Example 44

(2'R,3S,4'S,5'R)-6-CHLORO-4'-(2,3-DIFLUO-ROPHENYL)-N—((S)-3,4-DIHYDROXYBUTYL)-5-FLUORO-2'-NEOPENTYL-2-OXOSPIRO[INDO-LINE-3,3'-PYRROLIDINE]-5'-CARBOXAMIDE

MI-519-2

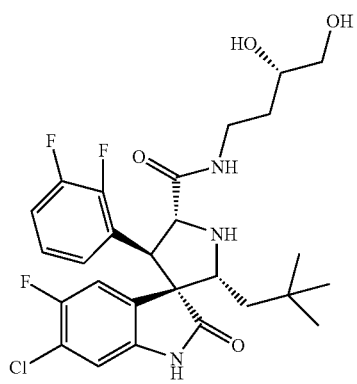

$^1$H NMR (300 MHz, CD$_3$OD), δ 8.47 (m, 1H), 7.73 (d, 1H, J=7.2 Hz), 7.43-7.30 (m, 1H), 7.23-7.15 (m, 2H), 6.89 (d, 1H, J=6.0 Hz), 5.29 (d, 1H, J=11.1 Hz), 4.64 (d, 1H, J=11.4 Hz), 4.58-4.50 (m, 1H), 3.50-3.20 (m, 5H), 1.93 (dd, 1H, J=8.3, 15.5 Hz), 1.67-1.36 (m, 2H), 1.23-1.13 (m, 1H), 0.92 (s, 9H).

Example 45

(2'R,3S,4'R,5'R)-6-CHLORO-4'-(3,4-DIFLUO-ROPHENYL)-N—((S)-3,4-DIHYDROXYBUTYL)-5-FLUORO-2'-NEOPENTYL-2-OXOSPIRO[INDO-LINE-3,3'-PYRROLIDINE]-5'-CARBOXAMIDE

MI-519-3

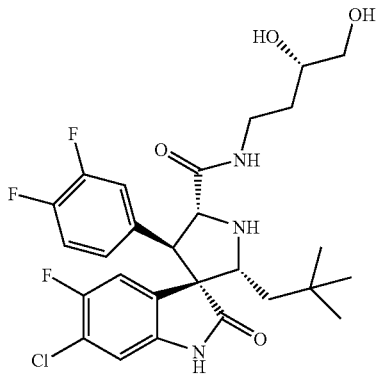

$^1$H NMR (300 MHz, CD$_3$OD), δ 8.43 (m, 1H), 7.73-7.69 (m, 1H), 7.27-1.10 (m, 2H), 6.97-6.94 (m, 1H), 6.90 (d, 1H, J=6.0 Hz), 5.26-5.23 (m, 1H), 4.49 (d, 1H, J=7.5 Hz), 4.16-4.13 (m, 1H), 3.50-3.15 (m, 5H), 1.96-1.88 (m, 1H), 1.62-1.40 (m, 2H), 1.23-1.13 (m, 1H), 0.92 (s, 9H).

Example 46

(2'R,3S,4'S,5'R)-6-CHLORO-4'-(2,5-DIFLUO-ROPHENYL)-N—((S)-3,4-DIHYDROXYBUTYL)-5-FLUORO-2'-NEOPENTYL-2-OXOSPIRO[INDO-LINE-3,3'-PYRROLIDINE]-5'-CARBOXAMIDE

MI-519-5

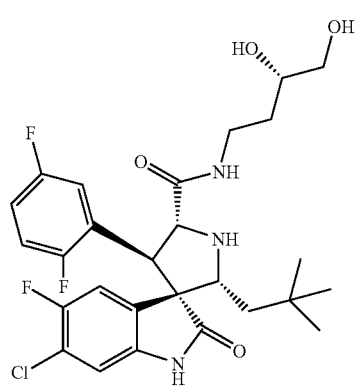

$^1$H NMR (300 MHz, CD$_3$OD), δ 8.49 (m, 1H), 7.71 (d, 1H, J=7.2 Hz), 7.45-7.40 (m, 1H), 7.15-7.00 (m, 2H), 6.89 (d, 1H, J=6.0 Hz), 5.23 (d, 1H, J=11.1 Hz), 4.63 (d, 1H, J=11.4 Hz), 4.58-4.50 (m, 1H), 3.50-3.20 (m, 5H), 1.93 (dd, 1H, J=8.3, 15.5 Hz), 1.67-1.36 (m, 2H), 1.18 (dd, 1H, J=1.9, 15.5 Hz), 0.92 (s, 9H).

Example 47

(2'R,3S,4'S,5R)-6-CHLORO-N—((S)-3,4-DIHY-DROXYBUTYL)-5-FLUORO-4'-(2-FLUOROPHE-NYL)-2'-NEOPENTYL-2-OXOSPIRO[INDOLINE-3,3'-PYRROLIDINE]-5'-CARBOXAMIDE

MI-519-6

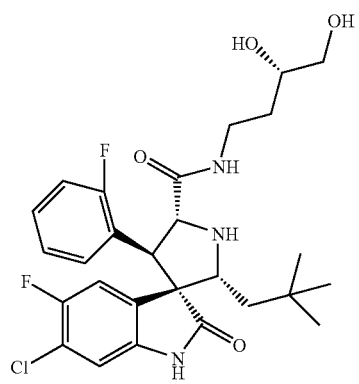

$^1$H NMR (300 MHz, CD$_3$OD), δ 8.43 (m, 1H), 7.70-7.64 (m, 2H), 7.40-7.18 (m, 2H), 7.01-6.94 (m, 1H), 6.85 (d, 1H, J=6.0 Hz), 5.25 (d, 1H, J=11.3 Hz), 4.62 (d, 1H, J=12 Hz), 4.55-4.52 (m, 1H), 3.50-3.20 (m, 5H), 1.91 (dd, 1H, J=8.3, 15.5 Hz), 1.62-1.32 (m, 2H), 1.18 (dd, 1H, J=1.8, 15.3 Hz), 0.92 (s, 9H).

Example 48

(2'R,3S,4'R,5'R)-6-CHLORO-N—((S)-3,4-DIHYDROXYBUTYL)-5-FLUORO-4'-(4-FLUOROPHENYL)-2'-NEOPENTYL-2-OXOSPIRO [INDOLINE-3,3'-PYRROLIDINE]-5'-CARBOXAMIDE

MI-519-7

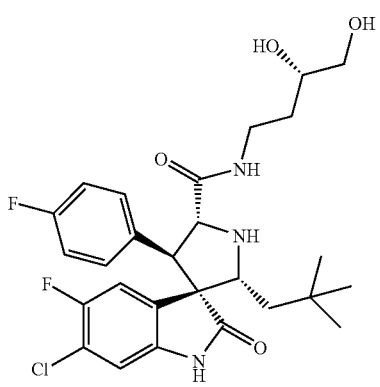

$^1$H NMR (300 MHz, CD$_3$OD), δ 8.39 (m, 1H), 7.70 (d, 1H, J=8.5 Hz), 7.25-7.21 (m, 2H), 7.03-6.96 (m, 2H), 6.87 (d, 1H, J=6.0 Hz), 5.26 (d, 1H, J=11.3 Hz), 4.48 (m, 1H), 4.12 (d, J=11.4 Hz), 3.50-3.20 (m, 5H), 1.92 (dd, 1H, J=8.3, 15.5 Hz), 1.62-1.32 (m, 2H), 1.20 (dd, 1H, J=2.0, 15.3 Hz), 0.92 (s, 9H).

Example 49

Cell Growth Inhibition

One major advantage of non-peptide small-molecule inhibitors over peptide-based inhibitors is their superior cell permeability. It is predicted that potent, non-peptide inhibitors of the p53-MDM2 interaction will be effective in inhibition of cell growth and division in cancer cells with a wild-type form of p53 through stimulation of the activity of p53. Furthermore, they are predicted to have selectivity in cancer cells with either a loss of p53 or a mutated, non-functional form of p53. To test these predictions, a cell growth assay was developed using human prostate cancer LNCaP (p53 wild-type) and PC-3 (p53 null) cell lines. The toxic effects of compounds of the invention were tested.

Cells were seeded in 96-well flat bottom cell culture plates at a density of 3-4×10$^3$ cells/well and incubated in the presence of compounds for 4 days. The rate of cell growth inhibition after treatment with increasing concentrations of the compounds was determined using WST-8 (2-(2-methoxy-4-nitrophenyl)-3-(4-nitrophenyl)-5-(2,4disulfophenyl)-2H-tetrazolium monosodium salt (Dojindo Molecular Technologies Inc., Gaithersburg, Md.). WST-8 was added at a final concentration of 10% to each well and the plates were incubated at 37° C. for 2-3 hrs. The absorbance of the samples was measured at 450 nm in a plate reader (Molecular Device-TECAN ULTRA). The concentration of the compounds that inhibited cell growth by 50% (IC$_{50}$) was calculated by comparing absorbance in the untreated cells and the cells treated with the compounds. As shown in Table 2, the compounds of the invention were about 5-fold to about 50-fold more effective at inhibiting cell growth in p53-positive LNCaP cells as compared to p53-negative PC3 cells.

The compounds of the invention were similarly tested against HCT116 (wild-type p53), and HT-29 (mutant p53) colon cancer cell lines. As shown in Table 2, the majority of the tested compounds exhibited a higher potency for cell growth inhibition in p53-positive HCT116 cells as compared to p53-negative HCT116 cells, with the largest difference in potency being about 25-fold.

Since normal cells also have wild-type p53, a potential concern in development of inhibitors of the p53-MDM2 interaction as new anti-cancer drugs is that they may be nonselective and equally active in killing normal cells as they are in killing cancer cells. Compounds will be evaluated in normal human prostate epithelial cells (PrEC) with wild-type p53 to confirm whether they display a good selectivity for cancer cells.

TABLE 2

| Compound | IC$_{50}$ ± SD (μM)* (Ki ± SD) (μM) | LNCaP IC$_{50}$ (μM) | PC3 IC$_{50}$ (μM) | HCT116 p53WT IC$_{50}$ (μM) | HCT116 p53KO IC$_{50}$ (μM) |
|---|---|---|---|---|---|
| MDM2-319 | 0.076 (0.0063) | 0.2738 | 15.4 | 0.7174 | 11.83 |
|  | 0.077 (0.006) | 0.1839 | 9.08 | 0.6145 | 12.2 |
|  | 0.064 (0.005) | 0.2291 | 1.35 | 0.2466 | 14.23 |
|  | 0.092 | 0.2289 ± 0.04 | 11.61 ± 3.3 | 0.52 ± 0.24 | 12.75 ± 1.29 |
|  | 0.115 |  |  |  |  |
|  | 0.122 |  |  |  |  |
|  | 0.13 |  |  |  |  |
|  | 0.18 |  |  |  |  |
|  | 0.17 |  |  |  |  |
|  | 0.16 |  |  |  |  |
|  | 0.10 |  |  |  |  |
| MDM2-319-1 | 0.194 | 0.2612 | HCT116 | 0.9085 | 12.66 |
|  | 0.072 | 0.3602 |  | 1.364 | 10.39 |
| MDM2-319-2 | 175 (16.43) | 3.474 | 14.39 | 15.46 | 22.24 |
|  | >80 | 3.378 | 19.64 | 21.3 | 19.49 |
|  |  | 4.005 | 19.58 | 8.508 | 25.44 |
|  |  | 3.61 ± 0.3 | 17.87 ± 3.01 | 15.08 ± 6.4 | 22.39 ± 2.97 |
| MDM2-319-3 | 0.37 (0.034) | 1.758 | 16.65 | 3.813 | 13.84 |
|  | 0.45 | 1.241 | 17.45 | 4.109 | 24.78 |
|  | 0.23 | 0.8472 | 22.16 | 2.826 | 16.72 |
|  |  | 1.28 ± 0.4 | 18.75 ± 2.97 | 3.58 ± 0.67 | 18.44 ± 5.67 |

TABLE 2-continued

| Compound | IC$_{50}$ ± SD (μM)* (Ki ± SD) (μM) | LNCaP IC$_{50}$ (μM) | PC3 IC$_{50}$ (μM) | HCT116 p53WT IC$_{50}$ (μM) | HCT116 p53KO IC$_{50}$ (μM) |
|---|---|---|---|---|---|
| MDM2-319-4 | 0.71 (0.066) | 1.417 | 18.53 | 5.03 | 13.13 |
|  | 1.16 | 1.294 | 23.38 | 5.801 | 26.48 |
|  | 0.46 | 0.8902 | 25.6 | 2.413 | 13.39 |
|  |  | 1.21 ± 0.29 | 22.5 ± 3.61 | 4.41 ± 1.77 | 17.6 ± 7.6 |
| MDM2-319-5 | 0.055 | 0.6020 | 9.47 | 0.9927 | 10.52 |
|  | 0.040 | 0.4653 | 5.553 | 1.286 | 5.39 |
|  |  | 0.6341 | 8.711 | 1.502 | 8.403 |
|  |  | 0.56 ± 0.08 | 7.91 ± 2 | 1.23 ± 0.2 | 8.1 ± 2.5 |
| MDM2-319-6 | 0.59 | 2.583 | 21.4 | 5.452 | 14.29 |
|  | 0.55 Flu | 1.223 | 20.83 | 7.41 | 16.06 |
|  |  | 1.931 | 14.15 | 5.957 | 14.58 |
|  |  | 1.91 ± 0.6 | 18.7 ± 4 | 6.26 ± 1.0 | 14.97 ± 0.9 |
| MI-319-7 | 39.33 | 2.17 | 39.74 | 8.22 | >30 |
|  |  | 1.917 | 34.29 | 7.954 | >30 |
| MI-319-8 | 0.34 | 0.9631 | 30.66 | 4.114 | 30.95 |
|  | 0.53 | 0.8928 | 20.72 | 4.732 | 25.48 |
|  |  | 0.6625 | 18.43 | 2.738 | 22.69 |
|  |  | 1.46 ± 1.13 | 23.27 ± 6.5 | 3.86 ± 1.02 | 26.3 ± 4.2 |
| MI-319-9 | 3.58 | 2.866 | 20.91 | 7.48 | 9.711 |
|  |  | 2.766 | 5.547 | 9.198 | 8.189 |
|  |  | 1.75 | 6.09 | 4.631 | 4.52 |
|  |  | 2.46 ± 0.61 | 11.12 ± 8.5 | 7.1 ± 2.3 | 7.47 ± 2.66 |
| MI-319-10 | 0.22 | 0.7764 | 10.47 | 1.411 | 11.58 |
|  | 0.26 | 0.8283 | 10.36 | 1.947 | 9.84 |
|  |  | 0.4493 | 8.074 | 1.088 | 5.454 |
|  |  | 0.68 ± 0.2 | 9.63 ± 1.35 | 1.48 ± 0.4 | 8.9 ± 3.1 |
| MI-319-11 | 5.13 | 2.846 | 17.29 | 13.5 | 13.38 |
|  | 5.39 | 3.078 | 14.71 | 15.82 | 18 |
|  | 5.11 | 4.219 | 24.24 | 24.89 | 24.68 |
|  |  | 3.38 ± 0.73 | 18.7 ± 4.9 | 18.4 ± 5.9 | 18.85 ± 5.45 |
| MI-319-11-A | 2.24 | 0.3078 | 1.765 | 2.153 | 3.966 |
|  | 1.64 | 0.5313 | 2.754 | 2.816 | 2.627 |
|  |  | 0.4624 | 4.024 | 0.9753 | 4.182 |
|  |  | 0.43 ± 0.11 | 2.84 ± 1.1 | 1.98 ± 0.9 | 3.59 ± 0.84 |
| MI-319-12 | 2.30 | 1.974 | 22.35 | 12.37 | 13.45 |
|  | 2.96 | 2.571 | 20.89 | 13.2 | 17.84 |
|  |  | 1.931 | 13.31 | 4.365 | 14.13 |
|  |  | 2.15 ± 0.35 | 18.85 ± 4.85 | 9.97 ± 4.87 | 15.14 ± 2.36 |
| MI-319-13 | 5.87 | 3.663 | 17.2 | 3.227 | 32.64 |
|  | 5.04 | 2.316 | 14.48 | 6.368 | 35.05 |
|  |  | 4.85 | 20.28 | 10.98 | 33.02 |
|  |  | 3.6 ± 1.26 | 17.32 ± 2.9 | 6.85 ± 3.8 | 33.57 ± 1.29 |
| MI-319-14 | 2.04 | 4.221 | 40.08 | 8.008 | >30 |
|  | 1.66 | 2.63 | 40.2 | 9.266 | >30 |
|  |  | 1.979 | >30 | 5.738 | >30 |
|  |  | 2.94 ± 1.1 |  | 7.67 ± 1.7 |  |
| MI-319-15 | 0.35 | 4.522 | >30 | 12.13 | >30 |
|  | 0.18 | 4.125 | >30 | 12.89 | >30 |
|  |  | 6.113 | >30 | 13.89 | >30 |
|  |  | 4.92 ± 1.05 |  | 12.97 ± 0.88 |  |
| MI-319-16 | 0.85 (Flu) | 24.07 | >30 | >30 | >30 |
|  | 0.76 (Flu) |  |  |  |  |
| MI-319-17 | 0.39 | 1.098 | 14 | 2.096 | 25.13 |
|  | 0.49 | 1.548 | 22.02 | 3.792 | 22.33 |
|  |  | 1.511 | 23.63 | 3.148 | 25.14 |
| MI-319-18 | 3.51 | >30 | >30 | >30 | >30 |
|  | 3.57 | >30 | >30 | >30 | >30 |
| MI-319-19 | 0.50 | 1.235 | 30.68 | 2.68 | >30 |
|  | 0.49 | 2.398 | >30 | 5.981 | >30 |
|  |  | 1.2 | 41.65 | 4.596 | 77.64 |
| MI-319-20 |  | 27.44 | >30 | >30 | >30 |
|  |  | 31.59 | 66.12 | 93.54 | >100 |
| MI-319-21 |  | 2.838 | 21.87 | 4.402 | 11.76 |
|  |  | 1.836 | 14.07 | 3.884 | 13.25 |

Calculation of K$_i$: MDM2 [10 nM]; F-6 [1 nM]; New Sample MDM2 protein:

K$_d$: 0.88 ± 0.41 nM (Hyperbolic equation; using 1 nM 6F)

K$_d$: 2.22 ± 0.93 nM (Klotz plot; using 1 nM 6F)

Example 50

Effects of MDM2 Inhibitors on Expression of p53 and its Target Gene Products MDM2 and p21

Cancer cells are treated with test compounds or 0.1% DMSO for 24 hours. Cells are harvested by trypsinization and washed with cold phosphate buffer saline, pH 7.5 (Invitrogen, Carlsbad, Calif.). Cells are lysed for 30 minutes in ice-cold lysis buffer (50 mM Tris (pH 7.5), 150 mM NaCl, 1 mM EDTA (pH 8.0), 25 mM sodium fluoride, 1% NP-40 and 0.1% SDS) containing 2 mM sodium orthovanadate, 1 mM phenylmethylsulfonyl fluoride and protease inhibitor cocktail (Roche Applied Science, Indianapolis, Ind.). Next, cell extracts are centrifuged at 12,000×g at 4° C. for 10 minutes to obtain clarified lysates. Protein is estimated by Bio-Rad dye. Cell lysates containing 35 µg protein are resolved on a 4-20% tris-glycine gel (Invitrogen, Carlsbad, Calif.) and transferred onto poly(vinylidene difluoride) membranes. Immunodetection of proteins on the transfer membrane is performed by using anti-p53 (Ab-6, Oncogene Research Products, Boston, Mass.), anti-MDM2 (SMP14, Santa Cruz Biotechnology, Santa Cruz, Calif.) and anti-p21 (BD Biosciences, San Diego, Calif.) mouse monoclonal antibodies. Antibody to β-actin (Sigma, St Louis, Mo.) is used to assess the protein loading. When RKO (wild-type p53) and HT-29 (mutant p53) colon cancer cell lines are treated for 24 hours with the compounds of the invention, it is expected that the compounds will induce accumulation of p53 and its target gene-products only in RKO cells expressing wild-type p53.

Example 51

Cell Death and Apoptosis Induced by MDM2 Inhibitors

RKO (wild-type p53) and HT-29 (mutant p53) colon cancer cell lines and CCD-18Co normal colon fibroblast cells are treated with increasing doses of the compounds of the invention for 4 days in 6-well Petri dishes. Trypan blue dye exclusion assays are performed to determine the ability of the inhibitors to induce cell death. After 4 days of treatment, floating and adherent cells are harvested and stained with 0.2% of trypan blue solution (Sigma, St Louis, Mo.). Each treatment is performed in triplicate and at least 100 cells are counted. Cells stained blue or morphologically unhealthy cells are scored as dead cells. To evaluate apoptosis, sub-diploid DNA content in cells treated with or without test inhibitors is analyzed by propidium iodide (PI) staining. After washing once with cold PBS, cells are fixed in 70% ethanol for 1 day at −20° C. Ethanol-fixed cells are then washed twice with PBS and stained with a staining solution containing propidium iodide (PI) at 50 µg/ml and RNAse A at 100 µg/ml in PBS, for 20 minutes in dark at room temperature. Acquisition of cells and analysis of sub-diploid DNA content is performed by flow cytometry using CellQuest software. It is expected that only cancer cells expressing wild-type p53 will undergo apoptosis in response to administration of the compounds.

Example 52

Effect of MDM2 Inhibitors on Cell Cycle Progression of Colon Cancer Cells

Cell cycle progression is evaluated in RKO (wild-type p53) and HT-29 (mutant p53) colon cancer cell lines and CCD-18Co normal colon fibroblast cells by determining S-phase cells by incorporation of bromodeoxyuridine (BrdU) followed by staining with FITC-labeled anti-BrdU antibody and the total DNA-content by staining with 7-aminoactinomycin D (7-AAD) according to manufacturer's instructions (BD Biosciences, San Jose, Calif.). Briefly, cancer and normal cells, after overnight incubation, are treated with or without test compounds for 22 hours, followed by an additional 2 hours of incubation with 10 µM of BrdU. Cells are harvested, fixed and stained with FITC-labeled anti-BrdU and 7-AAD. Cell cycle distribution is analyzed by flow cytometry. Cells are acquired and data analyzed by using CellQuest software (BD Biosciences). It is expected that the compounds of the invention will induce a dose-dependent depletion of S-phase in RKO cancer cells and in CCD-18Co normal colon fibroblast cells, both of which express wild-type p53. It is also expected that the compounds will have no appreciable effect on cell cycle progression of HT-29 cells expressing mutant p53.

Example 53

Protection of Normal Cells Form Chemotherapy with MDM2 Inhibitors

PrEC normal prostate epithelial cells are seeded in 6 well plates and incubated with compounds of the invention for 24 hours, then 1 µM TAXOL (paclitaxel) is added for 2 days. Trypan blue is used to determine cell viability. The data is expected to show that when normal prostate epithelial cells are pretreated with the compounds of the invention, cells are protected from TAXOL.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound having Formula I:

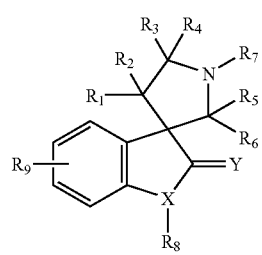

or a pharmaceutically acceptable salt or prodrug thereof, wherein:

X is O, or S;

Y is O, S, or NR';

$R_1$, $R_2$, $R_4$, $R_5$, $R_6$, and $R_7$ are independently H or optionally substituted alkyl, cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, $(C\!\!=\!\!NR')NR''R'''$, or $NR'R''$; or $R_7$ forms an aryl, cycloalkyl, or heterocyclic group with one of $R_5$ or $R_6$;

$R_8$ is absent;

$R_9$ represents a 6-chloro and a 5-fluoro group; and each R', R" and R''' is independently H or optionally substituted alkyl, cycloalkyl, alkenyl, cycloalkenyl, alkynyl, aryl, or heterocyclic; or R' and R", or R" and R''', form a ring;

wherein one of $R_3$ and $R_4$ is CONRR', and one of R and R' is an optionally substituted cycloalkyl-alkyl or monocyclo-heterocycloalkyl group or a dihydroxyalkyl amino group not containing a hydroxyl group at the 3-position of the alkyl group.

2. The compound of claim 1, having Formula II or Formula III:

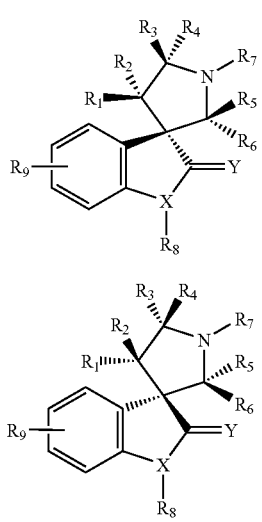

II

III or a pharmaceutically acceptable salt or prodrug thereof.

3. The compound of claim 1, wherein one of $R_1$ and $R_2$ is optionally substituted aryl or heteroaryl.

4. The compound of claim 1, wherein one of $R_1$ and $R_2$ is cycloalkyl, straight or branched alkyl, amide or ester.

5. The compound of claim 1, wherein one of $R_5$ and $R_6$ is $C_{3-18}$ alkyl, aryl, or heteroaryl.

6. The compound of claim 1, having Formula XLVIII:

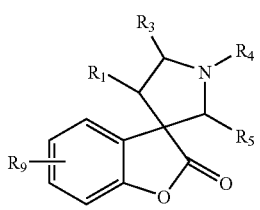

XLVIII or a pharmaceutically acceptable salt or prodrug thereof.

7. The compound of claim 6, having one of Formulae XLIX-LXIV:

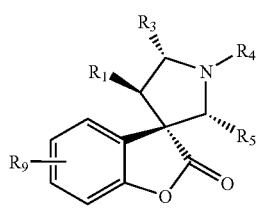

XLIX

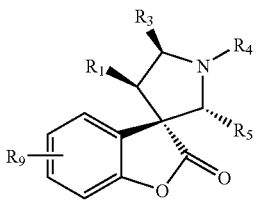

L

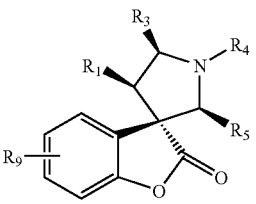

LI

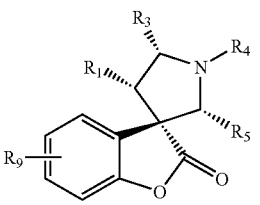

LII

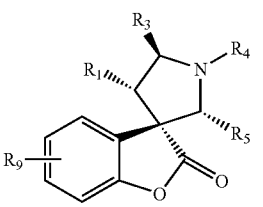

LIII

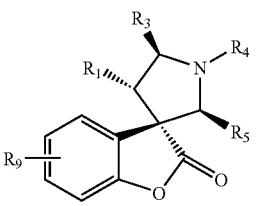

LIV

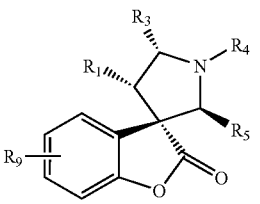

LV

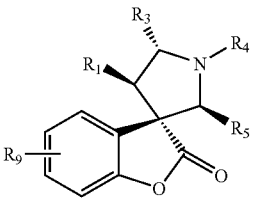

LVI

LVII
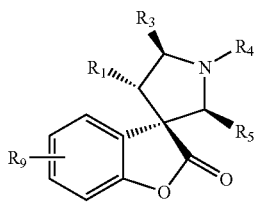

LVIII
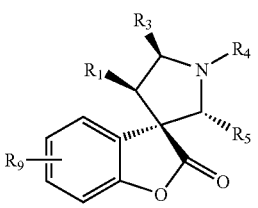

LIX
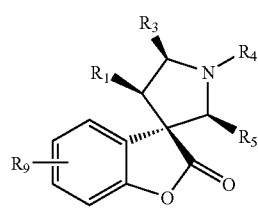

LX
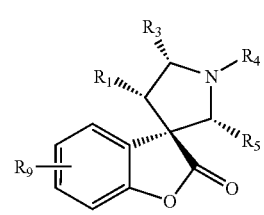

LXI
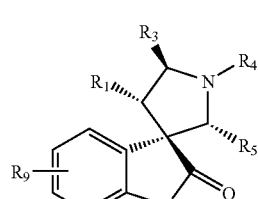

LXII
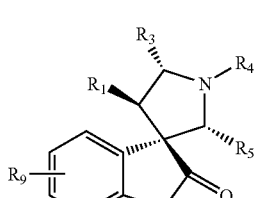

LXIII
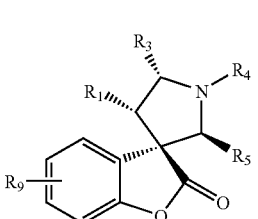

LXIV
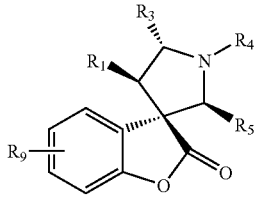

or a pharmaceutically acceptable salt or prodrug thereof.

8. The compound of claim 1, having Formula LXV:

LXV
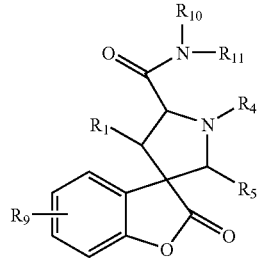

or a pharmaceutically acceptable salt or prodrug thereof, wherein:
$R_{10}$ is hydrogen, and
$R_{11}$ is an optionally substituted cycloalkyl-alkyl or monocyclo-heterocycloalkyl group or a dihydroxyalkyl amino group not containing a hydroxyl group at the 3-position of the alkyl group;
or $R_{10}$ and $R_{11}$ together form an optionally substituted monocyclo-heterocycloalkyl group.

9. The compound of claim 8, having one of Formulae LXVI and LXVII:

LXVI
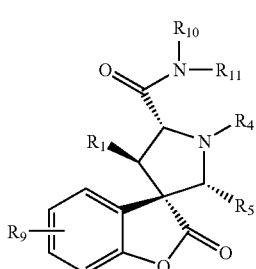

LXVII
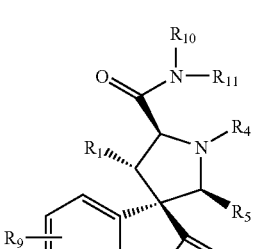

or a pharmaceutically acceptable salt or prodrug thereof.

10. A pharmaceutical composition comprising a compound of claim 1 and a pharmaceutically acceptable carrier.

11. A kit comprising a compound of claim 1.

12. The kit of claim 11, further comprising instructions for administering said compound to an animal.

13. The kit of claim 11, further comprising an additional agent(s).

14. The kit of claim 13, wherein said additional agent(s) is a chemotherapeutic agent.

15. The kit of claim 12, wherein said instructions are for administering said compound to an animal having a hyperproliferative disease.

16. The kit of claim 15, wherein said hyperproliferative disease is cancer.

* * * * *